(12) United States Patent
Kanderian

(10) Patent No.: US 8,483,972 B2
(45) Date of Patent: Jul. 9, 2013

(54) SYSTEM AND METHOD FOR GENOTYPE ANALYSIS AND ENHANCED MONTE CARLO SIMULATION METHOD TO ESTIMATE MISCLASSIFICATION RATE IN AUTOMATED GENOTYPING

(75) Inventor: Sami Kanderian, Germantown, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 95 days.

(21) Appl. No.: 13/172,104

(22) Filed: Jun. 29, 2011

(65) Prior Publication Data
US 2012/0116687 A1     May 10, 2012

Related U.S. Application Data

(63) Continuation-in-part of application No. 12/759,415, filed on Apr. 13, 2010.

(60) Provisional application No. 61/168,649, filed on Apr. 13, 2009, provisional application No. 61/359,821, filed on Jun. 29, 2010.

(51) Int. Cl.
*G06F 19/00* (2006.01)
*G06F 15/00* (2006.01)

(52) U.S. Cl.
USPC .................................. 702/20; 700/1

(58) Field of Classification Search
None
See application file for complete search history.

(56) References Cited

U.S. PATENT DOCUMENTS

| | | | |
|---|---|---|---|
| 6,015,667 A | 1/2000 | Sharaf | |
| 6,960,437 B2 | 11/2005 | Enzelberger et al. | |
| 7,392,199 B2 | 6/2008 | Karlov et al. | |
| 2002/0197630 A1 | 12/2002 | Knapp et al. | |
| 2005/0042639 A1 | 2/2005 | Knapp et al. | |
| 2005/0233335 A1 | 10/2005 | Wittwer et al. | |
| 2006/0019253 A1 | 1/2006 | Wittwer et al. | |
| 2007/0026421 A1 | 2/2007 | Sundberg et al. | |
| 2007/0184455 A1 | 8/2007 | Arrowsmith et al. | |
| 2007/0231799 A1 | 10/2007 | Knight et al. | |
| 2008/0163824 A1 | 7/2008 | Moser et al. | |
| 2008/0287308 A1 | 11/2008 | Hubbell et al. | |
| 2009/0035766 A1 | 2/2009 | Khan et al. | |
| 2009/0112484 A1 | 4/2009 | Boles et al. | |
| 2010/0145624 A1 | 6/2010 | Kishore et al. | |

FOREIGN PATENT DOCUMENTS

| | | | |
|---|---|---|---|
| WO | 2004097577 A2 | 11/2004 | |
| WO | 2005075683 A1 | 8/2005 | |
| WO | 2008025093 A1 | 3/2008 | |

OTHER PUBLICATIONS

Anne et al., "Dynamics of Electron Transport by Elastic Bending of Short DNA Duplexes. Experimental Study and Quantitative Modeling of the Cyclic Voltammetric Behavior of 3'-Ferrocenyl DNA End-Grafted on Gold," J. Am. Chem. Soc., vol. 128, pp. 542-557 (2006) (abstract).

Erdem et al., "Novel hybridization indicator methylene blue for the electrochemical detection of short DNA sequences related to the hepatitis B Virus," Anal. Chim. Acta, vol. 422, pp. 139-149 (2000) (abstract).

Fan et al., "Electrochemical interrogation of conformational changes as a reagentless method for the sequence-specific detection of DNA," Proc. Natl. Acad. Sci. U.S.A., vol. 100, pp. 9134-9137 (2003).

Gooding, "Electrochemical DNA Hybridization Biosensors" Electroanalysis, vol. 14, pp. 1149-1156 (2002) (abstract).

Gooding et al., "The ion gating effect: using a change in flexibility to allow label free electrochemical detection of DNA hybridisation," Chem. Commun., pp. 1938-1939 (2003).

Herrmann et al. "Amplicon DNA Melting Analysis for Mutation Scanning and Genotyping: Cross-Platform Comparison of Instruments and Dyes" Clinical Chemistry 52(3):494-503 (2006).

Kopp et al., "Chemical Amplification: Continuous-Flow PCR on a Chip," Science, vol. 280, pp. 1046-1048 (1998).

Lagally et al., "Single-Molecule DNA Amplification and Analysis in an Integrated Microfluidic Device," Analytical Chemistry, 73(3), pp. 565-570 (2001).

Lai et al., "Rapid, sequence-specific detection of unpurified PCR amplicons via a reusable, electrochemical sensor," Proc. Natl. Acad. Sci. U.S.A., vol. 103, pp. 4017-4021 (2006).

Lee et al., "In vitro cytotoxicity of GC sequence directed alkylating agents related to distamycin," J. Med. Chem., vol. 36, No. 7, pp. 863-870 (1993) (abstract).

(Continued)

*Primary Examiner* — John S Brusca
(74) *Attorney, Agent, or Firm* — Rothwell, Figg, Ernst & Manbeck, P.C.

(57) ABSTRACT

The present invention relates to methods and systems for the analysis of the dissociation behavior of nucleic acids. The present invention includes methods and systems for analyzing dynamic profiles of genotypes of nucleic acids, including the steps of using a computer, including a processor and a memory, to convert dynamic profiles of known genotypes of a nucleic acid to multi-dimensional data points, wherein the dynamic profiles each comprise measurements of a signal representing a physical change of a nucleic acid containing the known genotype relative to an independent variable; using the computer to reduce the multi-dimensional data points into reduced-dimensional data points; and generating a plot of the reduced-dimensional data points for each genotype. The present invention also relates to methods and systems for calculating error statistics for an assay for identifying a genotype in a biological sample using an enhanced Monte Carlo simulation method to generate a set of N random data points for each known genotype within a class of known genotypes, where each set of N random data points has the same mean data point and covariance matrix as a data set for each of the known genotypes.

56 Claims, 28 Drawing Sheets

OTHER PUBLICATIONS

Liew, M., et al. "Genotyping of Single-Nucleotide Polymorphisms by High-Resolution Melting of Small Amplicons," Clin.Chem. vol. 50, No. 7, pp. 1156-64 (2004).

Mearns et al., "DNA Biosensor Concepts Based on a Change in the DNA Persistence Length upon Hybridization," Electroanalysis, vol. 18, pp. 1971-1981 (2006) (abstract).

Mikkelsen, "Electrochemical biosensors for DNA sequence detection," Electroanalysis, vol. 8, pp. 15-19 (1996) (abstract).

Palecek, "From polarography of DNA to microanalysis with nucleic acid-modified electrodes," Electroanalysis, vol. 8, pp. 7-14 (1996) (abstract).

Park et al., "Cylindrical compact thermal-cycling device for continuous-flow polymerase chain reaction," Analytical Chemistry, 75, pp. 6029-6033 (2003).

Ririe et al., "Product Differentiation by Analysis of DNA Melting Curves During the Polymerase Chain Reaction," Analytical Biochemistry 245:154-160 (1997) (abstract).

Wittwer et al., "High-Resolution Genotyping by Amplicon Melting Analysis Using LCGreen," Clinical Chemistry, vol. 49, No. 6, pp. 853-860 (2003).

Xiao et al., "Single-step electronic detection of femtomolar DNA by target-induced strand displacement in an electrode-bound duplex," Proc. Natl. Acad. Sci. U.S.A., vol. 103, pp. 16677-16680 (2006).

PCT International Search Report and Written Opinion, issued in PCT/US 11/42342 on Jan. 24, 2012, 22 pages.

Friedman, et al., "Using Bayesian Networks to Analyze Expression Data," Journal of Computational Biology, vol. 7, Nos. 3/4, pp. 601-620 (2000).

Galeeva. et al, "Measuring correlation risk," Datasheet, CMG, Morgan Stanley, (Jan. 11, 2007).

Yueng, et al, "Principal component analysis for clustering gene expression data," Bioinformatics, vol. 17, No. 9, pp. 763-774 (2001).

Probability Cross Table

Temperature range included in analysis: 54 to 87°C

| Known\Called | Wild Type | Heterozygous | Homozygous | No Call | Frequency |
|---|---|---|---|---|---|
| ▶ Wild Type | 9.9991E-001 | 0 | 0 | 1.0002E-004 | 3.33E-001 |
| Heterozygous | 0 | 1E000 | 0 | 2.1962E-006 | 3.33E-001 |
| Homozygous | 0 | 0 | 1E000 | 1.5315E-010 | 3.33E-001 |

Note: Column Headers = Called Genotypes, Row Headers = Known Genotypes
Error Rate   0 or 1 in inf
No Call Rate   3.4039E-005 or 1 in 2.9378E004 —— 1602

- ⦿ Monte Carlo Simulation (Training set distribution)   ⦿ Allow no calls
- ○ Actual validation melt curve data   ○ Force call

Probability Cross Table

Temperature range included in analysis: 54 to 74°C

| Known\Called | Wild Type | Heterozygous | Homozygous | No Call | Frequency |
|---|---|---|---|---|---|
| ▶ Wild Type | 9.9697E-001 | 0 | 0 | 3.0336E-003 | 3.33E-001 |
| Heterozygous | 1E-004 | 9.6957E-001 | 3.4037E-003 | 2.6924E-002 | 3.33E-001 |
| Homozygous | 0 | 3.924E-004 | 9.2852E-001 | 7.1087E-002 | 3.33E-001 |

Note: Column Headers = Called Genotypes, Row Headers = Known Genotypes
Error Rate   1.2974E-003 or 1 in 7.7077E002
No Call Rate   3.3648E-002 or 1 in 2.9378E001 —— 1602

- ⦿ Monte Carlo Simulation (Training set distribution)   ⦿ Allow no calls
- ○ Actual validation melt curve data   ○ Force call

Probability Cross Table

Temperature range included in analysis: 74 to 87°C

| Known\Called | Wild Type | Heterozygous | Homozygous | No Call | Frequency |
|---|---|---|---|---|---|
| ▶ Wild Type | 9.5043E-001 | 0 | 5.8719E-004 | 4.8984E-002 | 3.33E-001 |
| Heterozygous | 0 | 1 | 0 | 0 | 3.33E-001 |
| Homozygous | 1.2813E-003 | 0 | 9.6123E-001 | 3.7489E-002 | 3.33E-001 |

Note: Column Headers = Called Genotypes, Row Headers = Known Genotypes
Error Rate   6.2219E-004 or 1 in 1.6072E003
No Call Rate   2.8795E-002 or 1 in 3.4728E001 —— 1602

- ⦿ Monte Carlo Simulation (Training set distribution)   ⦿ Allow no calls
- ○ Actual validation melt curve data   ○ Force call

FIG. 16

SYSTEM AND METHOD FOR GENOTYPE ANALYSIS AND ENHANCED MONTE CARLO SIMULATION METHOD TO ESTIMATE MISCLASSIFICATION RATE IN AUTOMATED GENOTYPING

CROSS-REFERENCE TO RELATED APPLICATIONS

This application is a continuation-in-part of U.S. patent application Ser. No. 12/759,415 filed Apr. 13, 2010, which itself claims priority to U.S. Provisional Patent Application Ser. No. 61/168,649, filed on Apr. 13, 2009, which is incorporated herein by reference in its entirety. This application further claims priority to U.S. Provisional Application Ser. No. 61/359,821, filed Jun. 29, 2010, the entirety of which is also incorporated herein by reference.

BACKGROUND

1. Field of the Invention

The present invention relates to methods for the analysis of nucleic acids and the identification of genotypes present in biological samples. More specifically, embodiments of the present invention relate to automated methods for genotyping and analyzing the sequences of nucleic acids. More specifically, embodiments of the present invention relate to methods for genotyping through visual identification of data and the assessment of assays through visual comparison of data and/or quantification of the quality of the assay.

2. Description of Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. The polymerase chain reaction, or PCR, is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies to be detected and analyzed. In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR see *Real-Time PCR: An Essential Guide*, K. Edwards et al., eds., Horizon Bioscience, Norwich, U.K. (2004).

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification in microfluidic devices is usually accomplished in one of two methods. In the first method, the sample solution is loaded into the device and the temperature is cycled in time, much like a conventional PCR instrument. In the second method, the sample solution is pumped continuously through spatially varying temperature zones. See, e.g., Lagally et al. (*Analytical Chemistry* 73:565-570 (2001)), Kopp et al. (*Science* 280:1046-1048 (1998)), Park et al. (*Analytical Chemistry* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Once there are a sufficient number of copies of the original DNA molecule, the DNA can be characterized. One method of characterizing the DNA is to examine the DNA's dissociation behavior as the DNA transitions from double stranded DNA (dsDNA) to single stranded DNA (ssDNA). The process of causing DNA to transition from dsDNA to ssDNA with increasing temperature is sometimes referred to as a "high-resolution temperature (thermal) melt (HRTm)" process, or simply a "high-resolution melt" process. Alternatively, the transition from ssDNA to dsDNA may be observed through various electrochemical methods, which generate a dynamic current as the potential across the system is changed.

Melting profile analysis is an important technique for analyzing nucleic acids. In some methods, a double stranded nucleic acid is denatured in the presence of a dye that indicates whether the two strands are bound or not. Examples of such indicator dyes include non-specific binding dyes such as SYBR® Green I, whose fluorescence efficiency depends strongly on whether it is bound to double stranded DNA. As the temperature of the mixture is raised, a reduction in fluorescence from the dye indicates that the nucleic acid molecule has melted, i.e., unzipped, partially or completely. Thus, by measuring the dye fluorescence as a function of temperature, information is gained regarding the length of the duplex, the GC content or even the exact sequence. See, e.g., Ririe et al. (*Anal Biochem* 245:154-160, 1997), Wittwer et al. (Clin Chem 49:853-860, 2003), Liew et al. (Clin Chem 50:1156-1164 (2004), Herrmann et al. (Clin Chem 52:494-503, 2006), Knapp et al. (U.S. Patent Application Publication No. 2002/0197630), Wittwer et al. (U.S. Patent Application Publication No. 2005/0233335), Wittwer et al. (U.S. Patent Application Publication No. 2006/0019253), Sundberg et al. (U.S. Patent Application Publication No. 2007/0026421) and Knight et al. (U.S. Patent Application Publication No. 2007/0231799).

An alternative method for analyzing a nucleic acid uses voltammetry to detect electrochemical biosensors to detect nucleic acid hybridization. Electrochemical technology is miniaturizable, accurate, and sensitive with controlled reaction conditions. Both label-free and labeled approaches exist for detecting nucleic acid hybridization. Label-free approaches generally rely on changes to the electrical properties of an interface when bound to a nucleic acid, changes in flexibility between rigid dsDNA and more flexible ssDNA, or electrochemical oxidation of guanine bases. See, e.g., Gooding (*Electroanalysis* 14:1149-1156, 2002), Gooding et al. (*Chem. Commun.* 2003:1938-1939, 2003), Mearns et al. (*Electroanalysis* 18:1971-1981, 2006); Paleck (*Electroanalysis* 8:7-14, 1996). Labeled approaches for detecting nucleic acid hybridization are more common and well-known than label-free approaches. These approaches generally involve redox active molecules that intercalate between Watson-Crick base pairs of a nucleic acid or in the minor or major grooves of the nucleic acid secondary structure, and thus do not interact with single-stranded nucleic acids. Examples of such redox active molecules include $Co(Phen)_3^{3+}$, $Co(bpy)_3^{3+}$, and Methylene Blue. See, e.g., Mikkelsen (*Electroanalysis* 8:15-19, 1996); Erdem et al. (*Anal. Chim. Acta* 422:139-149, 2000). In some cases, the redox active molecules bind preferentially to either dsDNA or ssDNA. Another alternative method includes attaching a label group, such as a ferrocene group, to the end of a nucleic acid probe, which is immobilized on an electrode surface. See, e.g., Mearns et al. (*Electrochemistry* 18:1971-1981, 2006); Anne et al. (*J. Am. Chem. Soc.* 128:542-547, 2006); Lai et al. (*Proc. Natl. Acad. Sci. U.S.A.* 103:4017-4021, 2006); Fan et al. (*Proc. Natl. Acad. Sci. U.S.A.* 100:9134-9147, 2003); Xiao et al. (*Proc. Natl. Acad. Sci. U.S.A.* 103:16677-16680, 2006). The single-stranded probe molecule is flexible enough that the ferrocene group may come within close enough contact with the electrode surface to be oxidized or reduced. However, upon hybridization, the rigid double-stranded nucleic acid molecule stands normal to the electrode surface, and the ferrocene group is sufficiently far from the electrode that it will not be oxidized or reduced.

These systems may all be interrogated through cyclic voltammetry. By applying an electric potential that increases or decreases over time across the system, a variable electric current is generated as the label or DNA molecule is oxidized or reduced. Complete hybridization of the target molecule to the probe molecule will generate a characteristic dynamic profile of current generated versus voltage applied. Incomplete hybridization, which would occur if the target molecule contained a mutant genotype, would result in a differing dynamic profile of current generated versus voltage applied. Thus, different nucleic acid sequences may be distinguished from one another through examination of their respective voltammograms.

Some nucleic acid assays require differentiation between potential genotypes within a class of known genotypes. Generally, for thermal melt analysis, researchers will visually inspect a thermal melt profile to determine the melting temperature of the nucleic acid in the sample. However, some nucleic acid assays require identification of a single nucleotide change where the difference in melting temperature ($T_m$) between the wild type nucleic acid and a mutant nucleic acid is quite small (e.g. less than 0.25° C.). This level of temperature resolution is difficult to achieve in a visual inspection. Furthermore, visual inspection of thermal melt profiles to determine melting temperature ignores significant additional information contained in the profiles, such as the overall shape and distribution of the profile.

In developing assays and instruments for automated genotype classification, it is important to assess and quantify the expected accuracy and misclassification rate for a particular population, as well as for a particular assay. Quantitative and visual feedback to scientists and engineers is important, as it tells them how well an assay as a whole is expected to perform in the field. Components of the assay, or assay parameters, may include the following: (i) assay reagents responsible for the amplification of DNA segments, including the primers responsible for amplification of DNA segments where mutations of interest may lie; (ii) sensing and control instrumentation for an assay; (iii) reaction conditions under which the sensing and control instrumentation operates; (iv) the process by which raw data is collected from such an assay (e.g. the imaging system to monitor fluorescence, temperature control systems, temperature sensing systems); and (v) algorithms or assay software that transform raw data into an identification of a genotype.

A change in any of the assay parameters has the potential of making the system perform better or worse. It is important to quantify and visualize the improvement or detriment to the system performance resulting from the change. The quantitative indicator would be a measure of how well different genotypes are separated, and a visual representation would be a scatter of points representing different genotypes plotted on a page. A single data point is defined by one or more parameters obtained from a DNA sample of a particular genotype. The parameters may be derived from some sort of analysis on raw signals, whether static or dynamic in nature. Parameters from static raw signals may come from a steady state absorbance value where by an unknown DNA sample fluoresces when the individual strands bind to their complementary tagged allele.

Though a user can visualize the separation of the genotype clusters described by reduced-dimensional data points, it would be useful to quantify their separation defined by the expected misclassification rate. One way to quantify the separation of different genotypes is to compute the ratio of the determinants of the between-class scatter matrix to the within-class scatter matrix as described in U.S. patent application Ser. No. 12/759,415. However, at times, these matrices may be singular yielding a determinant of 0, making this quantifier impossible to compute. Furthermore the optimal quantifier for the separation of genotypes is an error statistic for the assay, as the objective of the scientist or engineer responsible for developing new assays is to minimize this error statistic. More specifically, it is also important to know which of the genotypes are most likely to be misclassified as another genotype. Further, it is important to know an overall expected misclassification rate for the assay.

Genotyping systems that yield dynamic signals may include high resolution thermal melt curves where fluorescence versus temperature or the derivative of fluorescence versus temperature yields a unique signature or profile for each genotype. In this instance, an operator may identify a genotype by visually comparing dynamic temperature profiles that yield a unique signature or profile for each genotype. Typically an operator identifies the genotype by visually comparing these dynamic signatures, not as data points. In U.S. patent application Ser. No. 12/759,415, each dynamic curve is transformed to a correlation vector defined by a set of parameters (usually 3). A correlation vector with three parameters can be plotted as a point in three-dimensional space; likewise, a correlation vector with two parameters can be plotted in two-dimensional space.

It is much simpler to visually classify and observe the degree of separation of different genotypes using a cluster plot of data points rather than looking at the dynamic melt curves from which they were derived. Furthermore, if a data point is not contained within any clusters of previously identified genotypes, this may indicate the discovery of a new mutation or genotype.

Once these parameters or data points are derived, the DNA sample may be identified either visually by the operator or automatically by a computer classification algorithm (as in U.S. patent application Ser. No. 12/759,415). In the genotyping problem, a DNA sample is classified as one of several possible genotypes. Typically, the genotype may either be classified as homozygous wildtype (WT), heterozygous (HE) or homozygous mutant (HM) depending on the alleles that make up the DNA. No mutations in either allele results in a homozygous wildtype genotype. A mutation in only one allele results in a heterozygous genotype and a mutation in both alleles results in a homozygous genotype. Data points from the same genotype form a cluster. In genotyping or any classification problem, it is important for clusters representing different genotypes or classes to be far apart from each other to minimize the likelihood of misclassification. Currently the visual representation of different high resolution melts is displayed as dynamic curves to the user. Representing each dynamic curve as a data point is useful because in a classification problem such as this, the position of a point relative to genotype clusters obtained from a training set of known genotypes tells the user which cluster a DNA sample of unknown genotype likely belongs to along with a level of confidence.

In trying to approximate the misclassification rate of an assay, one may be able to run a limited sample size study of $N_E$ experimental DNA samples, make the automated identification of the samples, and derive the percentage of incorrect calls from that process. However, due to the fact that a study is limited in number, the calculation of the misclassification rate in this fashion can result in a misclassification rate that is a multiple of $1/N_E$, and thus a misclassification rate of less than $1/N_E$ cannot be detected. When rapidly going through multiple iterations of assay, instrument or algorithm design, $N_E$ cannot be very large in the interest of saving time and resources in the process of system optimization. Therefore, it is difficult to assess the improvement or detriment to system performance that results from a change without running multiple experiments.

Accordingly, what are desired are methods and systems for data analysis that are capable of visually representing data obtained from genotyping analytic systems in a way that allows an investigator to analyze the set of all genotypes together, or to identify a genotype based on how closely it maps to profiles representing the same genotype and how separate it is from other genotypes. In one instance, the methods and systems may be for high resolution melt analysis and may utilize data obtained from thermal melt analysis. Further, there is a need for a method and system that allows a user to estimate an error statistic for an assay without running numerous experiments using the assay. Further, there is a need for being able to measure and/or visually represent the improvement in an error statistic of an assay when a parameter (e.g., reaction components) is altered, discriminating the resulting thermal melt curves and obtaining DNA sequence information from these melting curves, especially where these thermal melt curves are differentiated by a small temperature range. Also desired are methods and systems for high resolution melt analysis that more accurately identify thermal melt curves that facilitate detection of sequence information for DNA that contain one or more peaks or mutations. Also desired are methods and systems that are capable of more accurately identifying a nucleic acid sequence and discriminating between similar sequences while taking into account both features of the profile as well as the overall shape. Also desired are methods that are capable of rapidly identifying a genotype with minimal intervention and decision-making from the user.

SUMMARY OF THE INVENTION

The present invention relates to methods and systems for the analysis of nucleic acids and the identification of genotypes present in biological samples. More specifically, embodiments of the present invention relate to automated methods and systems to analyze the sequences of nucleic acids and to classify their genotypes that are useful for determining the identity of the genotype of a nucleic acid that is present in a biological sample.

The present invention relates to methods and systems for the analysis of nucleic acids, assays for the analysis of nucleic acids, and the identification of genotypes present in biological samples. More specifically, embodiments of the present invention relate to methods and systems to aid investigators in analysis of genotypes present in biological samples through visualization and plotting, as well as analysis of assays for the identification of genotypes and quantified comparisons of the quality of the assays.

Thus, in one aspect, the present invention provides a method of analyzing dynamic profiles of genotypes of nucleic acids. This method may include the steps of using a computer, including a processor and a memory, to convert dynamic profiles of known genotypes of a nucleic acid to multi-dimensional data points, using the computer to reduce the multi-dimensional data points into reduced dimensional data points, and generating a plot of the reduced-dimensional data points for each genotype. In this aspect, the dynamic profiles may each comprise measurements of a signal representing a physical change of a nucleic acid containing the known genotype relative to an independent variable.

In one embodiment, the plot may include multiple axes that each represent boundaries for where correlation of the dynamic profiles represented is maximal against various average profiles of known genotypes for each known genotype. In another embodiment, generating the plot may include showing the extent to which clusters of the reduced-dimensional data points for each of the known genotypes are separated. In one embodiment, the multi-dimensional data points may be (n+1)-dimensional data points, and the reduced-dimensional data points may be n-dimensional data points. In another embodiment, the multi-dimensional data points may be three-dimensional data points and the reduced-dimensional data points may be two-dimensional data points.

In a further embodiment, the method may include the additional steps of using the computer to generate a mean and covariance matrix for each of the known genotypes from the set of reduced-dimensional data points representing dynamic profiles for each corresponding known genotype, using the computer to calculate eigenvalues and eigenvectors of each of the covariance matrices, using the computer to calculate a rotation angle and major/minor axis width of an n-ellipse for each of the known genotypes, and displaying the n-ellipses on the plot. In a further embodiment, the major/minor axis widths of each n-ellipse may be proportioned such that each n-ellipse covers a multiple of the standard deviation of the reduced dimensional data points representing the dynamic profiles of its respective genotype. In another further embodiment, the major/minor axis widths of each n-ellipse may be proportioned such that each n-ellipse contains a predetermined percentage of the reduced-dimensional data points for its respective genotype. In another embodiment, the rotation angle of the n-ellipse for a known genotype may be calculated from the arctangent of the ratio of elements of an eigenvector of the covariance matrix for that genotype.

In another further embodiment, the method may further include the steps of using the computer to convert a dynamic profile of an unknown genotype of a nucleic acid to a multi-dimensional data point representing the unknown genotype, using the computer to transform the multi-dimensional data point representing the unknown genotype into a reduced-dimensional data point representing the unknown genotype, and plotting the reduced-dimensional data point representing the unknown genotype on the plot. A further embodiment of this method may also include the steps of using the computer to generate a mean and covariance matrix for each of the known genotypes from the set of reduced-dimensional data points representing dynamic profiles of each corresponding known genotype, using the computer to calculate eigenvalues of each of the covariance matrixes, using the computer to calculate a rotation angle and major/minor axis widths of an n-ellipse for each of the known genotypes, displaying the n-ellipses on the plot, and determining if the reduced-dimensional data point representing the unknown genotype falls within the n-ellipse representing one of the known genotypes. In a further embodiment of this method, the major/minor widths of each n-ellipse may be proportioned such that each n-ellipse covers a multiple of the standard deviation of the reduced-dimensional data points representing the dynamic profiles of its respective genotypes. In an alternate further embodiment, the major/minor axis widths of each n-ellipse may be proportioned such that each n-ellipse contains a predetermined percentage of the reduced-dimensional data points for each respective genotype. In an alternate further embodiment, the rotation angle of the n-ellipse for a known genotype may be calculated from the arctangent of the ratio of the elements of an eigenvector of the covariance matrix for that genotype.

In another embodiment, the method may further comprise the step of visually identifying the unknown genotype from the determination of whether the reduced-dimensional data point falls within an n-ellipse representing one of the known genotypes.

In another embodiment, the multi-dimensional data points may be correlation vectors. The correlation vectors may be comprised of correlation coefficients between a dynamic profile and an average dynamic profile for each known genotype in a class of genotypes. The average dynamic profile of a known genotype may include average measurements of the signal representing the physical change of a nucleic acid containing the known genotype relative to the independent variable.

Another aspect of the invention is a method of determining the identity of a genotype in a biological sample. That method may include the steps of generating a dynamic profile of an unknown genotype, using a computer including a processor and a memory to compare the dynamic profile of the unknown genotype with an average dynamic profile of each known genotype in a class of known genotypes to generate a multi-dimensional data point, transforming the multi-dimensional data point to a reduced-dimensional data point, generating a plot showing the reduced-dimensional data point for the unknown genotype, and identifying the unknown genotype. In this aspect, a dynamic profile may include measurements of a signal representing a physical change of a nucleic acid containing the unknown genotype relative to an independent variable. Further, in this aspect, the average dynamic profile of a known genotype may include average measurements of a signal representing the physical change of a nucleic acid containing the known genotype relative to the independent variable. The reduced-dimensional data point, in this aspect, may be a correlation vector. A correlation vector may include correlation coefficients between the dynamic profile of the unknown genotype and the average dynamic profile for each known genotype in the class of genotypes as its elements.

In one further embodiment, the step of comparing the dynamic profile of the unknown genotype with an average dynamic profile of each known genotype may include correlating the dynamic profile of the unknown genotype with an average dynamic profile of each known genotype. In a further embodiment, the method may in one instance further include the step of visually identifying the genotype based on the location of the reduced-dimensional data point for the unknown genotype on the plot.

Yet another aspect of the present invention is a system for analyzing dynamic profiles of genotypes of nucleic acids. In one embodiment, this system may include a computer, including a processor and a memory, a conversion module configured to convert dynamic profiles of known genotypes of a nucleic acid to multi-dimensional data points, a reduction module configured to reduce the multi-dimensional data points into reduced-dimensional data points; a display device, and a plotting module, configured to generate a plot of the reduced-dimensional data points for each genotype on the display device. In this embodiment, the dynamic profiles may each comprise measurements of a signal representing a physical change of a nucleic acid containing the known genotype relative to an independent variable.

In a further embodiment, the plot may include multiple axes that each represent boundaries where correlation of the dynamic profiles represented is maximal against average profiles of known genotypes for each genotype. In another embodiment, the plotting module may be configured to display the extent to which clusters of the reduced-dimensional data points for each of the known genotypes are separated. In another embodiment, the multi-dimensional data points may be three-dimensional data points and the reduced-dimensional data points may be two-dimensional data points.

In one embodiment, the system may further include a statistical matrix generation module configured to generate a mean and covariance matrix for each of the known genotypes from the set of reduced-dimensional data points representing dynamic profiles of each corresponding known genotype; an eigenvalue/eigenvector calculation module, configured to calculate eigenvalues and eigenvectors of each of the covariance matrixes, and an ellipse generation module, configured to calculate a rotation angle and major/minor axis widths of an n-ellipse for each of the known genotypes. In this embodiment, the plotting module may be configured to display the n-ellipses on the plot. In a further embodiment, the ellipse generation module may determine the major/minor axis widths of each n-ellipse such that each n-ellipse covers a multiple of the standard deviation of the reduced-dimensional data points representing the dynamic profiles of its respective genotype. Alternately, the ellipse generation module may proportion the major/minor axis widths of each n-ellipse such that each n-ellipse contains a predetermined percentage of the reduced-dimensional data points for its respective genotype. In another further embodiment, the rotation angle of the n-ellipse for a known genotype may be calculated from the arctangent of the ratio of elements of an eigenvector of the covariance matrix for that genotype.

In another embodiment, the conversion module may be configured to convert a dynamic profile of an unknown genotype of a nucleic acid to a multi-dimensional data point representing the unknown genotype, the reduction module may be configured to reduce the multi-dimensional data point representing the unknown genotype into a reduced-dimensional data point representing the unknown genotype, and the plotting module may be configured to plot the reduced-dimensional data point representing the unknown genotype on the plot. This embodiment may further include an identification module configured to identify the unknown genotype. In a further embodiment, the identification module may be configured to determine if the reduced-dimensional data point representing the unknown genotype falls within one of the n-ellipses for a known genotype. The ellipse generation module may proportion the major/minor axis widths of each n-ellipse such that each n-ellipse covers a multiple of the standard deviation of the reduced-dimensional data points representing the dynamic profiles of its respective genotype. Alternately, the ellipse generation module may proportion the major/minor axis widths of each n-ellipse such that each n-ellipse contains a predetermined percentage of the reduced-dimensional data points for its respective genotype. In yet another embodiment, the rotation angle of the n-ellipse for a known genotype may be calculated from the arctangent of the ratio of elements of an eigenvector of the covariance matrix for that genotype.

In one embodiment, the multi-dimensional data points may be correlation vectors. The correlation vectors may each comprise correlation coefficients between the dynamic profile and an average dynamic profile for each known genotype in a class of genotypes. The average dynamic profile of a known genotype may comprise average measurements of a signal representing the physical change of a nucleic acid containing the known genotype relative to the independent variable.

Another aspect of the invention is a method and system for calculating an error statistic for an assay for identifying a genotype in a biological sample. In one embodiment, a method comprises the steps of a) generating, using the assay, dynamic profiles of each known genotype of a nucleic acid; b) using a computer, including a processor and a memory, to convert the dynamic profiles of each known genotype to data points; c) using the computer to transform the data points such that each element of the data points is normally distributed, and grouping the data points by each known genotype to generate a data set for each known genotype; d) using the computer to generate a mean data point and covariance matrix for each of the known genotypes from the data set for each genotype; e) using the computer to, for each of the known genotypes, generate a set of N random data points with the same mean data point and covariance matrix for each of the known genotypes; f) using the computer to calculate an error statistic for the assay, based upon at least one of the generated sets of N random data points for a known genotype. The dynamic profiles may each comprise measurements of a signal representing a physical change of a nucleic acid containing the known genotype relative to an independent variable.

In a further embodiment, the step of generating N random data points with the same mean data point and covariance matrix for each known genotype may include the following steps: i) using the computer to calculate a Cholesky factorization of the covariance matrix for each known genotype; ii) using the computer to generate a set of N random data points with a normalized distribution for each known genotype; iii) using the computer to transform the set of N random data points for each known genotype with the Cholesky factorization for that genotype to generate N transformed random data points for each known genotype; and iv) using the computer to shift each of the set of N transformed random data points for each known genotype by the mean data point for that known genotype to generate N random data points with the same mean data point and covariance matrix for each known genotype.

The error statistic may be one of several different error statistics. In one embodiment, the error statistic may be an expected misclassification rate for a known genotype. In another embodiment, the error statistic may be an overall expected misclassification rate for the assay. In yet another embodiment, the error statistic may be the posterior probability that an unknown sample containing one of the known genotypes would be identified as an individual known genotype.

In one embodiment of the method, the independent variable in the assay may be temperature. In this embodiment, the assay may further comprise a fluorescent intercalating dye, and the measurements of a signal representing a physical change of a nucleic acid may be measurements of fluorescence of the fluorescent dye.

In one embodiment of the method, the method may include the additional steps of using the computer to reduce the data points in each data set for each known genotype into reduced-dimensional data points, and generating a plot of the reduced-dimensional data points for each genotype.

In another embodiment of the method, the method may further include the step of generating a probability cross table. The elements of the probability cross table may be posterior probabilities that a known genotype would be identified as a possible known genotype.

In another embodiment of the invention, the computer may further include an input device, and step f) of the method may include receiving a no-call threshold value from the input device and using the computer to calculate an error statistic for the assay, based upon the no-call threshold value and the at least one set of generated N random data points for a known genotype.

In another aspect of the invention, the invention includes a method of optimizing an assay. This method may be performed by a) generating, using a first assay, dynamic profiles of each known genotype of a nucleic acid; b) using a computer including a processor and a memory to convert the dynamic profiles of each known genotype from the first assay to data points; c) using the computer to transform the data points from step b) such that each element of the data points is normally distributed, and grouping the data points by each known genotype to generate a data set for each known genotype; d) using the computer to generate a mean data point and covariance matrix for each of the known genotypes from the data set for each genotype from step c); e) using the computer to, for each of the known genotypes, generate a set of N random data points with the same mean data point and covariance matrix for each of the known genotypes; f) using the computer to calculate an error statistic for the first assay, based upon at least one of the generated sets of N random data points for a known genotype; g) repeating steps a-f for at least a second assay having a second set of assay parameters, wherein the first and second set of assay parameters have at least one differing assay parameter; and h) comparing the error statistic for the first assay and the error statistic for the second assay. The first assay may have a first set of assay parameters. The dynamic profiles may each comprise measurements of a signal representing a physical change of a nucleic acid containing the known genotype relative to an independent variable. In one embodiment, the at least one differing assay parameter may be selected from the group consisting of reaction components, assay equipment, analysis software, measured independent variable, or range over which the independent variable of the dynamic profiles is measured.

Another aspect of the present invention is a system for calculating an error statistic for an assay. In that aspect, one embodiment of that aspect is a system comprising an assay and a computer. The assay may be configured to generate dynamic profiles of each known genotype of a nucleic acid. The computer, which may include a processor and a memory, may be configured to perform the steps of: a) converting the dynamic profiles generated by the assay of each known genotype to data points; b) transforming the data points such that each element of the data points is normally distributed, and grouping the data points by each known genotype to generate a data set for each known genotype; c) generating a mean data point and covariance matrix for each of the known genotypes from the data set for each genotype; d) generating N random data points with the same mean data point and covariance matrix for each of the known genotypes; and e) calculating an error statistic for the assay, based upon the generated N random data points for a known genotype. The output module may be configured to output the error statistic for the assay.

In a further embodiment of the invention, the step of generating N random data points with the same mean data point and covariance matrix for the known genotype may include i) calculating a Cholesky factorization of the covariance matrix for each known genotype; ii) generating N random data points with a normalized distribution for each known genotype; iii) transforming the N random data points for each known genotype with the Cholesky factorization for that genotype to generate N transformed random data points for each known genotype; and iv) shifting each of the N random data points for each known genotype by the mean data point to generate a set of N random data points with the same mean data point and covariance matrix for each known genotype.

Again, in this aspect of the invention, the error statistic may be one of several different error statistics. In one embodiment, the error statistic may be an expected misclassification rate for a known genotype. In another aspect, the error statistic may be an overall expected misclassification rate for the assay. In yet another embodiment, the error statistic may be the posterior probability that an unknown sample containing one of the known genotypes would be identified as an individual known genotype.

In one embodiment, the independent variable in the assay may be temperature, and the assay may further include a fluorescent intercalating dye. In this embodiment, the measurements of a signal representing a physical change of a nucleic acid may be measurements of fluorescence of the fluorescent dye.

In one embodiment, the computer may be further configured to perform the steps of reducing the data points in each data set for each known genotype into reduced-dimensional data points and said output module is further adapted to generate a plot of the reduced-dimensional data points for each genotype.

In one embodiment, the computer may be further configured to perform the step of generating a probability cross table. The elements of the probability cross table may be posterior probabilities that a known genotype would be identified as a possible known genotype; and wherein said output module is further configured to output the probability cross table for the assay.

In one embodiment of the invention, the assay may be a first assay, which may have a first set of assay parameters, and the system may further include a second assay that may include a second set of assay parameters. The second assay may be configured to generate a second set of dynamic profiles of each known genotype of a nucleic acid. Those dynamic profiles may each comprise measurements of a signal representing a physical change of a nucleic acid containing the known genotype relative to an independent variable. Further, the first and second set of assay parameters may have at least one differing assay parameter.

In this embodiment, the computer may further be configured to perform the steps of: f) repeating steps a-e for the second assay; and g) comparing the error statistic for the first assay and the error statistic for the second assay. Further, the output module may be further adapted to output the error statistic for the second assay.

BRIEF DESCRIPTION OF THE FIGURES

The accompanying drawings, which are incorporated herein and form part of the specification, illustrate various embodiments of the present invention.

FIG. 16 illustrates the cross-probability tables for the assays corresponding to FIGS. 14A-C, using a 95% "no-call" threshold value.

DETAILED DESCRIPTION OF PREFERRED EMBODIMENTS

Figure 1A:
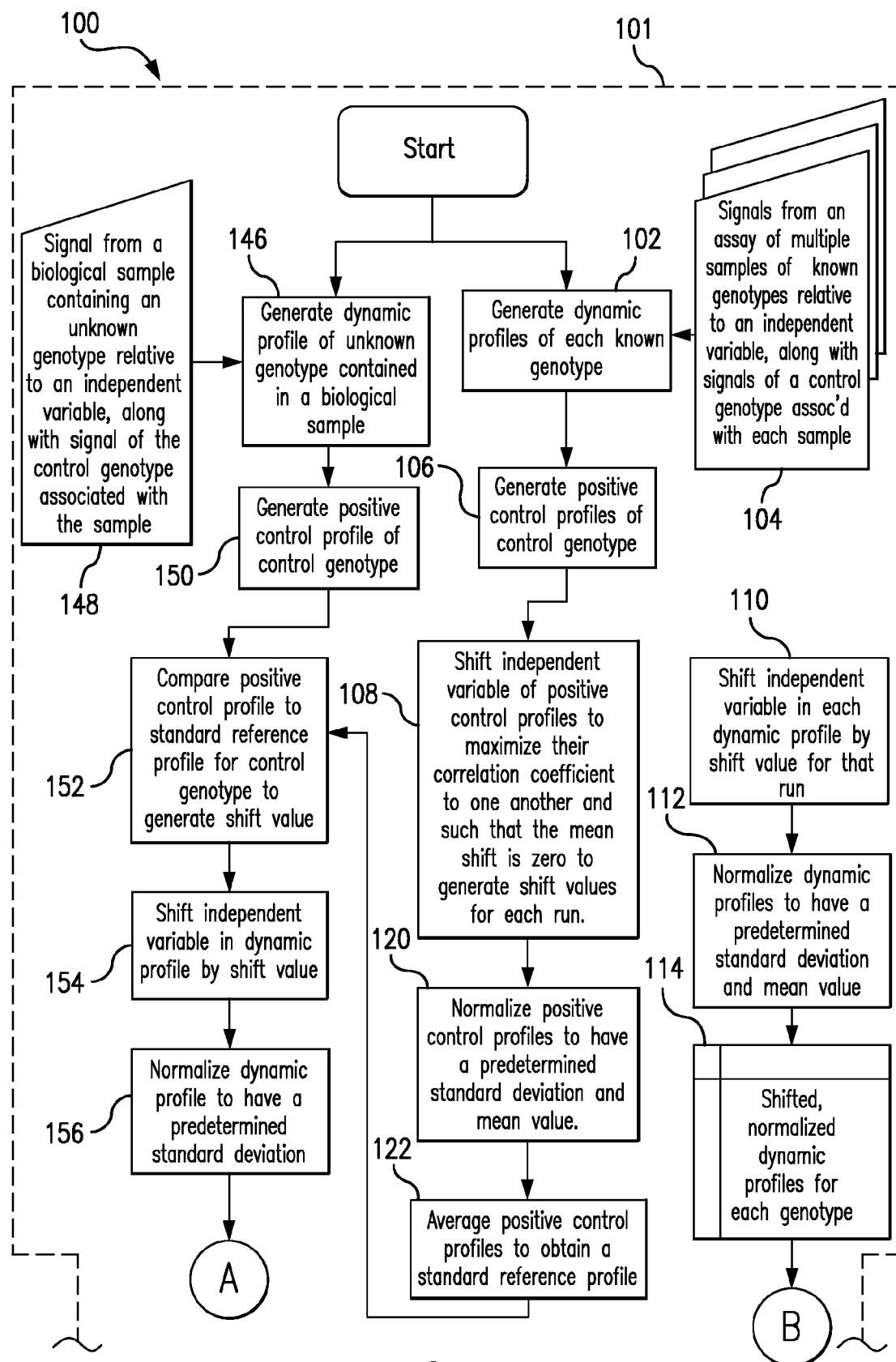
FIGS. 1A-B illustrate a flowchart showing one embodiment of a method of analyzing dynamic profiles of genotypes of nucleic acids through plotting the dynamic profiles as reduced-dimensional data points.

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, N.Y., Gait, *Oligonucleotide Synthesis: A Practical Approach*, 1984, IRL Press, London, Nelson and Cox (2000), Lehninger, *Principles of Biochemistry* 3rd Ed., W. H. Freeman Pub., New York, N.Y. and Berg et al. (2002) *Biochemistry*, 5th Ed., W. H. Freeman Pub., New York, N.Y., all of which are herein incorporated in their entirety by reference for all purposes.

Thermal melt curves of fluorescence have been used to determine the melting temperature of a DNA strand when denatured from the duplex state to the two separate single strands via a ramp increase in temperature. Typically, the melting temperature or $T_m$ is defined to be the temperature at which 50% of the paired DNA strands have denatured into single strands. Intercalating dyes that fluoresce when bound to double stranded DNA and lose their fluorescence when denatured are often used in measuring $T_m$. Typically, the negative derivative of fluorescence with respect to temperature (−dF/dT) has been used in the determination of $T_m$. In typical systems, the temperature at the peak −dF/dT is used as an estimate of the melting temperature $T_m$.

The −dF/dT derivative curve may be obtained using a Savitsky-Golay (SG) derivative filter which is capable of estimating the derivative of any signal. Savitsky-Golay filters are low pass, Finite Impulse Response (FIR) derivative filters, and their application to any dynamical signal is obtained through the convolution of the FIR filter parameters with the raw signal. When the spacing of the independent variable is uniform, the filtered results can give first order and higher order derivatives of the dependant variable relative to the independent variable equivalent. The effect of such a filter is equivalent to a moving polynomial fit, followed by the evaluation of the derivative of that polynomial evaluated at the center of the window. Other methods for obtaining the −dF/dT derivative curve may be found in U.S. Patent Application Publication No. 2009/0112484, which is incorporated herein by reference.

The present invention relates to methods and systems for the analysis of dynamic profiles of nucleic acids. These dynamic profiles are data sets containing measurements of a signal representing a physical change of a nucleic acid relative to an independent variable. One example of this physical change is the dissociation behavior of nucleic acids. The analysis of the dynamic profiles of nucleic acids of a particular genotype can assist in the identification of nucleic acids and the identification of particular genotypes. More specifically, the present invention relates to methods and systems for determining the identity of the genotype of a nucleic acid present in a biological sample through analysis of dynamic profiles of an unknown genotype in a biological sample.

As stated above, a dynamic profile contains measurements of a signal representing a physical change of a nucleic acid relative to an independent variable. This physical change may be, for example, denaturation of a nucleic acid containing a particular genotype. Such a dynamic profile may be, for instance, a molecular melt curve or a thermal denaturation curve. The signal in such a thermal denaturation curve for nucleic acids may be, for example, measured thermal parameters, fluorescence of indicator dyes/molecules, fluorescence polarization, dielectric properties, or the like. A dynamic profile which is a molecular melt curve or a thermal denaturation curve may be generated by melting curve analysis.

Melting curve analysis is typically carried out either in a stopped flow format or in a continuous flow format. In one example of a stopped flow format, flow is stopped within a microchannel of a microfluidic device while the temperature in that channel is ramped through a range of temperatures required to generate the desired melt curve. In an alternative stopped flow format, melting curve analysis is done in a chamber to which the nucleic acid sample has been added. In one example of a continuous flow format, a melting curve analysis is performed by applying a temperature gradient along the length (direction of flow) of a microchannel of a microfluidic device. If the melting curve analysis requires that the molecules being analyzed be subjected to a range of temperatures extending from a first temperature to a second temperature, the temperature at one end of the microchannel is controlled to the first temperature, and the temperature at the other end of the length is controlled to the second temperature, thus creating a continuous temperature gradient spanning the temperature range between the first and second selected temperatures. An example of an instrument for performing a melting curve analysis is disclosed in U.S. Patent Application Publication No. 2007/0231799, incorporated herein by reference in its entirety. Although the present invention is applicable to the analysis of dynamic profiles obtained in any environment, it is particularly useful for dynamic profiles obtained in the microfluidic environment because of the need for greater sensitivity in this environment.

In accordance with certain aspects of the invention, dynamic profiles are generated by elevating the temperature of a molecule or molecules, e.g., of one or more nucleic acids, for a selected period of time and measuring a signal (i.e. a detectable property) emanating from the molecule or molecules, wherein the signal indicates an extent of denaturation of the nucleic acid. This period of time can range, for example, from about 0.01 second through to about 1.0 minute or more, from about 0.01 second to about 10 seconds or more, or from about 0.1 second to about 1.0 second or more, including all time periods in between. In one embodiment, heating comprises elevating the temperature of the molecule or molecules by continuously increasing the temperature of the molecule or molecules. For example, the temperature of the molecule(s) can be continuously increased at a rate in the range of about 0.1° C./second to about 1° C./second. Alternatively, the temperature of the molecule(s) can be continuously increased at a slower rate, such as a rate in the range of about 0.01° C./second to about 0.1° C./second, or at a faster rate, such as a rate in the range of about 1° C./second to about 10° C./second. The heating can occur through application of an internal or an external heat source, as is known in the art.

The actual detection of one or more physical changes of the molecules can be detected in numerous methods depending on the specific molecules and reactions involved. For example, the denaturation of the molecules can be tracked by following fluorescence or emitted light from molecules in the assay. The degree of, or change in, fluorescence is correlational or proportional to the degree of change in conformation of the molecules being assayed. Thus, in some methods, the detection of a property of the molecule(s) comprises detecting a level of fluorescence or emitted light from the molecules(s) that varies as a function of relative amounts of binding. In one configuration, the detecting of fluorescence involves a first molecule and a second molecule, wherein the first molecule is a fluorescence indicator dye or a fluorescence indicator molecule and the second molecule is the target molecule to be assayed. In one embodiment, the fluorescence indicator dye or fluorescence indicator molecule binds or associates with the second molecule by binding to hydrophobic or hydrophilic residues on the second molecule. The methods of detecting optionally further comprise exciting the fluorescence indicator dye or fluorescence indicator molecule to create an excited fluorescence indicator dye or excited fluorescence indicator molecule and discerning and measuring an emission or quenching event of the excited fluorescence indicator dye or fluorescence indicator molecule.

Dynamic profiles may be generated in a number of different methods. In some methods, the generation of the dynamic profile includes providing one molecule comprising a fluorescence indicator dye or fluorescence indicator molecule, and at least a second molecule comprising, one or more of an enzyme, a ligand, a peptide nucleic acid, a cofactor, a receptor, a substrate, a protein, a polypeptide, a nucleic acid (either double-stranded or single-stranded), an antibody, an antigen, or an enzyme complex. Fluorescence of the first molecule in the presence of the second molecule as a function of temperature is measured and the resulting data constitutes a dynamic profile. In other methods, the generation of the dynamic profile comprises measuring a change in the fluorescence of one molecule that is correlative or proportional to a change in a physical property of another molecule(s) due to a change in temperature. In still other methods, the generation of a dynamic profile comprises measuring the change in the total free energy of the system as a function of temperature without the presence of a second molecule. Typically, the methods also include generating a positive control profile of a control sample, or a known dynamic profile of a known sample, in a similar manner.

Several techniques exist for the measurement of the denaturation of the molecules of interest, and any of these can be used in generating the data to be analyzed in accordance with aspects of the present invention. Such techniques include fluorescence, fluorescence polarization, fluorescence resonance energy transfer, circular dichroism and UV absorbance. Briefly, the fluorescence techniques involve the use of spectroscopy to measure changes in fluorescence or light to track the denaturation/unfolding of the target molecule as the target molecule is subjected to changes in temperature. Spectrometry, e.g. via fluorescence, is a useful method of detecting thermally induced denaturation/unfolding of molecules. Many different methods involving fluorescence are available for detecting denaturation of molecules (e.g. intrinsic fluorescence, numerous fluorescence indicator dyes or molecules, fluorescence polarization, fluorescence resonance energy transfer, etc.) and are optional embodiments of the present invention. These methods can take advantage of either internal fluorescent properties of target molecules or external fluorescence, i.e. the fluorescence of additional indicator molecules involved in the analysis.

A method of measuring the degree of denaturation/unfolding of the target molecule is through monitoring of the fluorescence of dyes or molecules added to the microfluidic device along with the target molecule and any test molecules of interest. A fluorescence dye or molecule refers to any fluorescent molecule or compound (e.g., a fluorophore) which can bind to a target molecule either once the target molecule is unfolded or denatured or before the target molecule undergoes conformational change by, for example, denaturing and which emits fluorescent energy or light after it is excited by, for example, light of a specified wavelength.

One dye type used in the microfluidic devices is one that intercalates within strands of nucleic acids. The classic example of such a dye is ethidium bromide. An exemplary use of ethidium bromide for binding assays includes, for example, monitoring for a decrease in fluorescence emission from ethidium bromide due to binding of test molecules to nucleic acid target molecules (ethidium bromide displacement assay). See, e.g., Lee, M. et al. (*J Med Chem* 36(7):863-870 (1993)). The use of nucleic acid intercalating agents in measurement of denaturation is known to those in the art. See, e.g., Haugland (*Handbook of Fluorescent Probes and Research Chemicals*, Molecular Probes, Inc., Eugene, Oreg. (1996)).

Dyes that bind to nucleic acids by mechanisms other than intercalation can also be employed in embodiments of the invention. For example, dyes that bind the minor groove of double stranded DNA can be used to monitor the molecular unfolding/denaturation of the target molecule due to temperature. Examples of suitable minor groove binding dyes are the SYBR Green family of dyes sold by Molecular Probes Inc. (Eugene, Oreg., USA). See, e.g., Haugland (*Handbook of Fluorescent Probes and Research Chemicals*, Molecular Probes, Inc., Eugene, Oreg., USA (1996)). SYBR Green dyes will bind to any double stranded DNA molecule. When a SYBR Green dye binds to double stranded DNA, the intensity of the fluorescent emissions increases. As more double stranded DNA are denatured due to increasing temperature, the SYBR Green dye signal will decrease. Another suitable dye is LCGreen Plus sold by Idaho Technology, Inc. (Salt Lake City, Utah, USA).

Fluorescence polarization (FP) provides a useful method to detect hybridization formation between molecules of interest. This method is especially applicable to hybridization detection between nucleic acids, for example, to monitor single nucleotide polymorphisms (SNPs). Generally, FP operates by monitoring, the speed of rotation of fluorescent labels, such as fluorescent dyes or molecular beacons, e.g. before, during, and/or after binding events between molecules that comprise the test and target molecules. In short, binding of a test molecule to the target molecule ordinarily results in a decrease in the speed of rotation of a bound label on one of the molecules, resulting in a change in FP.

Fluorescence resonance energy transfer (FRET) can be used to track the conformational changes of the target molecule (and interactions with test molecules which can bind with the target molecule) as a function of temperature. FRET relies on a distance-dependent transfer of energy from a donor fluorophore to an acceptor fluorophore. If an acceptor fluorophore is in close proximity to an excited donor fluorophore, then the emission of the donor fluorophore can be transferred to the acceptor fluorophore. This causes a concomitant reduction in the emission intensity of the donor fluorophore and an increase in the emission intensity of the acceptor fluorophore. Since the efficiency of the excitation transfer depends, inter alia, on the distance between the two fluorophores, the technique can be used to measure extremely small distances such as would occur when detecting changes in conformation. This technique is particularly suited for measurement of binding reactions, protein-protein interactions, e.g., such as a protein of interest binding to an antibody and other biological events altering the proximity of two labeled molecules. Many appropriate interactive labels are known. For example, fluorescent labels, dyes, enzymatic labels, and antibody labels are all appropriate.

Circular dichroism (CD) can be used to follow the conformational changes of the target molecules/text molecules as a function of temperature and can be used to construct molecular melt curves. CD is a type of light absorption spectroscopy which measures the difference in absorbance by a molecule between right-circularly polarized light and left-circularly polarized light. CD is quite sensitive to the structure of polypeptides and proteins.

UV absorbance can also be used to detect and/or track denaturation of nucleic acid molecules, and/or to quantify the total amount of nucleic acid. UV can be employed to measure the extent of denaturation because the UV absorbance value of single stranded nucleic acid molecules is greater than the absorbance value of double stranded nucleic acid molecules.

An alternative method of measuring the degree of denaturation/unfolding of the target molecule is through monitoring of the current generated by a sample relative to the voltage applied across the sample to generate a voltammetry curve. In some methods, the generation of a voltammetry curve includes providing one molecule comprising one or more of an enzyme, a ligand, a peptide nucleic acid, a cofactor, a receptor, a substrate, a protein, a polypeptide, a nucleic acid (either double-stranded or single-stranded), an antibody, an antigen, or an enzyme complex. In addition, at least one second molecule comprising a redox-active molecule that preferentially binds to either a single-stranded nucleic acid or a double-stranded nucleic acid is provided. Generally, a probe molecule is provided which represents a particular protein or nucleic acid of interest; the probe molecule may be a ligand, a peptide nucleic acid, a substrate, a protein, a polypeptide, a nucleic acid (either double-stranded or single-stranded, and may be an oligonucleotide which is capable of hybridizing to a specific sequence of interest), an antibody, an antigen, or an enzyme complex. Preferably, the redox-active molecule interacts with a double-stranded nucleic acid in such a way that its oxidation or reduction potential is different than when it does not interact with a double-stranded nucleic acid. Such redox-active molecules often intercalate between Watson-Crick base pairs of a nucleic acid or in the minor or major grooves of the nucleic acid secondary structure, and thus do not interact with single-stranded nucleic acids. Alternatively, the redox-active molecule may bind preferentially to a sequence of interest. A non-limiting example of such a redox-active molecule is a probe molecule containing a sequence of interest to be interrogated and a ferrocene label attached at a free end of the probe.

Application of an electric potential across a sample containing such a redox-active molecule will generate an electric current, which will vary with the application of different electric potentials. By applying a range of electric potential across the sample, various measurements of electric current generated may be obtained in order to create a dynamic profile. For example, if the first molecule has completely hybridized to the probe molecule, the dynamic profile will differ from one generated if the first molecule incompletely hybridizes to the probe molecule, or does not hybridize at all. The dynamic profile may then be plotted as a curve representing current versus voltage in order to generate a voltammetry curve. The processes and flow charts described herein for the dynamic profile in the case of high resolution thermal melt would apply to the dynamic profile in the case of electrochemical voltammetry.

The dynamic profile generated through these methods may be plotted on any available medium used for plotting data to generate a signature curve. Signature curves are useful because they allow a person to visually match one dynamic profile to another, which may allow a researcher to discriminate between different genotypes in a biological sample. An initial signature curve may also be mathematically modified or operated upon in order to generate a second signature curve, which may allow a researcher to more easily compare a signature curve representing an unknown genotype to one representing a known genotype. A signature curve may be, for instance, a thermal melt curve. Thermal melt curves are generally plots of the negative derivative of fluorescence with respect to temperature ($-dF/dT$), which are generated from thermal melt data. Researchers may 'visually' look at these curves in order to distinguish between different genotypes based on the differences in the appearance of their thermal melt curves, which represent differences in the dynamic profiles between the two genotypes. This visual inspection requires a high degree of user intervention in the identification of a particular genotype, since a researcher must match the signature curve generated from the dynamic profile of the unknown genotype to a known signature curve generated from a dynamic profile of a known genotype. Furthermore, subtle differences in the shape of the curve may not be detected by human inspection, and may lead to misidentification of the genotype.

Quantitative methods for analyzing the differences in thermal melt curves of an unknown genotype also exist. One quantitative method includes determining the temperature at the peak −dF/dT. This temperature is used as an estimate of the melting temperature of the nucleic acid $T_m$. This estimate of the $T_m$ of the nucleic acid may be used to classify the genotype of the nucleic acid by comparing its value to a distribution of melting temperatures for a known genotype. However, this method also presents potential shortcomings. For example, this method uses only one point of the entire thermal melt curve—the peak of the derivative—in order to determine the genotype. This possibly ignores the overall shape of the thermal melt curve, including the width of the curve and the height of the peak, which may be useful in determining the genotype of the sample. Further, two single nucleotide polymorphisms may have differences in melting temperature that are less than 0.5° C. apart. In this case, the resolution of the two thermal melt curves generated from data obtained in a microfluidic device may be too low in order to allow one to identify differences between the melting temperatures of the two genotypes, and thus between the genotypes.

In an aspect of the invention, dynamic profiles generated by the means outlined above may be converted to single multi-dimensional data points. Each coordinate of the data point may be a correlation coefficient between a dynamic profile and an average normalized profile for each known genotype in the class of known genotypes. Another aspect of the invention provides a method for reducing the number of dimensions in the multi-variable data points representing the dynamic profiles to reduced-dimensional data points, and plotting the reduced dimensional data points. Various embodiments of the invention will be described in greater detail below, along with reference to the figures.

Each dynamic profile may include measurements of a signal representing a physical change of a nucleic acid containing the known genotype relative to an independent variable as described herein. As such, the dynamic profile is derived from the signal measurements representing the physical change of the nucleic acid. Multiple dynamic profiles for each known genotype of the class of known genotypes may be generated. Multiple dynamic profiles may be normalized so that they all have the same mean and standard deviation. Each correlation vector may comprise correlation coefficients for the dynamic profile against each average normalized dynamic profile of each known genotype in the class of known genotypes. That is, each of the individual dynamic curves that make up a training set (as defined in U.S. patent application Ser. No. 12/759,415 and incorporated herein by reference) are correlated against each of the average normalized profiles to yield a correlation vector for each dynamic curve in the training set. In a further embodiment, the transformed vectors belonging to the same genotype may be grouped together into a stacked matrix, and a mean data point (whereby each row of the matrix is averaged) and a covariance matrix of the stacked matrix may be obtained.

In another embodiment, the method further includes the step of translating each correlation vector into a reduced-dimensional correlation vector. The transformation vector can be constructed in such a way that when grouped by class, each of the elements are normally distributed. To perform this transformation, a transformation matrix can be used that is selected to result in a normalized distribution by genotype.

Figure 1B:
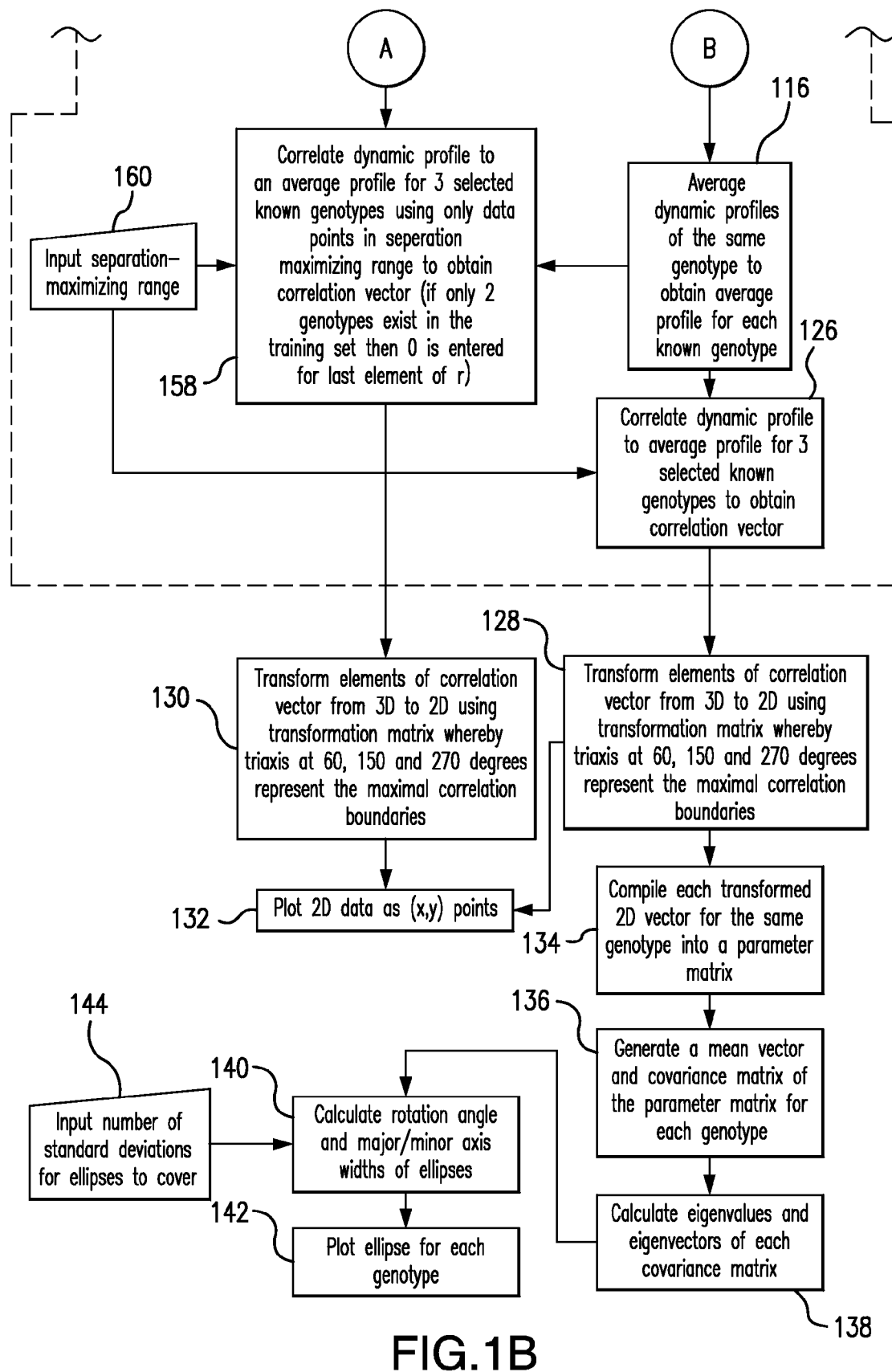

FIGS. 1A-B illustrate a flow chart for method 100 for analyzing a genotype in accordance with one embodiment of the present invention. The method 100 may include a sub-method for generating multi-dimensional data points from dynamic profiles. One non-limiting example of such a sub-method is outlined as submethod 101 in FIG. 1A, which may include the steps delineated by the dashed box. One of ordinary skill in the art will appreciate that other methods for converting dynamic profiles to multi-dimensional data points may exist, such as by determining certain key elements of the dynamic profile and using them to generate data points (e.g., for thermal melt curves, such key parameters could include selecting the melting temperature and curve width of the Savitsky-Golay derivative of the melting curve). Another such non-limiting method is through analysis of the dynamic profiles through principal component analysis.

Figure 2:
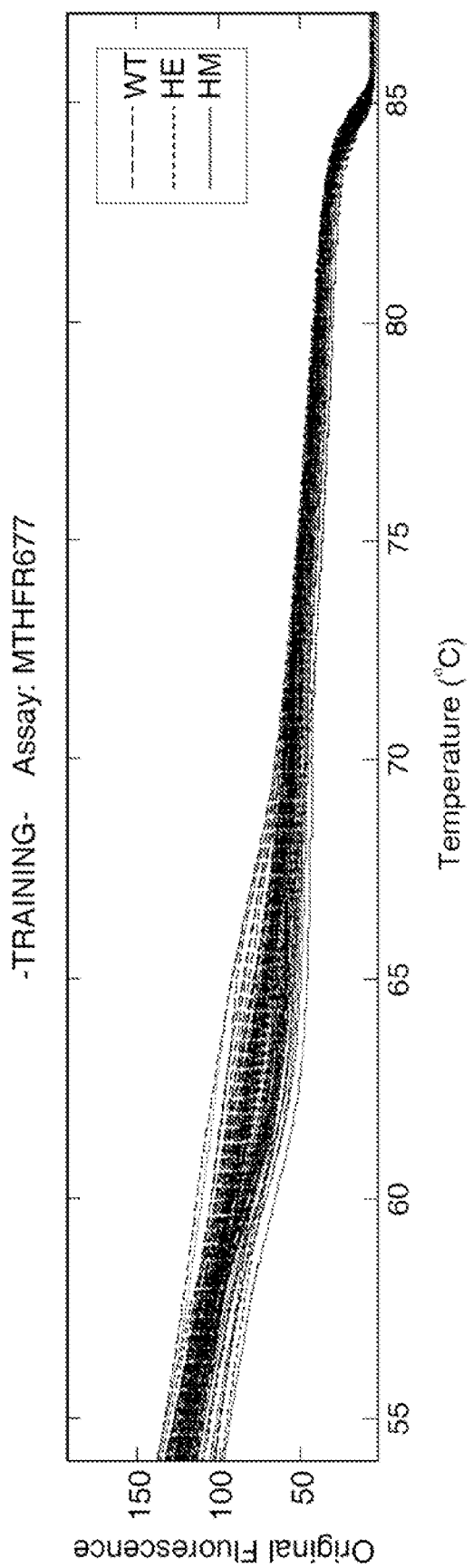
FIG. 2 illustrates a plot of fluorescence versus temperature dynamic profiles for each genotype within the MTHFR 667 polymorphism class.
Figure 3:
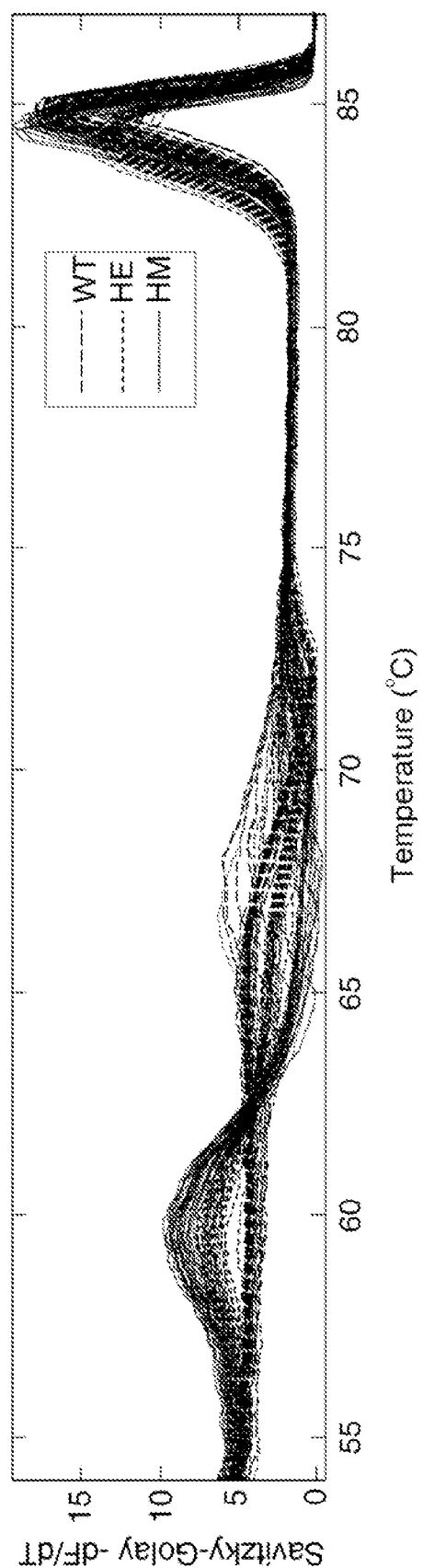
FIG. 3 illustrates a plot of the negative derivative of the fluorescence versus temperature dynamic profiles for each genotype from FIG. 2, within the MTHFR 667 polymorphism class, for temperatures between 54° C. and 87° C.

Step 102 in submethod 101 may include generating a plurality of dynamic profiles of a known genotype contained in a plurality of biological samples. The dynamic profiles may be generated from data generated in step 104. The data in step 104 may be generated by any of the methods described above for generating data for dynamic profiles or signature curves. The dynamic profiles each contain measurements of a signal, y(t), which represents a physical change of a nucleic acid containing the known genotype. These measurements of the signal are recorded relative to an independent variable, x(t). The parameter t may be any parameter over which both the independent variable and the signal are measured. In the case that the measurements in the dynamic profile are generated through thermal melting of a nucleic acid containing the known genotype with intercalating dyes, x(t) is the temperature T(t), and y(t) is the fluorescence, F(t), or the derivative of the fluorescence relative to temperature, −dF/dT. Alternatively, in the case that the dynamic profile is generated through voltammetry of a nucleic acid with a redox-active molecule, x(t) is the electric potential V(t) and y(t) is the electric current I(t). As a non-limiting example, a plot of several dynamic profiles for the three different genotypes in the MTHFR 667 polymorphism is shown in the form of fluorescence versus temperature curves in FIG. 2 and as the derivative of the fluorescence relative to temperature in FIG. 3.

Step 106 of submethod 101 in FIG. 1A includes generating an associated positive control dynamic profile of a control genotype. The associated positive control dynamic profile may be generated at the same time each of the plurality of dynamic profiles of the known genotype is generated. Each positive control dynamic profile of the positive control genotype may be also comprised of measurements of the same signal relative to the same independent variable as the dynamic profile for the known genotype, though the measurements are taken from a positive control sample rather than the sample containing the known genotype. The measurements of the signal for the positive control genotype preferably are generated concurrently in step 104 with the measurements of the signal for the known genotype. This positive control dynamic profile may be compared to a standard reference dynamic profile for the control genotype. Alternatively, the independent variable of each of the positive control dynamic profiles may be shifted by a shift value Δx such that the positive control dynamic profiles match up, and such that the mean of the shift values Δx for all positive control dynamic profiles that are shifted is 0, as is shown in step 108. In step 110 of submethod 101, the independent variable of the dynamic profile associated with a positive control dynamic profile is also shifted by the same shift value Δx as the associated positive control dynamic profile. In order to shift an independent variable in a positive control dynamic profile or dynamic profile by the shift value Δx, Δx is subtracted from or added to the independent variable in the positive control dynamic profile or dynamic profile.

Figure 4:
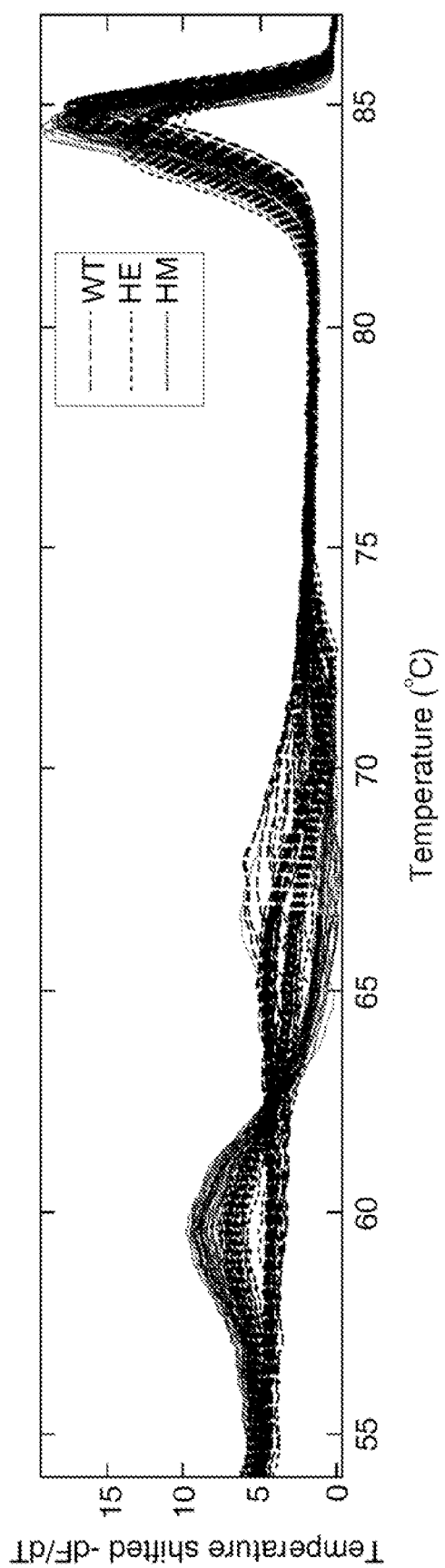
FIG. 4 illustrates the dynamic profiles of FIG. 3 after having been horizontally shifted by a shift value determined by correlation of a positive control dynamic profile to a known dynamic profile for a positive control.

The dynamic profile may be normalized in order to have a predetermined standard deviation, as is shown in step 112 of submethod 101. Optimally, the shifted dynamic profile is normalized. In some embodiments, the normalization procedure also normalizes the dynamic profile in order to have both a predetermined standard deviation and a predetermined average value. The predetermined average value may be zero, and the predetermined standard deviation may be 1. The normalized dynamic profile y'(x) may be calculated as follows:

$$y'(x) = \frac{y(x) - \mu(y(x))}{\sigma(y(x))}$$

wherein $\mu(y(x))$ is the average value of the dynamic profile and wherein $\sigma(y(x))$ is the standard deviation of the dynamic profile. As a non-limiting example, several shifted dynamic profiles, in the form of –dF/dT versus temperature curves, are shown for the three different genotypes in the MTHFR 667 polymorphism, as illustrated in FIG. 4.

Referring back to FIG. 1A, after shifting and normalizing all dynamic profiles associated with a known genotype for each genotype within the class of known genotypes, a set of normalized and shifted dynamic profiles 114 is generated. In some embodiments, these may be entered into data storage for use.

The dynamic profile may be averaged with other dynamic profiles corresponding to the same known genotype in step 116 (see FIG. 1B) of submethod 101. Averaging together several dynamic profiles corresponding to the same known genotype generates an averaged dynamic profile for a known genotype which contains average measurements of the signal representing the physical change of a nucleic acid containing the known genotype relative to the independent variable.

Figure 5:
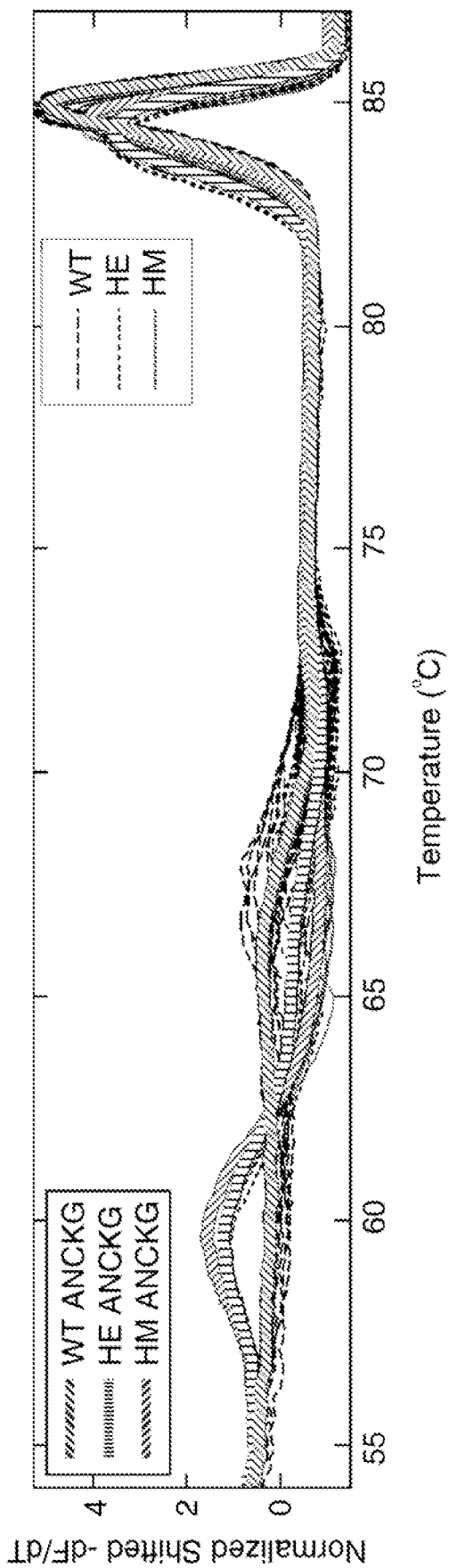
FIG. 5 illustrates the dynamic profile of FIG. 4 after normalization to a predetermined standard deviation, and the average normalized profile of each genotype within the polymorphism class (class of known genotypes).

To generate an average dynamic profile for a known genotype, dynamic profiles for a known genotype may be averaged together. One way to average the dynamic profiles together is to calculate the mean value of the measurement of the signal for each different value of the independent variable across all of the dynamic profiles that are being averaged to make up the average profile for the known genotype. In some embodiments, some outlying data sets may be excluded at the discretion of an investigator. For example, FIG. 5 shows the average profile for each known genotype in the MTHFR 667 polymorphism class as the large, heavy lines among the thinner lines.

In addition, an average positive control dynamic profile may be generated in a similar manner by averaging together positive control dynamic profiles representing the same positive control genotype, as is shown in step 122 (see FIG. 1A). Preferably, the dynamic profiles (or the positive control dynamic profiles) are shifted and normalized, as described above, prior to averaging them together to create an average normalized dynamic profile for the known genotype or the positive control genotype.

As used herein, the class of genotypes may include every genotype to which one would reasonably want to compare the unknown genotype. In some embodiments, the class of genotypes will be those genotypes associated with a particular polymorphism. For example, for the coagulation factor MTHFR 677 single nucleotide polymorphism, there are three possible genotypes associated with the polymorphism: wild type (WT), heterozygous mutant (HE), and homozygous mutant (HM). The class of genotypes in this case would preferably include all three genotypes (WT, HE, and HM), though it may include fewer, and it may include additional genotypes beyond those associated with the particular polymorphism as well.

Referring back to FIG. 1A, in step 120 of submethod 101, each known dynamic profile for the control genotype is normalized to have a predetermined mean and standard deviation. In some embodiments, this normalization procedure is identical to the normalization procedure used for the dynamic profiles, discussed above. In step 122, the positive control dynamic profiles are averaged to generate a standard reference dynamic profile for the control genotype. The standard reference dynamic profile may be calculated in the same manner as the average dynamic profile for a known genotype is calculated.

In step 126 of submethod 101, each dynamic profile of a known genotype which has been used in calculating an average dynamic profile for the known genotype is correlated against the average dynamic profile for each known genotype in order to generate a correlation vector r $$r = \begin{bmatrix} r_1 \\ r_2 \\ \vdots \\ r_{Ng} \end{bmatrix}$$

wherein $r_1, r_2, \ldots, r_{Ng}$ are correlation values between the dynamic profile and each of the average dynamic profiles for each known genotype in the class of known genotypes. While r may be referred to herein as a correlation vector, it should be appreciated that r is one example of a multi-dimensional data point representing a dynamic profile. The correlation vector r may be an $[N_g \times 1]$ matrix, wherein $N_g$ is the number of genotypes that make up all of the possible mutations. Each element of the correlation vector may be a correlation coefficient of the dynamic profile against a different average dynamic profile of a known genotype. The correlation coefficient of a dynamic profile $y_1(x)$ against a second dynamic profile (or an average normalized profile) $y_2(x)$ may be calculated as follows:

$$r(y_1, y_2) = \frac{\sum_{i=1}^{n}[(y_1(i) - \mu_{y1})(y_2(i) - \mu_{y2})]}{(n-1)\sigma_{y1}\sigma_{y2}}$$

where n is the number of points that make up the dynamic profiles, $\mu_{y1}$ and $\mu_{y2}$ are the means of their respective profiles, and $\sigma_{y1}$ and $\sigma_{y2}$ are the respective standard deviations of the profiles. In one embodiment, a separation-maximizing independent variable is input in step 160 preferably using independent variable values contained within the separation-maximizing range to calculate the correlation vector generated in step 126. In one embodiment, the separation-maximizing range may be calculated, for example, using the Enhanced Monte-Carlo Method disclosed herein, or through maximization of the ratio of the between-class scatter to within-class scatter, as disclosed in U.S. patent application Ser. No. 12/759,415.

The correlation coefficient need not be an actual correlation coefficient, but instead may be any value that represents the degree of difference between two sets of data, or two dynamic profiles. Such statistics include, but are not limited to, the sum squared error between the dynamic profile and the average dynamic profile, or the correlation coefficient between the average dynamic profile and the dynamic profile.

Figure 6:
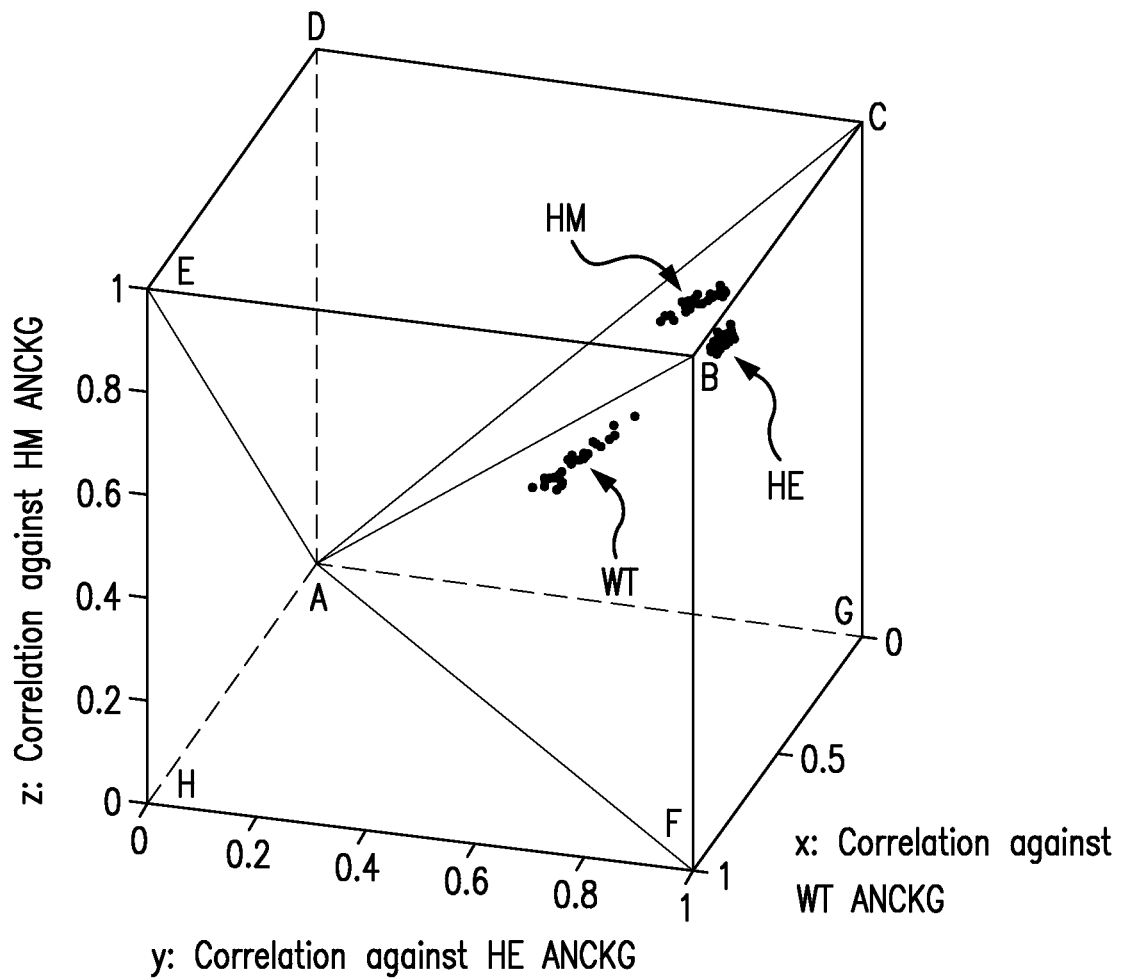
FIG. 6 illustrates a three-dimensional plot containing three-dimensional data points, where each three-dimensional data point represents one of the dynamic profiles from FIG. 5, and the coordinates of each three-dimensional data point are correlation coefficients of the melt curve against each of the average normalized profiles of the known genotypes.

For a given genotype, the correlation coefficients of the various dynamic profiles against the average dynamic profile for a known genotype may not be normally distributed, in that they do not conform to a Gaussian distribution. For example, FIG. 6 shows that, when plotted as data points in 3-dimensional space, the correlation vectors in the training set for the MTHFR 667 polymorphism are not normally distributed. One problem that may arise in this context is that it may be difficult for an investigator to visually distinguish between the data points representing differing genotypes, and it may be difficult for an investigator to see a degree of separation between the genotypes.

Figure 7:
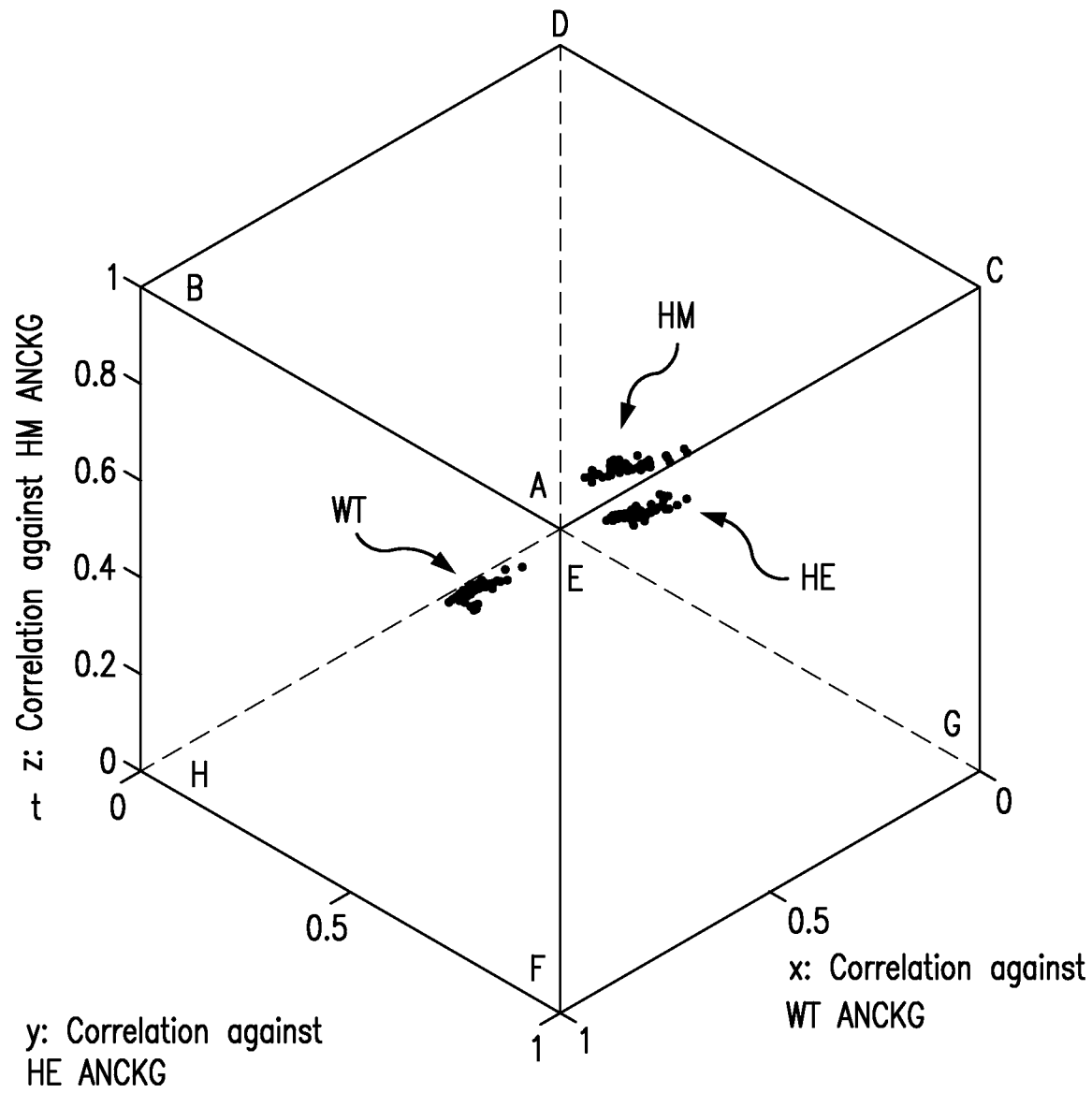
FIG. 7 illustrates a rotation of FIG. 6 such that the (1, 1, 1) plane is normal to the surface.

Referring to FIG. 1B, in step 128, the correlation vector r may be transformed in order to normalize the distribution of the correlation values, while also reducing the number of dimensions in the correlation vector. FIG. 7 shows the distribution of correlation coefficients of a group of dynamic profiles of the MTHFR 667 WT, HE, and HM genotypes arranged such that the (1,1,1) plane is normal to the line of the viewer. This figure shows that by rotating to that particular viewpoint, the genotype clusters become normally distributed and are divided by the visual representations of the x, y, and z axes. To effectively reduce the number of dimensions in this plot, one may transform the three-dimensional correlation vectors (which are multi-dimensional data points) into two-dimensional data points (which are reduced-dimensional data points). By reducing the number of dimensions to two in this embodiment, some information may be lost; however, the correlation vectors become normally distributed and are easily displayed to an investigator in a useful format.

In one embodiment, this transformation may be accomplished by multiplying the correlation vector r by a transformation vector T. If the correlation vector is an $[N_g \times 1]$ matrix, where $N_g$ is the number of genotypes that make up all of the possible mutations, T may be an $[(N_g-h) \times N_g]$ matrix, where h is the reduction in the number of dimensions of the correlation vector.

A reduced-dimensional correlation vector v (which is one example of a reduced-dimensional data point) may then be calculated by multiplying T by the correlation vector r:

$$v = T \cdot r$$

Figure 8:
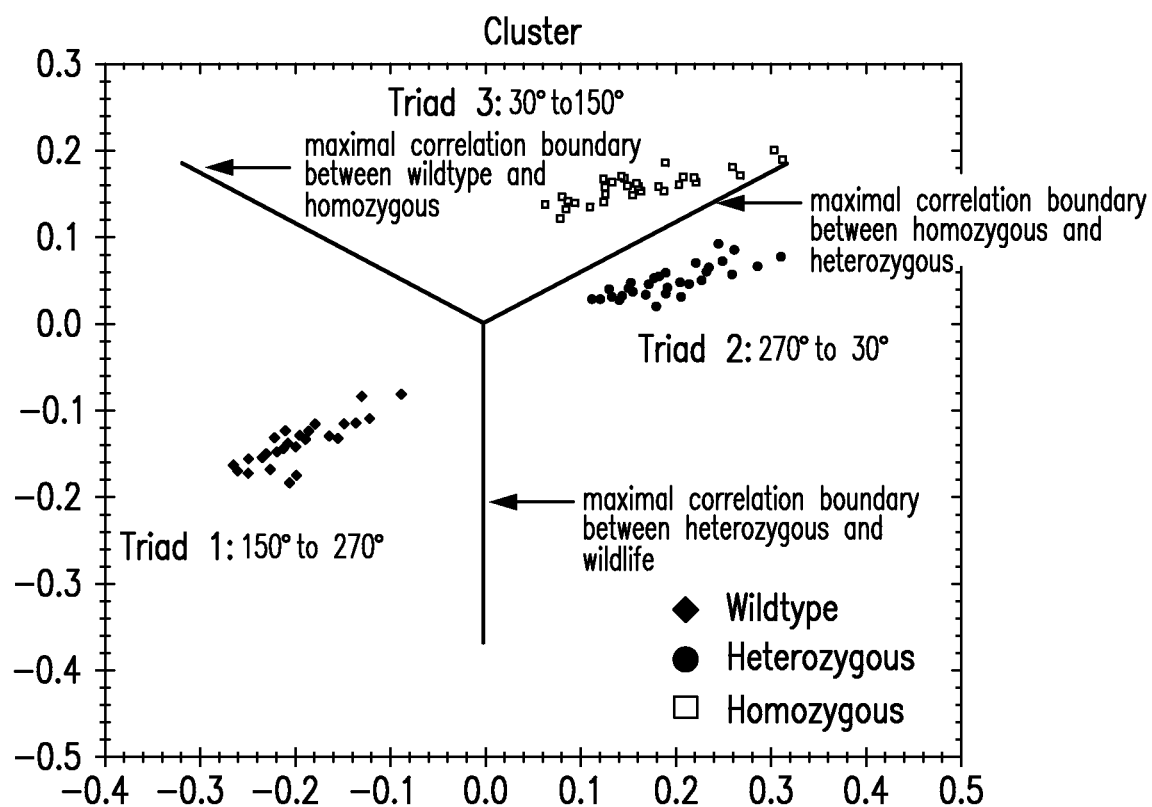
FIG. 8 illustrates a two-dimensional graph showing two-dimensional data points generated by transforming the three-dimensional data points in FIGS. 6 and 7 through use of a transformation matrix.

This results in a reduced-dimensional correlation vector v that has the dimensions $[(N_g-h) \times 1]$. In one embodiment of the invention, T may be derived in such a way as to maximize the ratio of between-class scatter to within-class scatter in order to maximize the separation between different genotypes and minimize the separation between identical genotypes, thus allowing one effectively to show the degree of separation between genotypes. For example, FIG. 8 illustrates a two-dimensional graph showing two-dimensional data points generated by transforming the three-dimensional data points in FIGS. 6 and 7 through use of a transformation matrix. In one embodiment, to derive the plot in FIG. 8, the following transformation matrix T that projects each r onto the plane x+y+z=0 may be used:

$$T = \begin{bmatrix} -1 & 1 & 0 \\ -1/\sqrt{3} & -1/\sqrt{3} & 2/\sqrt{3} \end{bmatrix}$$

Generally, T may be a $2 \times N_g$ matrix, as two-dimensional representations of the correlation vectors are easier to prepare. However, it should be appreciated that T may also be a $3 \times N_g$ matrix in order to permit a three-dimensional representation of correlation vectors with four or more elements.

Referring back to FIG. 1B, in step 132, the reduced-dimensional correlation vectors may be plotted as two-dimensional Cartesian coordinates on a graph. In one embodiment, this graph may also display three axes at 60, 150, and 270 degrees, which represent the boundaries where correlation of the dynamic profile represented by each data point is maximal against the average profiles of the other known genotypes. For example, FIG. 8 is a graph which shows reduced-dimensional correlation vectors for the WT, HE, and HM genotypes of the MTHFR 667 single nucleotide polymorphism and the three axes separating the three genotypes from each other. Such a graph visually represents to a user the separation between the genotypes in the class of known genotypes, as the user can visually see the extent to which the clusters of points are separated from one another and distinct in their placement on the graph.

Referring back to FIG. 1B, in an aspect of the present invention, at least two reduced-dimensional correlation vectors for a known genotype may be compiled into a parameter matrix V for the known genotype, which is shown as step 134. Preferably, all correlation vectors for a known genotype are compiled into the parameter matrix for the known genotype, i.e. if $N_k$ dynamic profiles of a particular $k^{th}$ genotype are averaged together to generate the average dynamic profile for the particular genotype, and each dynamic profile has a correlation vector associated with it, then the parameter matrix V should include n correlation vectors. This may be expressed mathematically as follows:

$$V_k = [v_1 v_2 \ldots v_{N_l}]$$

where $V_k$ is the parameter matrix for the kth genotype in the class of genotypes, and $N_l$ is the number of dynamic profiles of the kth genotype used in generating the plot. In this embodiment, the dimensions of $V_k$ are $[(N_g-h) \times N_l]$. For this embodiment, each row is one coordinate of the reduced-dimensional correlation vector, and each column is a reduced-dimensional correlation vector for a dynamic profile of a known genotype with reference to the average normalized profile of each known genotype in the class of known genotypes.

In another aspect of the present invention, the parameter matrix V for a known genotype is used to generate a mean vector $\mu_k$ for each known genotype, as is shown in step 136 in FIG. 1B. The elements of the mean vector $\mu_k$ include the averages of each row of the parameter matrix $V_k$ for the kth genotype. Further, in step 136, the covariance matrix $C_k$ of the parameter matrix $V_k$ may be calculated for each known genotype. The covariance matrix for the kth genotype, $C_k$, may be a square matrix whose elements are calculated as follows:

$$C_k(i, j) = \frac{\sum_{m=1}^{N_l} [(V_k(i, m) - \mu_k(i))(V_k(j, m) - \mu_k(j))]}{N_k - 1}$$

where $N_l$ is the number of dynamic profiles compiled to make up the average profile of the $k^{th}$ genotype. In this embodiment, $C_k$ is an $[(N_g-h) \times (N_g-h)]$ matrix.

Figure 9:
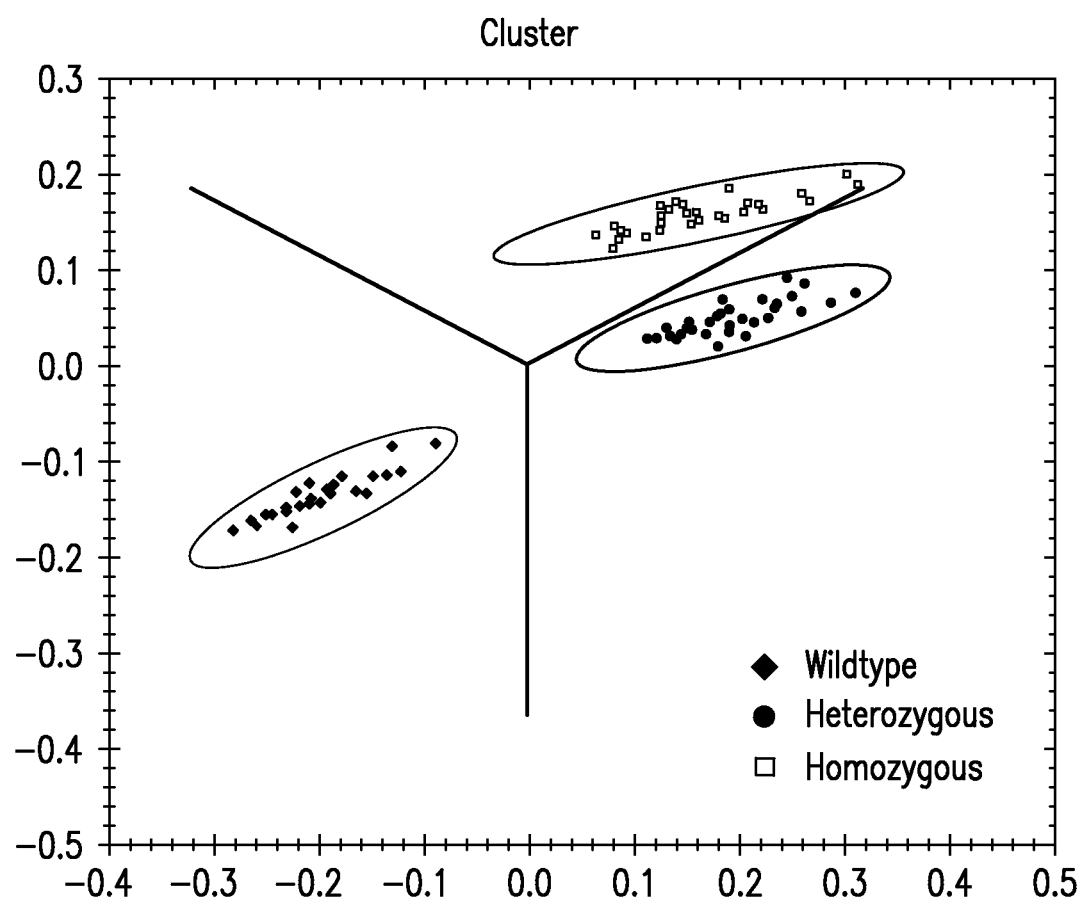
FIG. 9 illustrates a plot of n-ellipses that each contain three standard deviations of the two-dimensional data points representing the dynamic profiles, with one n-ellipse for each genotype.

A further embodiment of the invention involves plotting an n-ellipse around each cluster of reduced-dimensional data points or reduced-dimensional correlation vectors in the plot, as is referred to in step 142 of FIG. 1B. An n-ellipse is an ellipsoid in n-space—e.g. a 2-ellipse will be an ellipse, while a 3-ellipse will be an ellipsoid, a 4-ellipse will be a hyperellipsoid, etc. Each n-ellipse represents the distribution of points for each genotype, and is indicative of the probability that a particular data point v will be classified as the genotype $g_i$, or the class-conditional density $p(v|g_i)$. The class conditional density for a particular data point may be calculated using the following formula:

$$p(v \mid g_i) = \exp\left(-\frac{1}{2}(v-\mu_i)^T (C_i)^{-1}(v-\mu_i) - \frac{d}{2}\log(2\pi) - \frac{1}{2}\log(|C_i|)\right)$$

wherein $|C_i|$ is the determinant of the covariance matrix, and d is the number of dimensions of the covariance matrix (e.g., in the case where the reduced-dimensional data points are two-dimensional, the covariance matrix will be a $[2 \times 2]$ matrix, and d will thus be 2). In a non-limiting example, FIG. 9 shows two-dimensional ellipses for the MTHFR 667 single-nucleotide polymorphism that are appropriately scaled to encompass each cluster of points for each genotype.

Referring back to FIG. 1B, the n-ellipses may be dimensioned in steps 138 and 140 of FIG. 1B. In step 138, the eigenvalues and eigenvectors of each covariance matrix for each genotype within the class of genotypes is calculated. The axes of each n-ellipse are, by definition, perpendicular to each other. The orientation of the n-ellipse for the kth genotype, or its rotation angle relative to the horizontal axis, may be determined by the eigenvectors of $C_k$. The magnitude of the corresponding eigenvalues of $C_k$ may be the variance of the data along the eigenvector directions. Thus, the lengths of the axes of the n-ellipse for a known genotype may be calculated from the eigenvalues of the covariance matrix for that known genotype scaled by a number of standard deviations of the cluster of points a user wishes to cover in these directions.

In one embodiment, the eigenvalues of $C_k$ may be represented as $\lambda_1$ and $\lambda_2$, where $\lambda_1 \leq \lambda_2$. The corresponding eigenvectors are represented as $s_1$ and $s_2$. In the case where $C_k$ is a $[2 \times 2]$ matrix, each eigenvector will have two components; in the case where $C_k$ is a $[3 \times 3]$ matrix, each eigenvector will have three components, and so on. In the two-dimensional case, each eigenvector may have an x and a y component and may be represented as the following vectors:

$$s_1 = \begin{bmatrix} s_{1x} \\ s_{1y} \end{bmatrix}, s_2 = \begin{bmatrix} s_{2x} \\ s_{2y} \end{bmatrix}$$

The rotation angle $\theta_k$ of the ellipse for the kth genotype (which may be the angle the major axis of the n-ellipse (in this case, an ellipse) makes with the horizontal) may be given by the inverse tangent of the ratio of the y component to the x component of the eigenvector corresponding to the larger eigenvalue:

$$\theta_k = \tan^{-1}\left(\frac{s_{2y}}{s_{2x}}\right)$$

The eigenvalues $\lambda_1$ and $\lambda_2$ are the variances of the cluster distribution along the minor and major axes respectively of the ellipse. In order for a two-dimensional ellipse to cover ±n standard deviations of the distribution of the cluster of points for a particular genotype, half the length of the major axis $l_M$ may be calculated from the following formula:

$$\frac{l_M}{2} = n\sqrt{\lambda_2}$$

and the half-length of the minor axis $l_m$ may be calculated from the smaller eigenvalue $$\frac{l_m}{2} = n\sqrt{\lambda_1}$$

Figure 10:
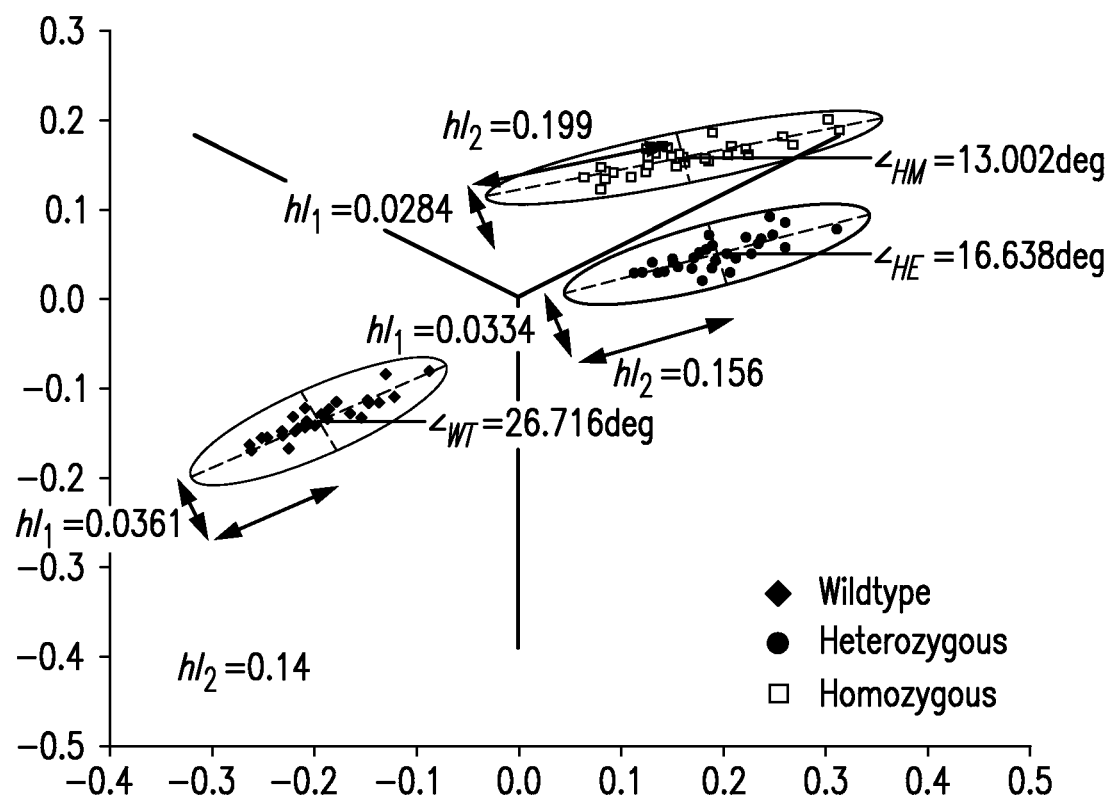
FIG. 10 illustrates the plot of FIG. 9 showing the computation of the major/minor axis widths of the n-ellipses and the rotation angle of each n-ellipse.
Figure 11:
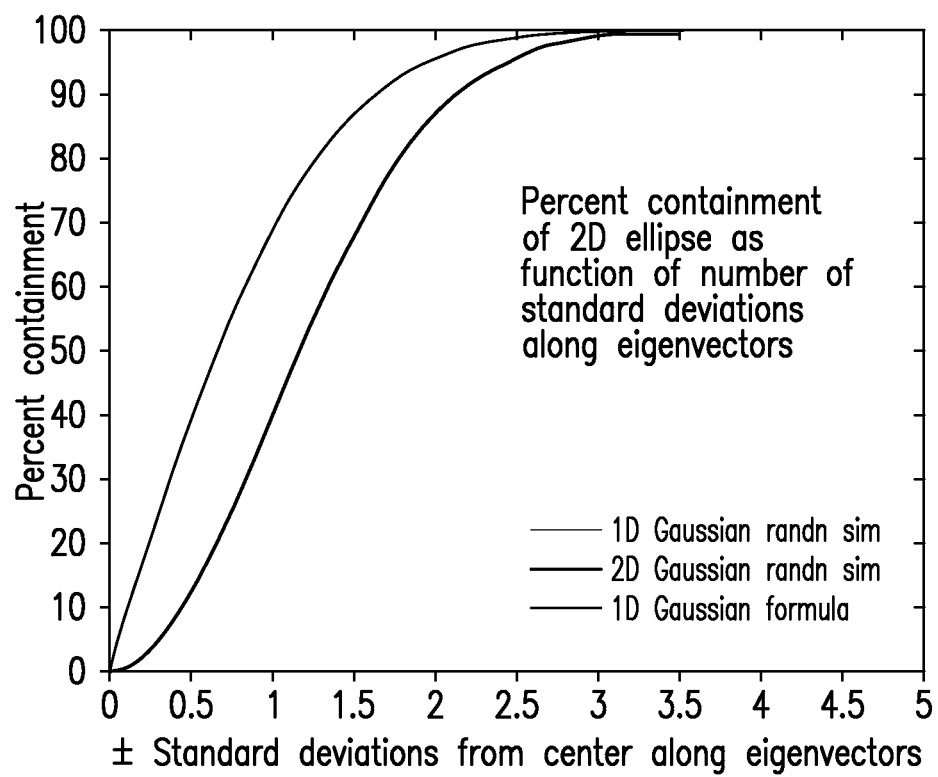
FIG. 11 illustrates a graph showing the percentage of points contained an n-ellipse versus the number of standard deviations of the distribution covered by the ellipse.

Referring back to FIG. 1B, in one embodiment, a user may be able to input the number of standard deviations for the n-ellipse to cover in step 144. For example, FIG. 10 shows the ellipses for each genotype of the MTHFR 667 single-nucleotide polymorphism with representations of the properly calculated rotation angles and major/minor axis widths to cover three standard deviations of each individual cluster. However, in one embodiment, the user may not input the number of standard deviations for the ellipse to cover, but instead may input the percentage of the number of points the user wishes the n-ellipse to cover. For a normally distributed cluster of points, the percentage of points covered by an ellipse will bear a functional relationship to a scaling factor times the number of standard deviations covered by the ellipse. By the user choosing a percentage of points to be covered by the ellipse, the scaling factor n for the ellipse can be calculated, and thus the ellipse can cover a predetermined percentage of the points in the cluster. FIG. 11 shows the functional relationship between the number of standard deviations covered by the ellipse and the percentage of normally distributed points that are covered in the two-dimensional case.

In another aspect, the present invention provides a method of determining the identity of the genotype of an unknown nucleic acid (also referred to as unknown genotype) present in a biological sample. In accordance with one embodiment, an unknown genotype is determined by using the following steps: using the computer to convert a dynamic profile of an unknown genotype of a nucleic acid to a multi-dimensional data point representing the unknown genotype, using the computer to transform the multi-dimensional data point representing the unknown genotype into a reduced-dimensional data point representing the unknown genotype, plotting the reduced-dimensional data point representing the unknown genotype on the plot; and identifying the unknown genotype.

FIGS. 1A-B also illustrates this embodiment of the invention. In step 146, a dynamic profile y(x) of an unknown genotype contained in a biological sample is generated. The dynamic profile may be generated by any of the methods described herein. The dynamic profile contains measurements of a signal, y(t), which represents a physical change of a nucleic acid containing the known genotype. These measurements of the signal are recorded relative to an independent variable, x(t). These measurements are input into the method in step 148. Depending on how the dynamic profile is generated, y(t) and x(t) may be different physical quantities. For example, in the embodiment where the dynamic profile is generated through thermal melting of a nucleic acid containing the known genotype with intercalating dyes, x(t) is the temperature T(t), and y(t) is the fluorescence, F(t), or the derivative of the fluorescence relative to temperature, –dF/dT. In the embodiment where the dynamic profile is generated through voltammetry of a nucleic acid with a redox-active molecule, x(t) is the electric potential V(t) and y(t) is the electric current I(t).

In step 150, an associated positive control dynamic profile of a control genotype is also generated at the same time the dynamic profile of the unknown genotype is generated. The associated positive control dynamic profile of the positive control genotype is also comprised of measurements of the same signal relative to the same independent variable as the dynamic profile, though the measurements are taken from a positive control sample rather than the sample containing the unknown genotype. In step 152, the positive control dynamic profile is compared to a standard reference dynamic profile for the control genotype. This is done to generate a shift value $\Delta x$ for the independent variable, and this step is performed in the same manner as was done when determining the shift value $\Delta x$ in step 108. The standard reference dynamic profile of the positive control genotype may be the standard reference dynamic profile generated in step 122.

In order to generate the shift value $\Delta x$ as well as a scaling factor $\alpha$, the independent variable in a positive control profile $y_p(x)$ or dynamic profile is shifted by the shift value $\Delta x$ to generate a shifted profile $y_p'(x)$:

$$y_p'(x) = \alpha * y_p(x - \Delta x)$$

Each of the shifted positive control profiles $y_p'(x)$ are then correlated to the known positive control profile $y_{rs}(x)$ to generate a correlation coefficient r. The correlation coefficient of a dynamic profile $y_1(x)$ against $y_2(x)$ may be calculated as described above.

In step 154, the independent variable in the dynamic profile of the unknown genotype is shifted by the shift value $\Delta x$. The dynamic profile for the unknown genotype may also be scaled by the scaling factor $\alpha$. All dynamic profiles taken from the same experiment that is associated with a positive control may be shifted and scaled by the same amount, i.e. if more than one dynamic profile of an unknown genotype is generated in a single experiment, only one positive control dynamic profile need be generated, and only one shift value $\Delta x$ need be determined. This shifting and scaling procedure minimizes the variability in the independent variable from one experiment to the next, in order to make sure that results are consistent and reproducible.

In step 156, the dynamic profile of the unknown genotype is normalized to have a predetermined standard deviation. It is also possible to normalize the dynamic profile of the unknown genotype to have a predetermined mean and a predetermined standard deviation. In one embodiment, the dynamic profile of the unknown genotype is normalized to have the same predetermined standard deviation and/or mean as the dynamic profiles of the known genotypes used to generate any average profiles for known genotypes to which the dynamic profile for the unknown genotype will be compared.

In step 158, the dynamic profile is correlated to each one of the average dynamic profiles for each known genotype in the class of genotypes generated in 116 in order to obtain correlation values for each known genotype. In some embodiments, this correlation value may be the average sum squared error between the dynamic profile for the unknown genotype and the average dynamic profile for the known genotype, the correlation coefficient between the dynamic profile for the unknown genotype and the average dynamic profile for the known genotype, or a posterior probability that the unknown genotype is the genotype represented in an average dynamic profile for a known genotype. The correlation coefficient and the sum squared error may be calculated in a manner identical to that used for calculating correlation coefficients and sum squared error in the method of generating the training set. In order to maximize the separation between genotypes, a separation-maximizing independent variable range may be input in step 160. This separation-maximizing range may be calculated using, for example, the Enhanced Monte-Carlo Method disclosed later in this application, or through maximization of the ratio of the between-class scatter to within-class scatter, as disclosed in U.S. patent application Ser. No. 12/759,415.

Mathematically, the correlation value of the dynamic profile containing the unknown genotype against the average dynamic profile for the known genotype that generates the largest value should indicate that the unknown genotype is that known genotype. Likewise, the average dynamic profile for a known genotype that generates the lowest average sum squared error between the dynamic profile for the unknown genotype and the average dynamic profile for the known genotype should indicate that the unknown genotype is that known genotype.

However, investigators may desire a visual, rather than solely quantitative, representation of a genotype call. In one embodiment of the invention, a correlation vector r is calculated for the unknown genotype. In one embodiment, the correlation vector r is a vector with dimensions $[N_g \times 1]$ that includes in its elements a correlation coefficient between the dynamic profile of the unknown genotype and each of the average dynamic profiles of a known genotype within the class of genotypes as generated in 158. Alternatively, the correlation coefficients may be the average sum squared error between the dynamic profile of the unknown genotype and the average dynamic profile of each known genotype within the class of genotypes.

The correlation vector r may then be transformed into a reduced-dimensional correlation vector in step 130 using a transformation matrix, in a manner substantially identical to transforming the correlation vectors for the known genotypes in 128. The correlation vector for the unknown genotype may then be plotted on the same plot generated in step 132. An investigator can then identify the genotype to which the unknown reduced-dimensional correlation vector corresponds either by determining that it falls in the sector demarcated by the axes on the plot that corresponds to a particular genotype (see FIG. 8), or by determining that the unknown reduced-dimensional correlation vector falls within one of the ellipses generated on the plot (see FIG. 9).

In another aspect of the invention, a system and method for calculating an error statistic for an assay is provided. While the method for plotting the clusters of genotypes provides one way in which an investigator may qualitatively examine the separation between various genotype clusters and their dynamic profiles, it is useful to have some quantification of the actual overall misclassification rate for an assay, as well as misclassification rates for each individual genotype in a class of genotypes, as well as the probability that a sample containing one genotype will be misclassified as each of the other incorrect genotypes.

Figure 12A:
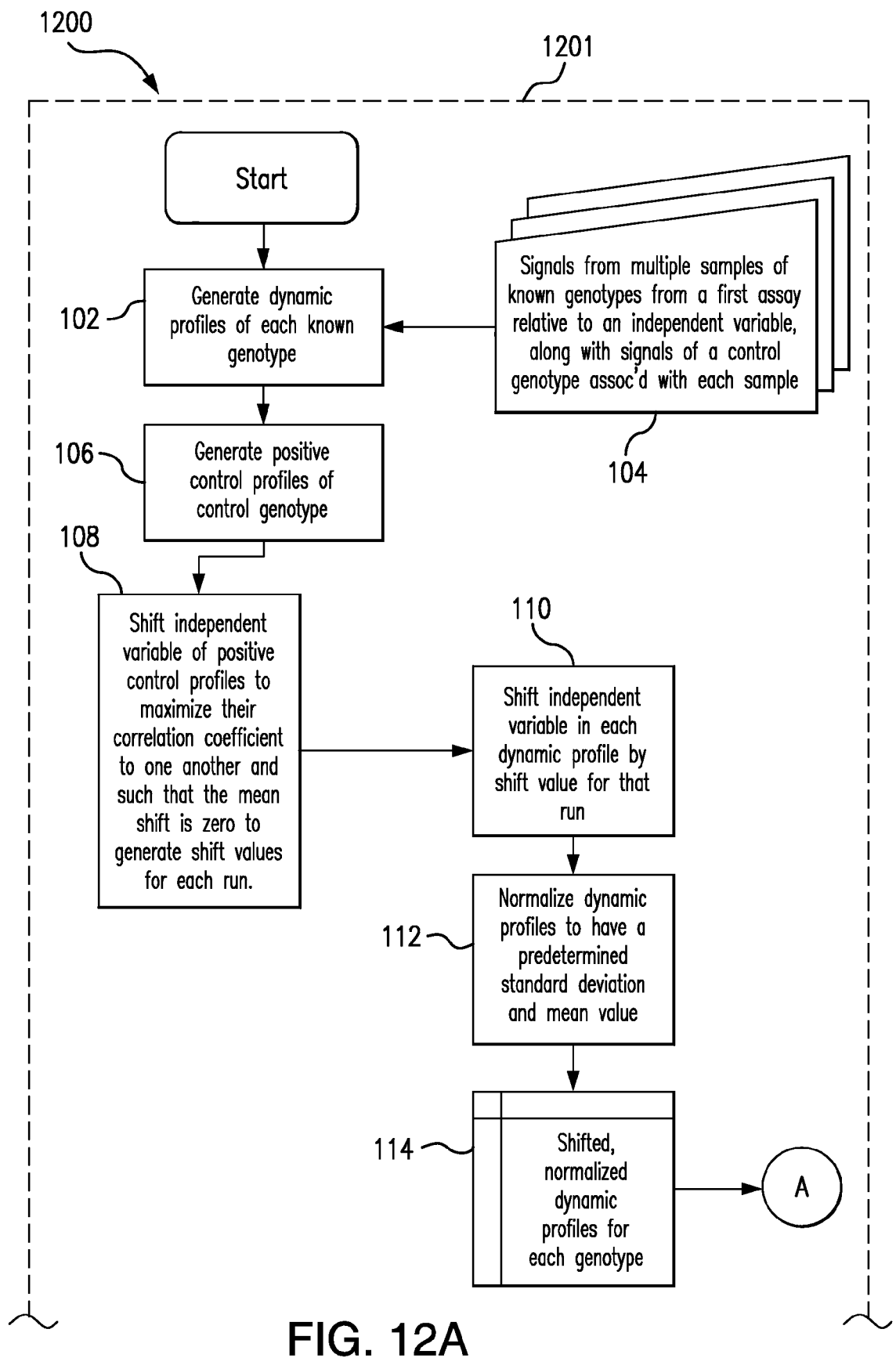
FIGS. 12A-C illustrate a flowchart showing one embodiment of a method of calculating an overall expected misclassification rate for an assay for identifying a genotype in a biological sample.
Figure 12B:
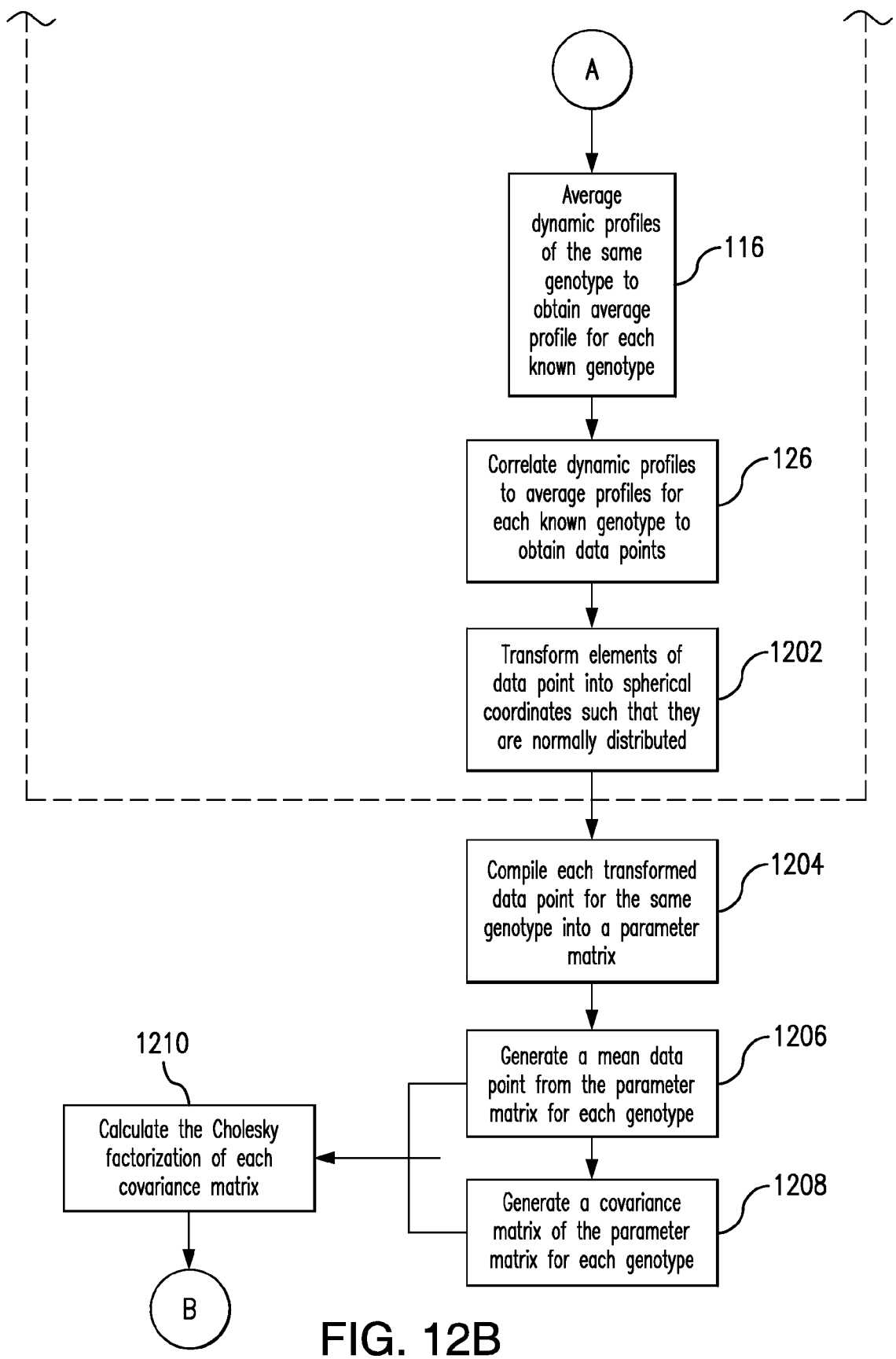
Figure 12C:
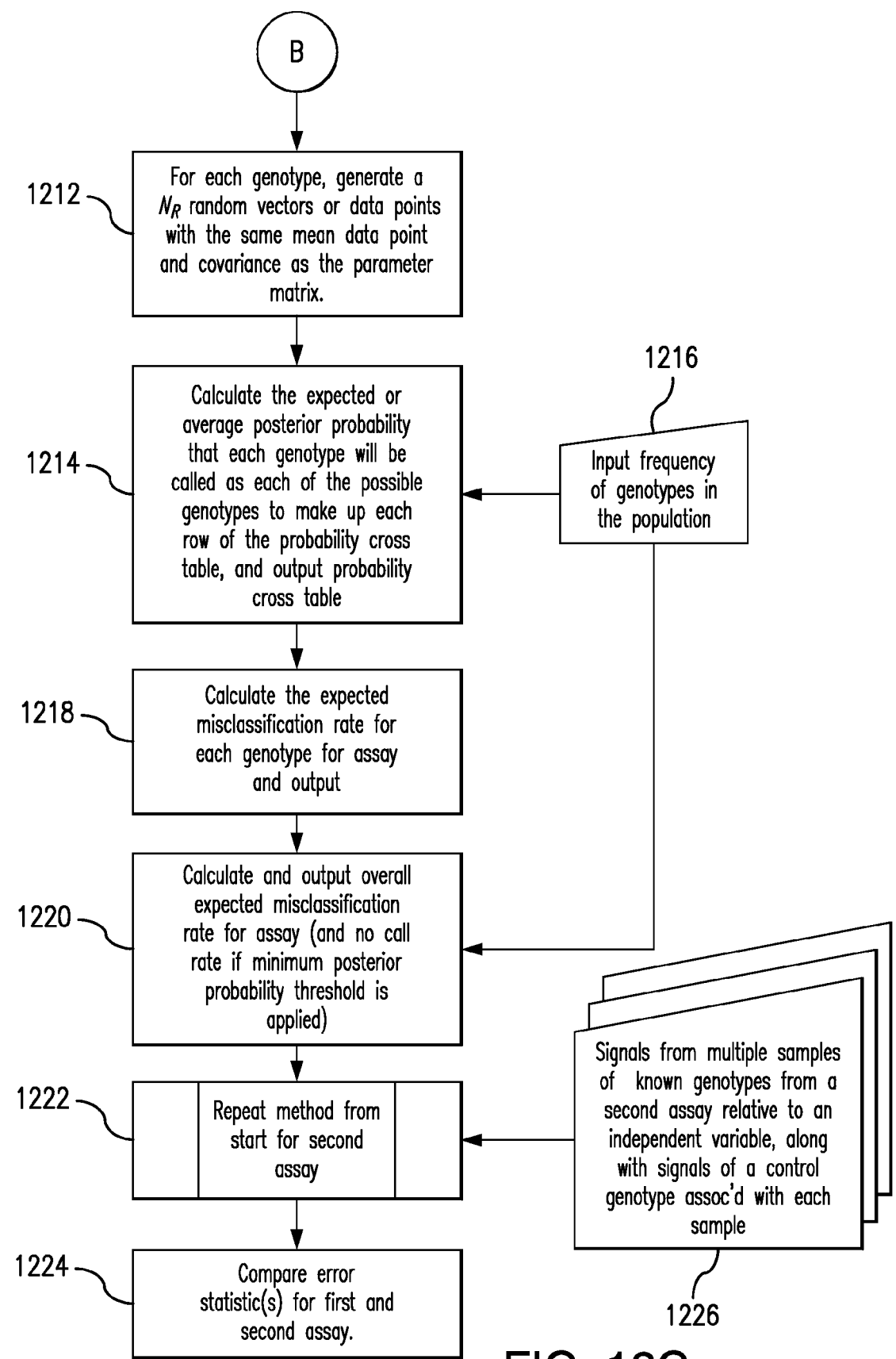

A method for calculating an error statistic is described in FIGS. 12A-C in accordance with one exemplary embodiment of the present invention. Method 1200 of FIGS. 12A-B may include a method by which dynamic profiles are converted to data points. In one embodiment, this step is a submethod, which is shown as submethod 1201, that may incorporate the steps shown as surrounded by the dashed box in FIG. 12A-B. One of ordinary skill in the art, of course, will appreciate that this is a non-limiting example of such a method, and various other methods exist for generating data points from dynamic profiles. Other non-limiting examples of such methods include selecting certain values from the dynamic profile (such as melting temperature, enthalpy of melting, and peak fluorescence) as the elements of a data point, or through principle component analysis, or other statistical methods.

Steps 102 through 126 of FIG. 12A are similar to steps 102 through 126 described above in connection with FIGS. 1A and 1B, and thus are identified with the same numbers. In step 102 of submethod 1201, dynamic profiles of each known genotype are generated by inputting signals from multiple samples of each known genotype in a class of known genotypes in order to generate dynamic profiles of each known genotype from an assay. Along with each dynamic profile, a positive control profile of the known genotype is generated in step 106. The independent variable of each dynamic profile is shifted by a shift value generated for that run in step 110; that shift value is generated in step 108. The dynamic profiles of the known genotypes are then normalized in step 112 such that they have a predetermined standard deviation and mean value, and are then grouped together by genotype and averaged in step 116 to generate an average profile for each known genotype. In step 126, each dynamic profile is then correlated to each of the average profiles for the known genotypes in the class of known genotypes in order to generate a correlation vector r (which may be a data point) for each dynamic profile. The elements of the correlation vectors may be correlation values of the dynamic profile against each average profile of a known genotype within the class of genotypes. Again, this correlation value may be the average sum squared error between the dynamic profile for the unknown genotype and the average dynamic profile for the known genotype, the correlation coefficient between the dynamic profile for the unknown genotype and the average dynamic profile for the known genotype, or a posterior probability that the unknown genotype is the genotype represented in an average dynamic profile for a known genotype. Correlation coefficients are preferred, and the method of calculating such a correlation coefficient is disclosed earlier in this application.

Figure 13:
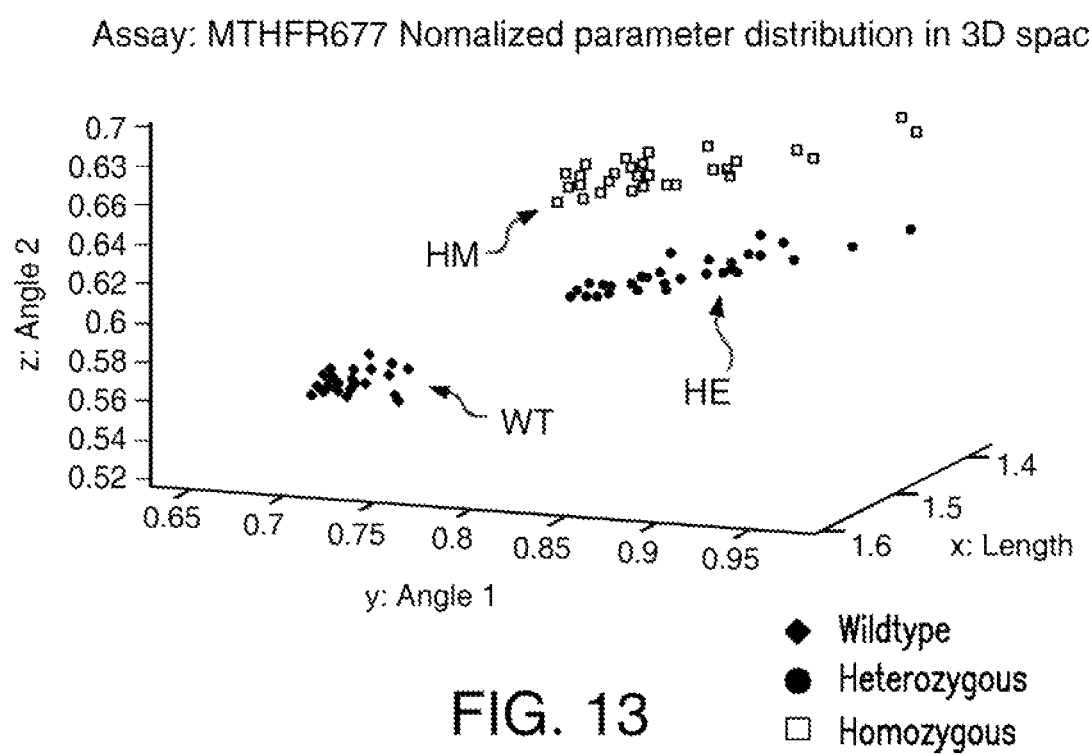
FIG. 13 illustrates the three-dimensional data points of FIG. 6 in which the three-dimensional data points have been translated into spherical coordinates and are normally distributed.

The correlation vectors r generated in step 126 of submethod 1201 are not normally distributed, within their respective genotypes. In order to obtain a normal distribution, one may transform the correlation vectors r into transformed correlation vectors v by translating the elements of each correlation vector r into n-spherical coordinates, which causes the elements of the correlation vector to fall within a normal (or Gaussian) distribution, as is shown in step 1202. In a non-limiting example, FIG. 13 shows the set of correlation vectors for the wild-type, heterozygous, and homozygous mutant populations of the MTHFR 667 class of genotypes, after translation to spherical coordinates, and also the normal distribution of those points.

For a class of genotypes with three possible genotypes (e.g., wild-type (WT), heterozygous (HE), and homozygous mutant (HM)) the elements of the transformed correlation vector v may be calculated from the elements of the correlation vector r as follows:

$$r = \begin{bmatrix} r_{wt} \\ r_{he} \\ r_{hm} \end{bmatrix}$$

$$l = \sqrt{r_{wt}^2 + r_{he}^2 + r_{hm}^2}$$

$$a_1 = \tan^{-1}\left(\frac{r_{he}}{r_{wt}}\right)$$

$$a_2 = \tan^{-1}\left(\frac{r_{hm}}{\sqrt{(r_{wt})^2 + (r_{he})^2}}\right)$$

$$\text{Transformed vector } v = \begin{bmatrix} l \\ a_1 \\ a_2 \end{bmatrix}$$

wherein $r_{wt}$ is the correlation vector of the dynamic profile against the average profile for the wild-type genotype, $r_{he}$ is the correlation vector of the dynamic profile against the average profile for the heterozygous genotype, and $r_{hm}$, is the correlation vector of the dynamic profile against the average profile for the homozygous mutant genotype. In some embodiments, if the number of possible genotypes or dimensions $N_g$ is greater than 3, this transformation can be extended as follows:

$$l = \sqrt{r_1^2 + r_2^2 + r_3^2 + r_4^2}$$

$$a_1 = \tan^{-1}\left(\frac{r_2}{r_1}\right)$$

$$a_2 = \tan^{-1}\left(\frac{r_3}{\sqrt{(r_1)^2 + (r_2)^2}}\right)$$

$$a_3 = \tan^{-1}\left(\frac{r_4}{\sqrt{(r_1)^2 + (r_2)^2 + (r_3)^2}}\right)$$

$$\text{Transformed vector: } v = \begin{bmatrix} l \\ a_1 \\ a_2 \\ a_3 \end{bmatrix}$$

where $r_1$, $r_2$, $r_3$ and $r_4$ are the correlation coefficients of the dynamic profile against the average normalized value for the first, second, third, and fourth genotypes, respectively. This pattern can be extended further for other embodiments in which $N_g$ is greater than 4.

The transformed correlation vectors v may then be compiled into the parameter matrix for the known genotype in step 1204. In one embodiment, all correlation vectors for a known genotype are compiled into the parameter matrix for the known genotype, i.e. if $N_k$ dynamic profiles of a particular $k^{th}$ genotype are averaged together to generate the average dynamic profile for the particular genotype, and each dynamic profile has a correlation vector associated with it, then the parameter matrix V should include n correlation vectors. This may be expressed mathematically as follows:

$$V_k = [v_1 v_2 \ldots v_{N_l}]$$

where $V_k$ is the parameter matrix for the kth genotype in the class of genotypes, and $N_l$ is the number of dynamic profiles of the kth genotype used in generating the plot. In this embodiment, the dimensions of $V_k$ are $[N_g \times N_l]$, where $N_g$ is the number of genotypes in the class of known genotypes. For this embodiment, each row is one coordinate of the transformed correlation vector across all the correlation vectors, and each column is a transformed correlation vector for a dynamic profile of a known genotype.

In another aspect of the present invention, the parameter matrix $V_k$ for a known genotype is used to generate a data point or vector $\mu_k$ for each known genotype, as is shown in step 1206 in FIG. 12B. The elements of the mean vector or data point $\mu_k$ may include the averages of each row of the parameter matrix $V_k$ for the kth genotype. Further, in step 1208, the covariance matrix $C_k$ of the parameter matrix $V_k$ may be calculated for each known genotype. The covariance matrix for the kth genotype, $C_k$, is a square matrix whose elements are calculated as follows:

$$C_k(i, j) = \frac{\sum_{m=1}^{N_l} [(V_k(i, m) - \mu_k(i))(V_k(j, m) - \mu_k(j))]}{N_k - 1}$$

where $N_l$ is the number of dynamic profiles compiled to make up the average profile of the $k^{th}$ genotype. In this embodiment, $C_k$ may be an $[N_g \times N_g]$ matrix.

Using the covariance matrix, it is possible to calculate the class conditional density $p(v|g_i)$, which represents the probability that correlating a dynamic profile of a first known genotype to an average normalized dynamic profile for a first known genotype would generate the transformed correlation vector v. The class conditional probability that a known genotype $g_i$ would generate the correlation vector v may be calculated from the mean vector $\mu_i$ and the covariance matrix $C_i$ for that known genotype by using the following formula:

$$p(v \mid g_i) = \exp\left(-\frac{1}{2}(v - \mu_i)^T (C_i)^{-1}(v - \mu_i) - \frac{N_g}{2}\log(2\pi) - \frac{1}{2}\log(|C_i|)\right)$$

wherein $|C_i|$ is the determinant of the covariance matrix, and $N_g$ is the number of genotypes that make up all of the possible mutations.

If the occurrence of each possible genotype in the class of genotypes were equally likely in the population, then the unknown genotype could be identified as the genotype with the largest class-conditional density with a great degree of confidence. Using the frequency of the known genotypes in the population, it is possible to calculate a posterior probability that a particular dynamic profile corresponds to a known genotype. The user may input the frequency of the known genotype $P(g_i)$ into the algorithm, and Bayes's Theorem, for example, may be used to calculate the posterior probability $p(g_i|v)$ that the unknown sample is the known genotype:

$$p(g_i \mid v) = \frac{P(g_i) \cdot p(v \mid g_i)}{\sum_{i=1}^{N_g} (P(g_i) \cdot p(v \mid g_i))}$$

For example, a data point $v_{WT1}$ representing a wild-type dynamic profile may generate the following posterior probability values based on a set of points for the wild-type genotype:

$$p(g_{WT}|v_{WT1})=0.995 \; p(g_{HE}|v_{WT1})=0.003 \; p(g_{HM}|v_{WT1})=0.002$$

Based on the set of wild-type points, 99.5% of the time, the sample represented by the dynamic profile that generated this data point should be identified as a wild-type curve, identified as heterozygous 0.3% of the time, and identified as homozygous mutant 0.2% of the time.

If another data point $v_{WT2}$ representing a wild-type dynamic profile generated the following posterior probability values based on a set of points for the wild-type genotype:

$$p(g_{WT}|v_{WT2})=0.997 \; p(g_{HE}|V_{WT2})=0.002 \; p(g_{HM}|v_{WT2})=0.001$$

then 99.7% of the times this dynamic profile was obtained, the sample represented by the dynamic profile that generated this data point would be identified as a wild-type curve, identified as heterozygous 0.2% of the time, and identified as homozygous mutant 0.1% of the time.

By repeatedly sampling points representing dynamic profiles of the wild-type genotype, and calculating the posterior probabilities for those points so that they may represent each of the possible genotypes, one may generate expected posterior probability values that a point representing a wild-type genotype will be identified as each of the possible known genotypes, as set forth in step 1214 of FIG. 12C. These expected posterior probability values are the average of the posterior probabilities for each point in the data set. By repeating the same process for each other known genotype, one may generate a probability cross table, as shown in Table 1:

TABLE 1

Probability Cross table

| Known Genotype (rows) | Called Genotype (columns) | | |
|---|---|---|---|
| | Wildtype | Heterozygous | Homozygous |
| Wildtype | $\bar{p}(g_{WT} \mid v_{WT})$ | $\bar{p}(g_{WT} \mid v_{HE})$ | $\bar{p}(g_{WT} \mid v_{HM})$ |
| Heterozygous | $\bar{p}(g_{HE} \mid v_{WT})$ | $\bar{p}(g_{HE} \mid v_{HE})$ | $\bar{p}(g_{HE} \mid v_{HM})$ |
| Homozygous | $\bar{p}(g_{HM} \mid v_{WT})$ | $\bar{p}(g_{HM} \mid v_{HE})$ | $\bar{p}(g_{HM} \mid v_{HM})$ |

Ideally, the diagonal elements of the probability cross table should have values of one, and the off-diagonal elements of the probability cross table should have values of zero, as this would mean there was no possibility of any single dynamic profile representing a genotype being misidentified as another genotype.

Using the off-diagonal elements of the cross-probability table, it is possible to calculate an expected misclassification rate for each genotype, as set forth in step 1218:

$$e_{WT} = \bar{p}(g_{WT}|v_{HE}) + \bar{p}(g_{WT}|v_{HM})$$

$$e_{HE} = \bar{p}(g_{HE}|v_{WT}) + \bar{p}(g_{HE}|v_{HM})$$

$$e_{HM} = \bar{p}(g_{HM}|v_{WT}) + \bar{p}(g_{HM}|v_{HE})$$

If all of the points used to calculate the expected misclassification rates for each genotype are generated in the same assay, having nearly identical assay parameters, it is possible to generate an overall misclassification rate for the assay by summing the expected misclassification rate for each possible genotype in step 1220 by inputting the population frequencies 1216 and calculating the overall misclassification rate through the following formula:

$$e = P_{WT}e_{WT} + P_{HE}e_{HE} + P_{HM}e_{HM}$$

wherein $P_{WT}$, $P_{HE}$, and $P_{HM}$ are the probabilities of the wild-type, heterozygous, and homozygous genotypes in the overall population.

One of ordinary skill will appreciate that this calculation for an overall misclassification rate can be carried out for assays for nucleic acids that may potentially have more or fewer than three possible genotypes. In a four-genotype case, for example, the probability cross table would have four rows and four columns, and the expected misclassification rate for each genotype would be the sum of the three off-diagonal elements of the probability cross-table for each genotype.

In accordance with one embodiment, an error statistic for the assay may be calculated through this method. In one embodiment, the error statistic may be the posterior probability that a dynamic profile representing a known genotype will be identified as any one of the possible known genotypes. In an alternate embodiment, the error statistic may be the expected misclassification rate for a particular genotype. In yet another alternate embodiment, the error statistic may be the overall misclassification rate for the assay.

It is important to note that the greater number of data points used in calculating the posterior probabilities in the probability cross table, the more accurate the elements of the probability cross table will be, and thus the more accurate the expected misclassification rates and overall expected misclassification rate will be. The sampled points for a particular genotype can be obtained from the dynamic profiles used to generate the average dynamic profiles of the known genotype. For example, one can calculate the posterior probabilities in the first row of Table 1 ($\bar{p}(g_{WT}|v_{WT})$, $\bar{p}(g_{WT}|v_{HE})$, and $\bar{p}(g_{WT}|v_{HM})$) by calculating posterior probabilities for each wild-type data point using the covariance matrix and mean data point for each of the other two genotypes. In this case, however, the accuracy of the posterior probabilities is limited by the number of wild-type data points available. Since one run of an assay on a biological sample containing the wild-type genotype may only generate one point for the wild-type genotype, the accuracy of the misclassification rates for the assay, the accuracy of an error statistic may be limited by the number of runs.

It is possible, however, to estimate a more accurate misclassification rate through use of an enhanced Monte Carlo simulation. One embodiment of the invention comprises using this enhanced Monte Carlo simulation to generate an error statistic for an assay. Monte Carlo simulations, in general, are a class of computational algorithms that rely on repeated random sampling to compute their results. In an embodiment of the present invention, N random points may be generated such that the random points have a mean data point and covariance matrix identical to one of the known genotypes. Because these N simulated random points have the same distribution as the points generated experimentally, they can be used to further refine the error statistic for the assay.

For example, referring back to FIG. 12C, in step 1212, $N_R$ random vectors/data points may be generated for each known genotype. In one embodiment, the $N_R$ random points for a known genotype can be generated in the following manner. First, the covariance matrix $C_i$ for the known genotype may be reduced to a Cholesky factorization L in step 1210. If the covariance matrix $C_i$ is an $[N_g \times N_g]$ matrix, the Cholesky factorization L is an $[N_g \times N_g]$ lower-triangular matrix defined by the following equation:

$$LL^T = C_i$$

In the case where there are three genotypes, L is a [3×3] matrix with the following elements:

$$L = \begin{bmatrix} L_{1,1} & 0 & 0 \\ L_{2,1} & L_{2,2} & 0 \\ L_{3,1} & L_{3,2} & L_{3,3} \end{bmatrix}$$

In one embodiment, the elements $L_{a,b}$ of the Cholesky factorization L may be calculated from any symmetric, positive-definite matrix D with elements $D_{a,b}$ by using a nested loop using the following two equations:

$$L_{a,b} = \frac{1}{L_{b,b}} \left( D_{a,b} - \sum_{k=1}^{b-1} L_{a,k} L_{b,k} \right)$$

(for a>b, where a is the row and b is the column)

$$L_{a,a} = \sqrt{D_{a,a} - \sum_{k=1}^{a-1} L_{a,k}^2}$$

In one embodiment, to generate $N_R$ random data points with the same mean data point $\mu_i$ and covariance matrix $C_i$ as the ith genotype, one may repeatedly calculate random data points using the following equation:

$$v_{i,j} = L_i * \text{randn}(N_g, 1) + \mu_i$$

For each ith genotype, j can go from 1 to $N_R$ number of times to create any $N_R$ data points that have the same distribution as the genotype cluster for the ith genotype. The function randn $(N_g, 1)$ generates an [3×1] data point or vector whereby, when sampled multiple times, each element has a mean of zero and standard deviation of 1. $L_i$ is the Cholesky factorization of the covariance matrix for the ith genotype $C_i$. Multiplying the random vector times the Cholesky factorization $L_i$ results in a distribution of points with the same covariance matrix as the set of points for the ith genotype, while adding the mean data point or vector $\mu_i$ results in that distribution of randomly generated points being centered around the mean data point as the data points representing the experimental runs for the ith genotype. Thus, the set of data points generated has the same mean position as the cluster of points generated experimentally.

By repeating this process for each genotype in the class of known genotypes, it is possible to generate a set of $N_R$ random data points for each known genotype. These $N_R$ data points can be used to achieve a more accurate expected probability cross table, expected misclassification rate, and overall misclassification rate than merely using experimentally obtained data points alone. These values, of course, are calculated either by using the $N_R$ random data points alone for each genotype to generate the probability cross table of Table 1, or by calculating the values in the probability cross table using the $N_R$ randomly generated data points for each genotype in combination with the experimentally generated data points for each genotype. The procedure described by this invention may allow an investigator to quantify the degree of overlap or separation between any two genotype clusters of data points into a theoretical expected misclassification rate.

By generating these error statistics, an investigator is able to determine the level of confidence possible for a "call" of a particular genotype from a genotyping analysis system without using a predetermined "no-call" threshold. This is known as "forcing a call." However, using the enhanced Monte Carlo technique for generating $N_R$ random data points as described herein, it is further possible to evaluate the effect of including a "no-call" posterior probability threshold (i.e., if the largest posterior probability for a data point representing a dynamic profile is less than the no-call threshold, it would be classified as a "no call") on various error statistics in the system. In one embodiment, using the methods and systems described in U.S. patent application Ser. No. 12/759,415 to identify an unknown genotype, after generating a dynamic profile for a sample containing an unknown genotype and reducing that dynamic profile to a data point or vector, the posterior probability that the sample contains each one of the possible known genotypes can be calculated using the methods for calculating the posterior probabilities disclosed therein. If none of the posterior probabilities is greater than a threshold value, no call is made. If the posterior probability is greater than the threshold value, then the unknown genotype may be "called" as the known genotype.

Including such a "no-call threshold" may actually affect the overall misclassification rate of the system. In one non-limiting example, two data points $v_{WT1}$ and $V_{WT2}$ generate the following posterior probabilities relative to the wild-type (WT), heterozygous (HE), and homozygous genotypes:

$$p(g_{WT}|v_{WT1})=0.995\ p(g_{HE}|v_{WT1})=0.003\ p(g_{HM}|v_{WT1})=0.002$$

$$p(g_{WT}|v_{WT2})=0.997\ p(g_{HE}|v_{WT2})=0.002\ p(g_{HM}|v_{WT2})=0.001$$

In the case where a no-call threshold was set at 99.6%, a call would be made on $v_{WT1}$ but not $V_{WT2}$. The effect of making this "call" is to set the posterior probability for each of the genotypes to zero and to generate a new posterior probability, $p(NC|v_{WT1})$, which represents the probability of a no-call situation. In this case, the posterior probabilities for the two points have the following values:

$$p(g_{WT}|v_{WT1})=0\ p(g_{HE}|v_{WT1})=0\ p(g_{HM}|v_{WT1})=0$$
$$p(NC|v_{WT1})=1$$

$$p(g_{WT}|v_{WT2})=0.997\ p(g_{HE}|v_{WT2})=0.002\ p(g_{HM}|V_{WT2})=0.001\ p(NC|v_{WT2})=0$$

In calculating the expected posterior probabilities for the probability-cross table, "no-call" points are ignored and only points that generate a posterior probability above the no-call threshold are used. This has the effect of increasing the expected posterior probabilities that the genotype will be called correctly, but also has the concomitant effect of reducing the number of data points used in calculating the expected posterior probability, expected misclassification rate for a genotype, or overall misclassification rate. By generating additional data points with the same mean data point and covariance matrix for a known genotype as generated in step 1212, for example, it is possible to estimate these error statistics after a change in the no-call threshold, without reducing the number of data points used in determining the overall misclassification rate.

In one aspect of the present invention, the plotting method disclosed herein may be used to plot the data points generated from the dynamic profiles along with receiving the output error statistic. Combining these two methods allows an user to both visualize the qualitative separation between the genotypes by viewing the data points associated with the genotypes, and by receiving a quantification of the separation between the genotypes in the form of an error statistic.

One useful aspect of calculating error statistics for assays, such as expected posterior probabilities, expected misclassification rate for a genotype, or overall expected misclassification rate for an assay, is being able to compare the quality of two different assays. Several assay parameters, including assay reagents responsible for the amplification of DNA segments that include the mutations of interest, the sensing and control instrumentation (along with the conditions under which they operate), the process by which raw data and dynamic profiles are collected (e.g., imaging systems to monitor fluorescence, temperature sensing, and control systems for collecting thermal melt data), and software (including algorithms embodied in said software) used to identify a genotype can all introduce different errors and/or reduce other errors. However, using current methods, one must collect data through repeated runs of an assay in order to calculate an error statistic. Even then, the quality of the error statistic is limited by the number of runs one has conducted on the assay. As such, provided herein is a method and system for comparing two assays that allows one to reduce the number of runs one needs to perform in order to estimate an error statistic for an assay.

FIGS. 12A-C further illustrate this embodiment of the invention. In this method, either prior to, concurrent to, or after generating the error statistics for an assay (i.e., a first assay), the process may be repeated for a second assay in order to generate error statistics for the second assay in step 1222 by inputting signals from a second assay from multiple samples of known genotypes relative to an independent variable, along with the appropriate signal of a control genotype in step 1226. The error statistics for the first and second assays may then be compared, and the assay with the lower error statistic may be selected as optimal over the other assay in step 1224. The first and second assay may differ in at least one assay parameter or component. Such assay parameters or components may include, for example, reaction components (including assay reagents, DNA primers responsible for the amplification of DNA segments that include the mutations of interest, etc.), assay equipment (e.g., sensing and control instrumentation, along with the conditions under which they operate, reaction vessels, etc.), the measured independent and dependent variable (i.e. fluorescence versus temperature, voltage versus current/resistance, etc.), software (including algorithms embodied in said software).

One assay parameter that may be altered between assays is the independent variable range over which dynamic profile data may be collected. In U.S. patent application Ser. No. 12/759,415, a method for determining a separation maximizing range for the independent variable is disclosed; this method involves calculating the ratio of the determinants of a between-class scatter matrix for a class of genotypes and the within-class scatter matrix of the known genotypes to generate a separation ratio q for a particular $x_{min}$ and $x_{max}$. The separation ratio q is then calculated and recorded for that $x_{min}$ and $x_{max}$. This step is then automated for a wide variety of different $x_{min}$ and $x_{max}$, and the value of $x_{min}$ and $x_{max}$ that results in the maximum value of q is then selected as the separation-maximizing range of independent variable values.

Figure 14A:
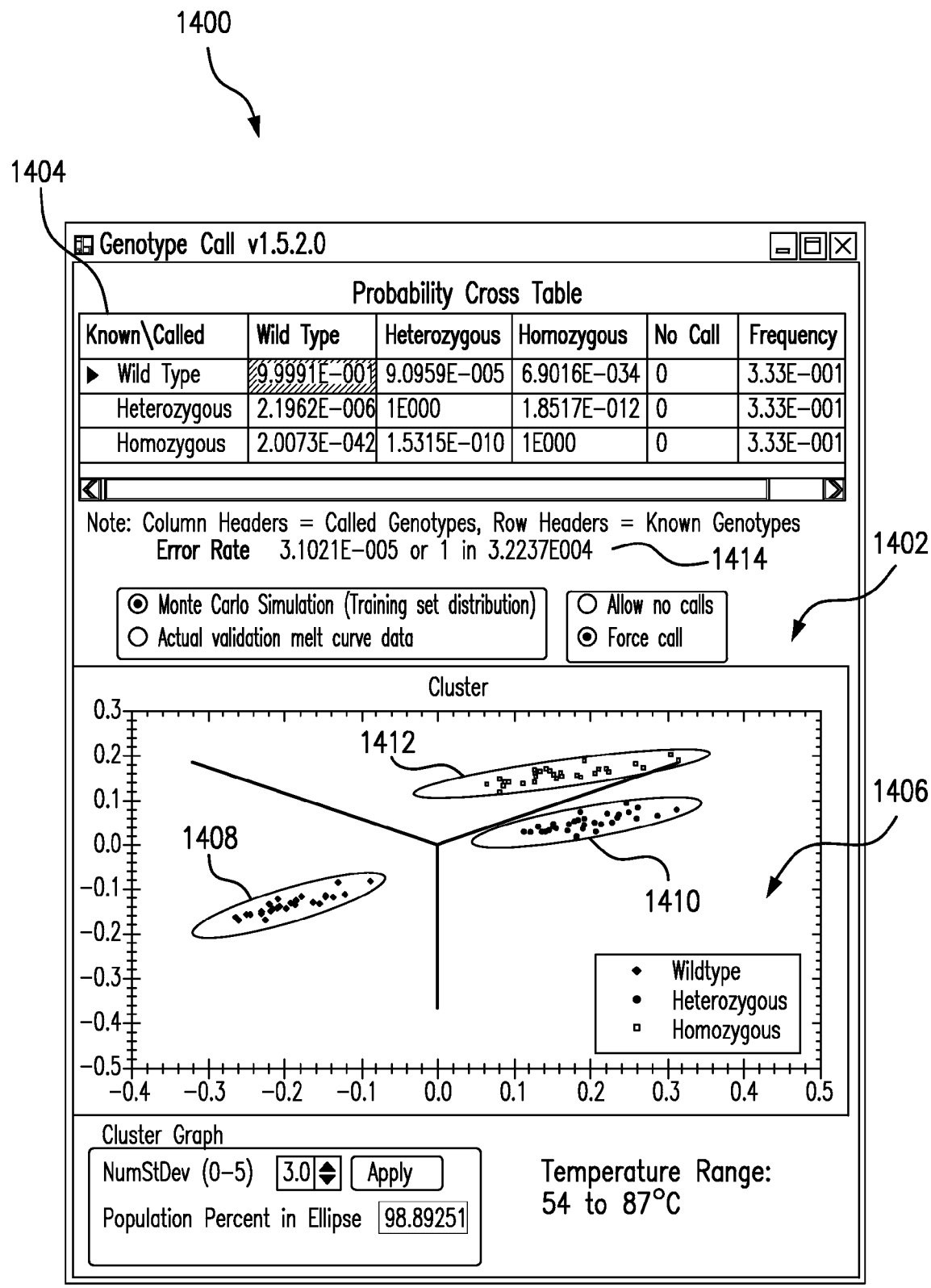
FIG. 14A illustrates a screen shot of an implementation of the methods and systems of the invention for an assay obtaining fluorescence versus temperature dynamic profiles of nucleic acids of the MTHFR 667 polymorphism class acquired over the temperature range between 54° C. and 87° C.
Figure 14B:
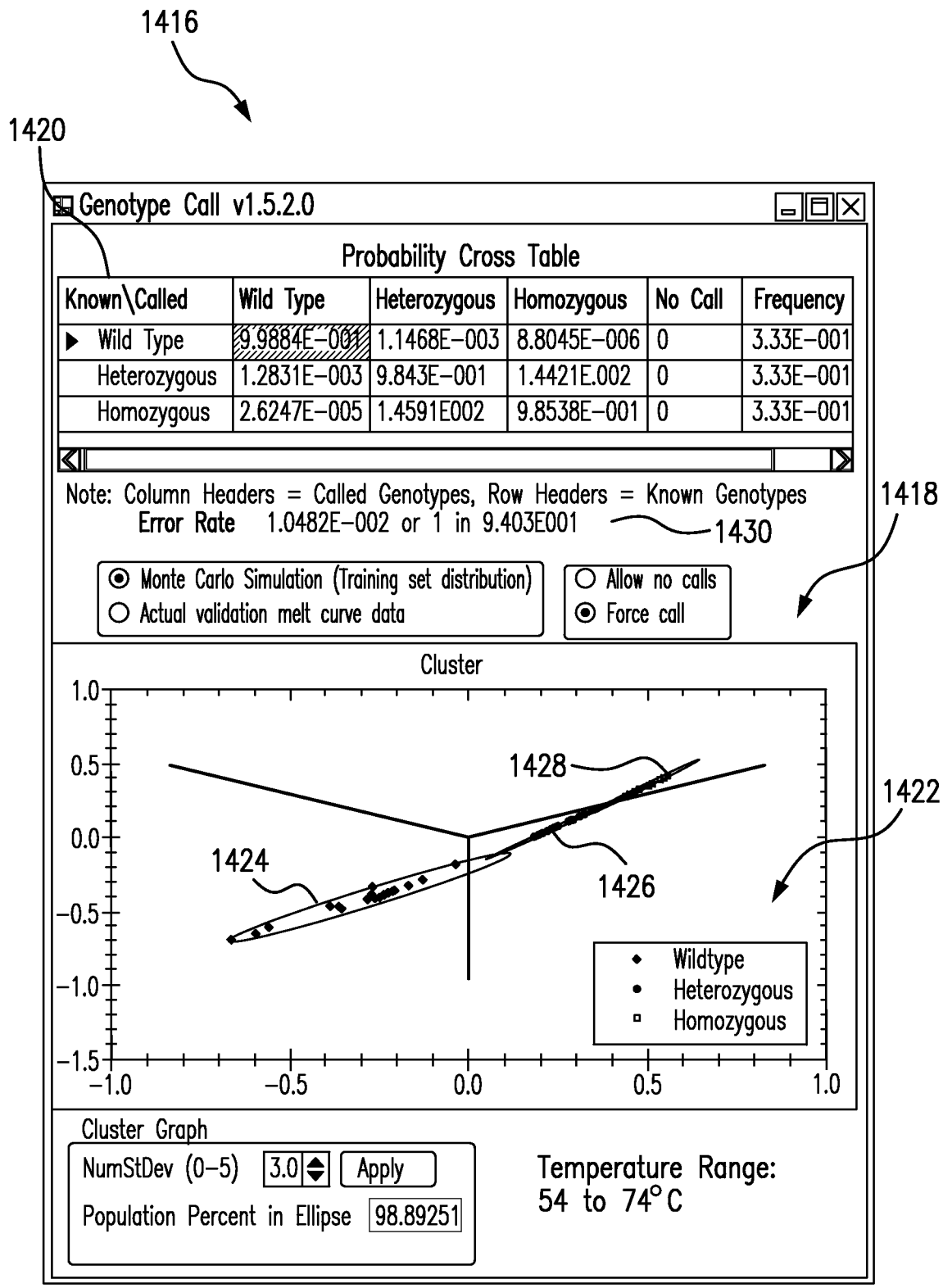
FIG. 14B illustrates a screen shot of an implementation of the methods and systems of the invention for an assay obtaining fluorescence versus temperature dynamic profiles of nucleic acids of the MTHFR 667 polymorphism class acquired over the temperature range between 54° C. and 74° C.
Figure 14C:
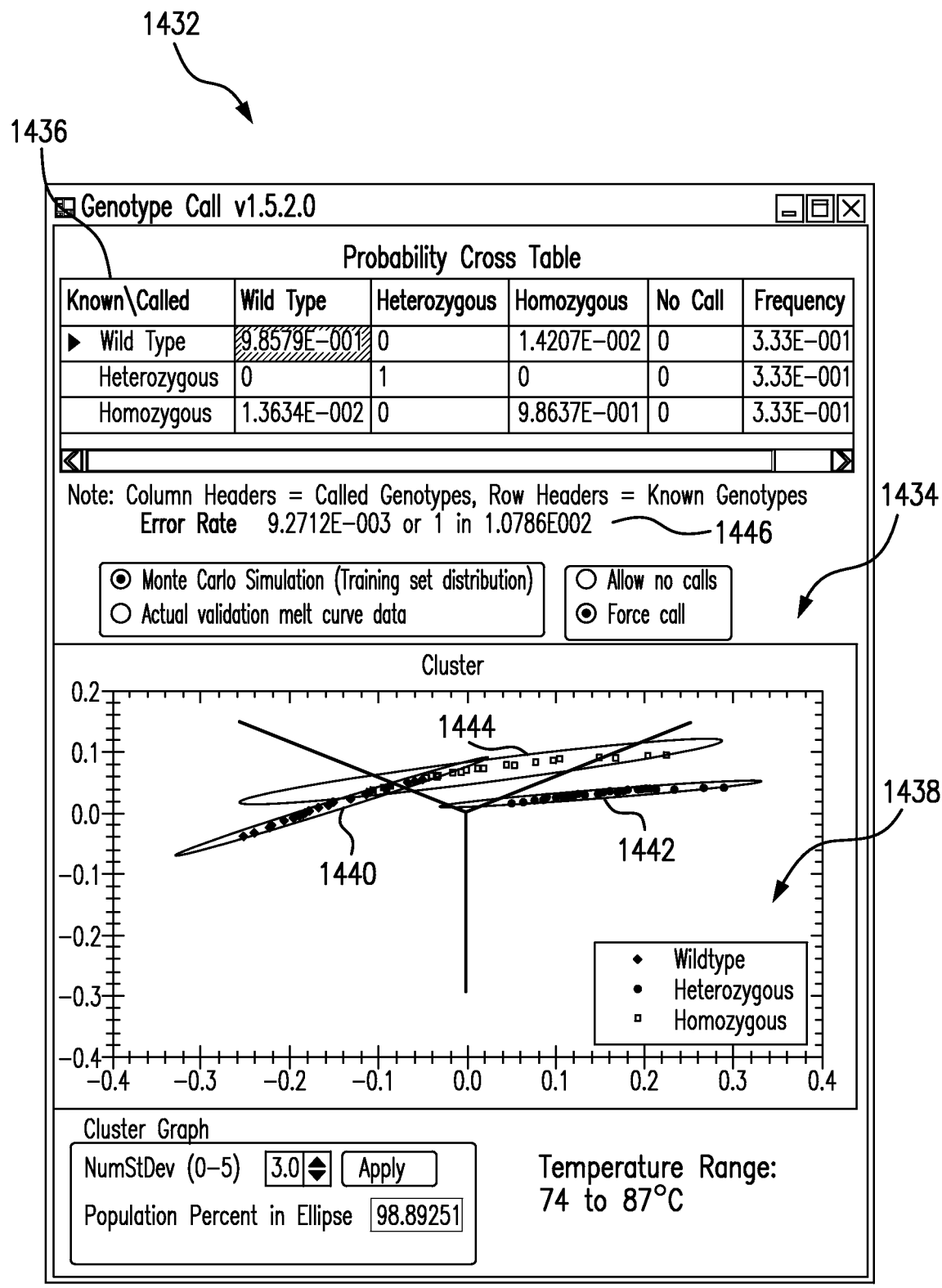
FIG. 14C illustrates a screen shot of an implementation of the methods and systems of the invention for an assay obtaining fluorescence versus temperature dynamic profiles of nucleic acids of the MTHFR 667 polymorphism class acquired over the temperature range between 74° C. and 87° C.

The present invention provides an alternate method of achieving the same goal. FIGS. 14A-C illustrate screen shots of an implementation of the disclosed method and system in accordance with one embodiment of the present invention. FIG. 14A illustrates an analysis 1400 of a first assay, in which dynamic profiles (which are thermal melt curves) of the various genotypes of the MTHFR 667 polymorphism are analyzed. In FIG. 14A, these thermal melt curves are analyzed over the temperature range of 54° C. to 87° C., as can be seen from the label in window 1402. Using the Monte Carlo methods, as described herein, a probability cross table 1404 is generated and output in window 1402. The wild-type, homozygous, and heterozygous genotype clusters are each plotted in cluster graph 1406. From this graph, it is possible to see that the wild-type cluster 1408, heterozygous cluster 1410, and homozygous mutant cluster 1412 are fairly discrete and separate from one another, and generally do not overlap. An overall expected misclassification rate (approximately 0.003%) is output at field 1414.

FIG. 14B illustrates an analysis 1416 of a second assay. The second assay differs from the first assay in FIG. 14A in that the thermal melt curves are analyzed over the temperature range of 54° C. to 74° C., as can be seen in the label in window 1418. Using the Monte Carlo methods, as described herein, a probability cross table 1420 is generated and output in window 1418. The wild-type, homozygous, and heterozygous genotype clusters are each plotted in cluster graph 1422. From this graph, one may notice that there is some overlap between the wild-type cluster 1424 and the heterozygous cluster 1426, as well as between the heterozygous cluster and the homozygous mutant cluster 1428. As would be expected from this visual indication, the overall expected misclassification rate output in field 1430 (which is around 1.048%) is larger in this assay than the expected misclassification rate for the assay that corresponds to FIG. 14A.

Figure 15A:
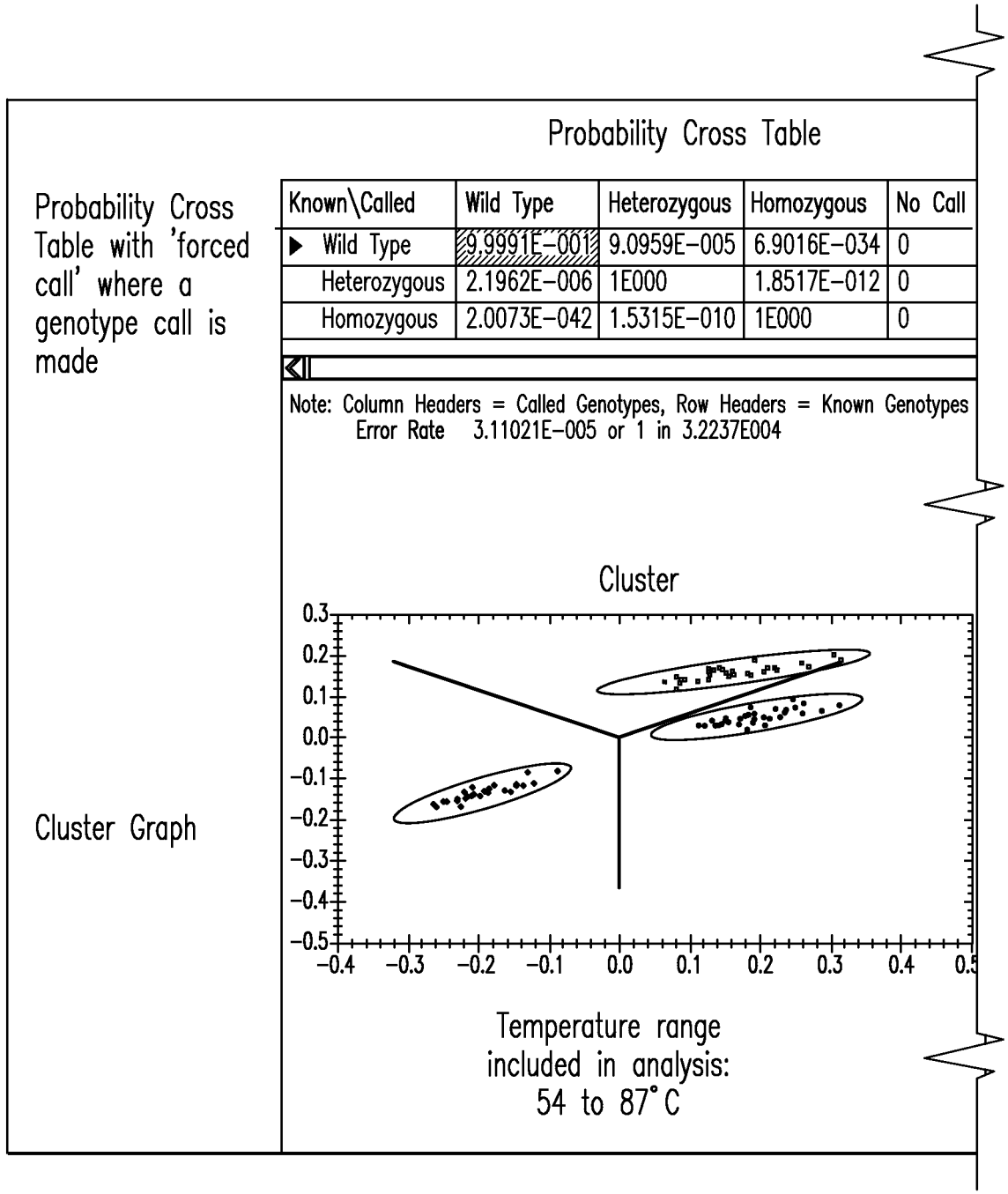
FIGS. 15A-C illustrate three cluster plots and cross-probability tables from FIGS. 14A-C side-by-side.
Figure 15B:
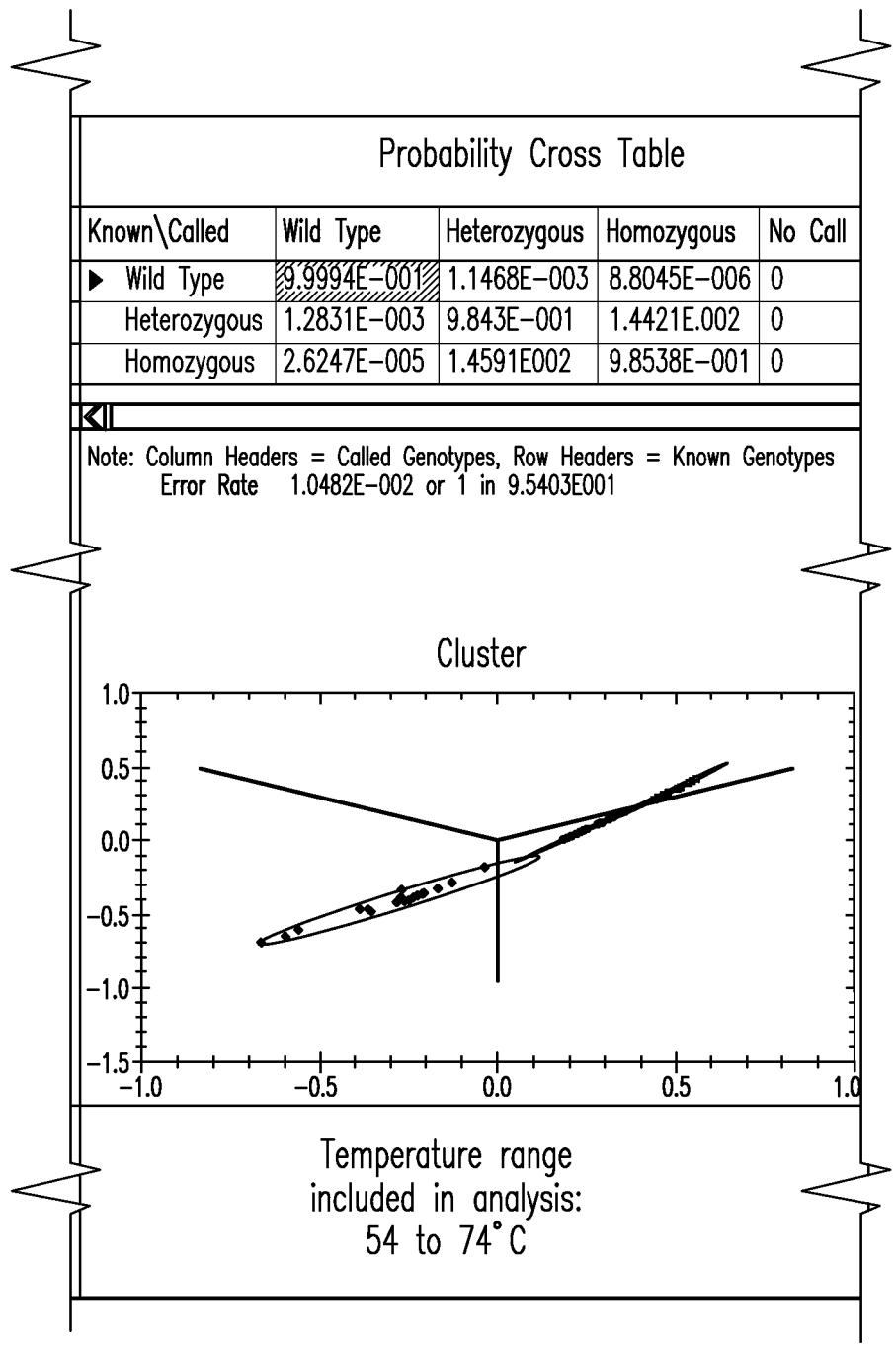
Figure 15C:
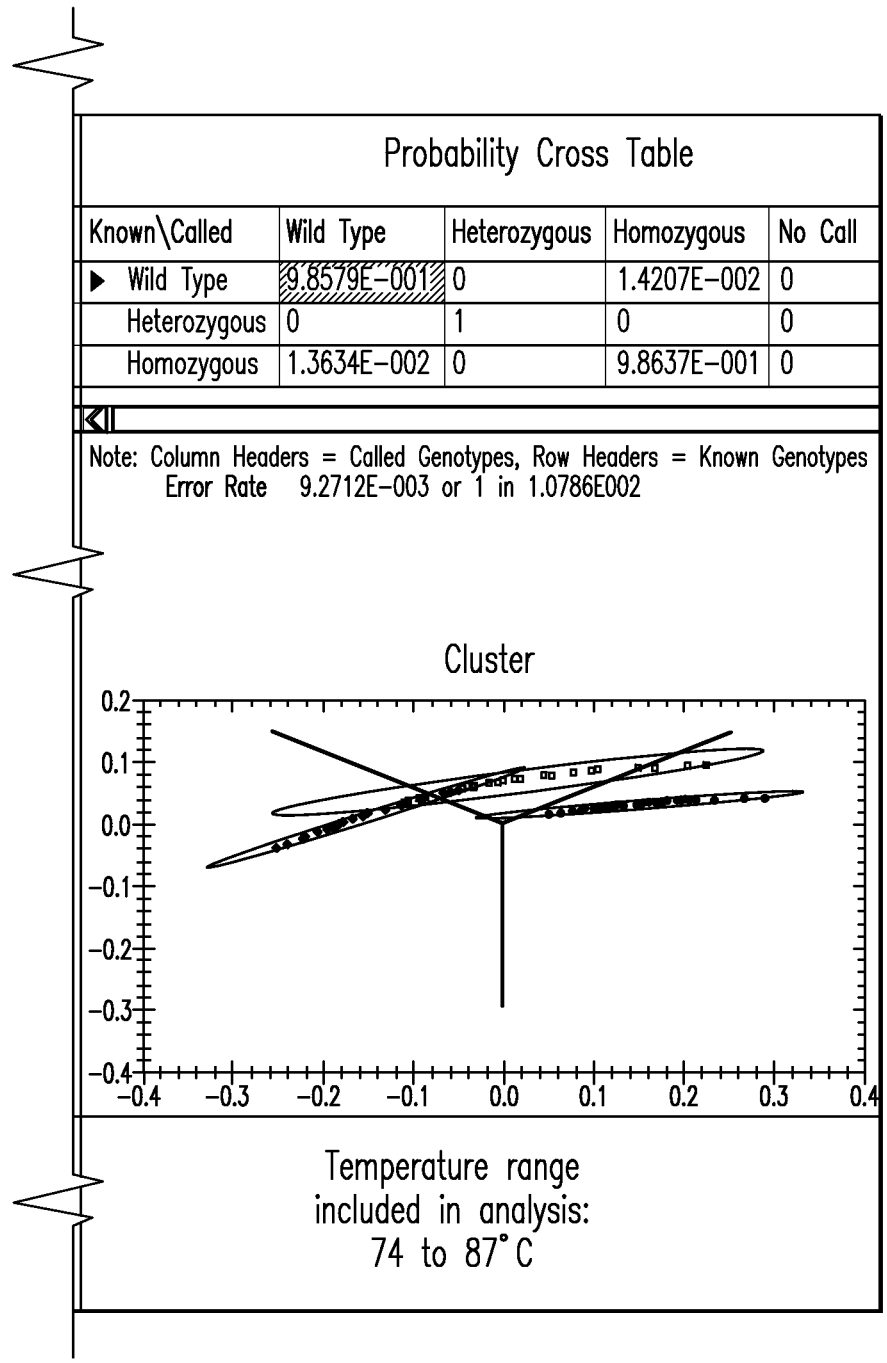

FIG. 14C illustrates an analysis 1432 of a third assay. The third assay differs from the first and second assays in FIGS. 14A and 14B in that the thermal melt curves are analyzed over the temperature range of 74° C. to 84° C., as can be seen from the label in the window 1434. Using the Monte Carlo methods, as described herein, a probability cross table 1436 is generated and output in window 1434. The wild-type, homozygous, and heterozygous genotype clusters are again each plotted in cluster graph 1438. From this graph, one may notice that there is now significant overlap between the wild-type cluster 1440 and the homozygous mutant cluster 1444, though the heterozygous cluster 1442 remains separate. The probability cross table reflects this, as the off-diagonal elements in the "Heterozygous" row are zero and the diagonal element (which corresponds to the probability that a data point representing a heterozygous thermal melt curve would be called as a heterozygous curve) is one. The overall expected misclassification rate output in field 1602 (around 0.927%) is larger in this assay than in the assay that corresponds to FIG. 14A but smaller than that for the assay in FIG. 14B. FIGS. 15A-C illustrate the three graphs and cross-probability tables from FIGS. 14A-C for easy comparison. In this example, from both the visual inspection of the graph and the quantitative comparison through the overall misclassification rate, the temperature range of 54° C. to 87° C. can be selected as superior to the other two ranges.

FIG. 16 displays three probability cross-tables for the assays corresponding to FIGS. 14A-C, but instead uses a 95% "no-call" threshold value. Implementing this no-call threshold value in this case results in an overall misclassification rate for the first assay of, effectively, zero, an overall misclassification rate for the second assay of approximately 0.130%, and an overall misclassification rate for the third assay of approximately 0.062%. In this embodiment, the overall no-call rate is also output in field 1602. One can see from this field that 0.003% of the points from the first assay resulted in a no-call, while approximately 3.365% of the points from second assay resulted in a no-call and approximately 2.880% of the points from the third assay resulted in a no-call. By allowing a user to set a no-call threshold, the user can gauge the improvement in the accuracy of the assay by introducing a no-call threshold while, at the same time, understanding how much data is discarded by setting the no-call threshold.

Figure 17:
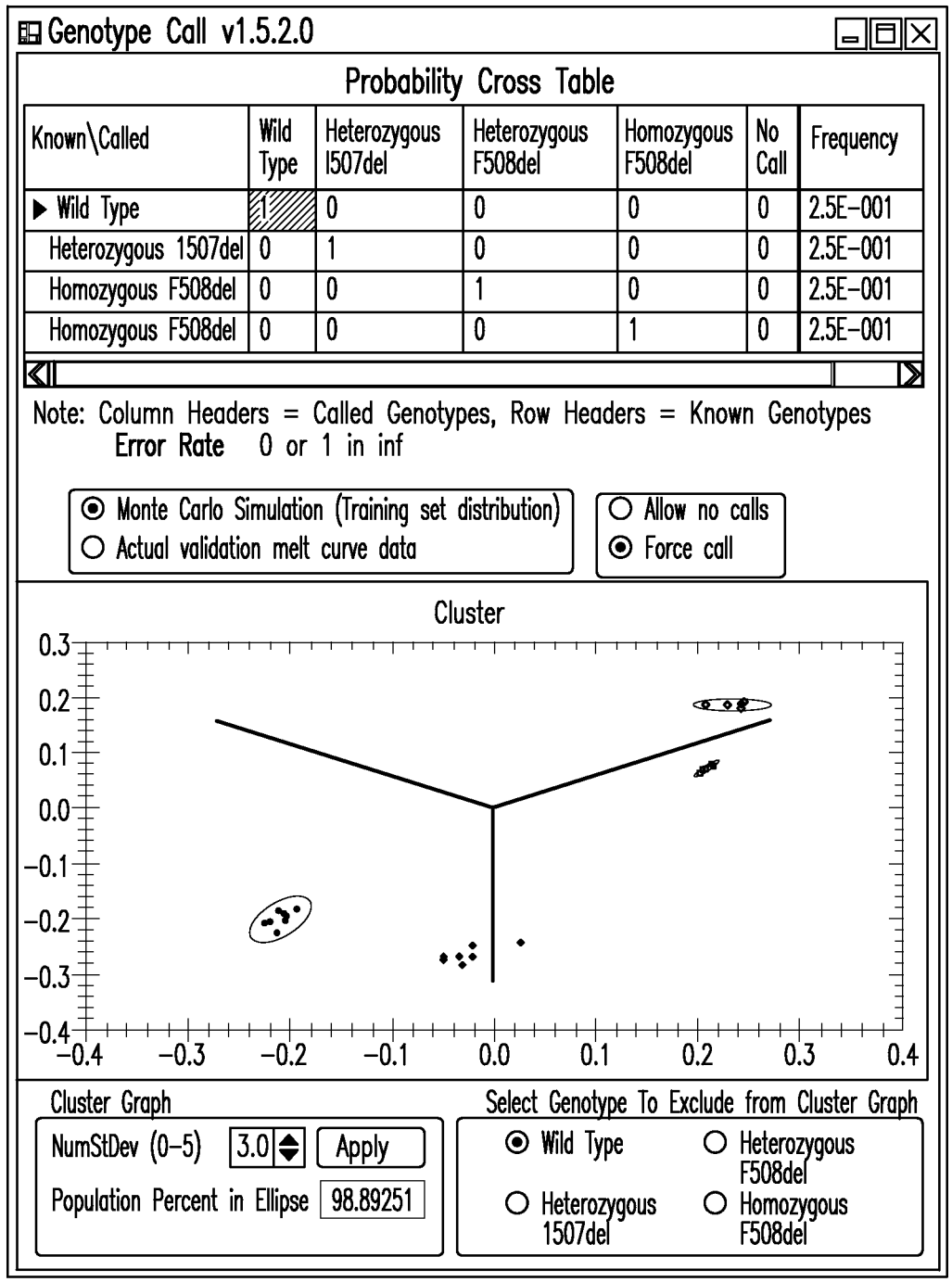
FIG. 17 illustrates a screen shot of an implementation of the methods and systems of the present invention for an assay obtaining fluorescence versus temperature dynamic profiles of nucleic acids of the class of possible genotypes in the Exon 10 region responsible for Cystic Fibrosis.
Figure 18A:
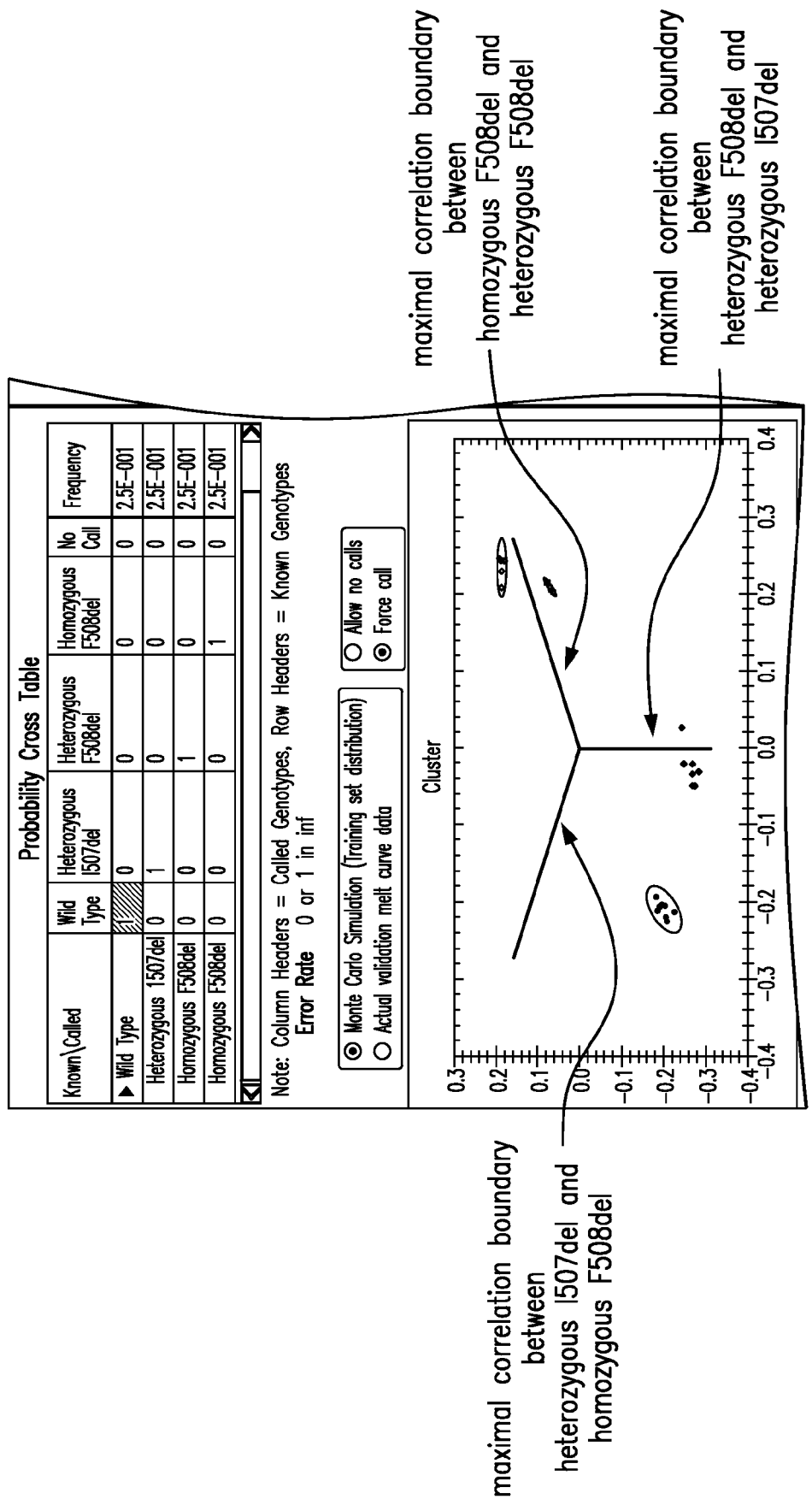
FIGS. 18A-D illustrate four separate two-dimensional plots each displaying boundaries at which the correlation of each genotype in the class of possible genotypes in the Exon 10 region responsible for Cystic Fibrosis is maximal against each other genotype.
Figure 18B:
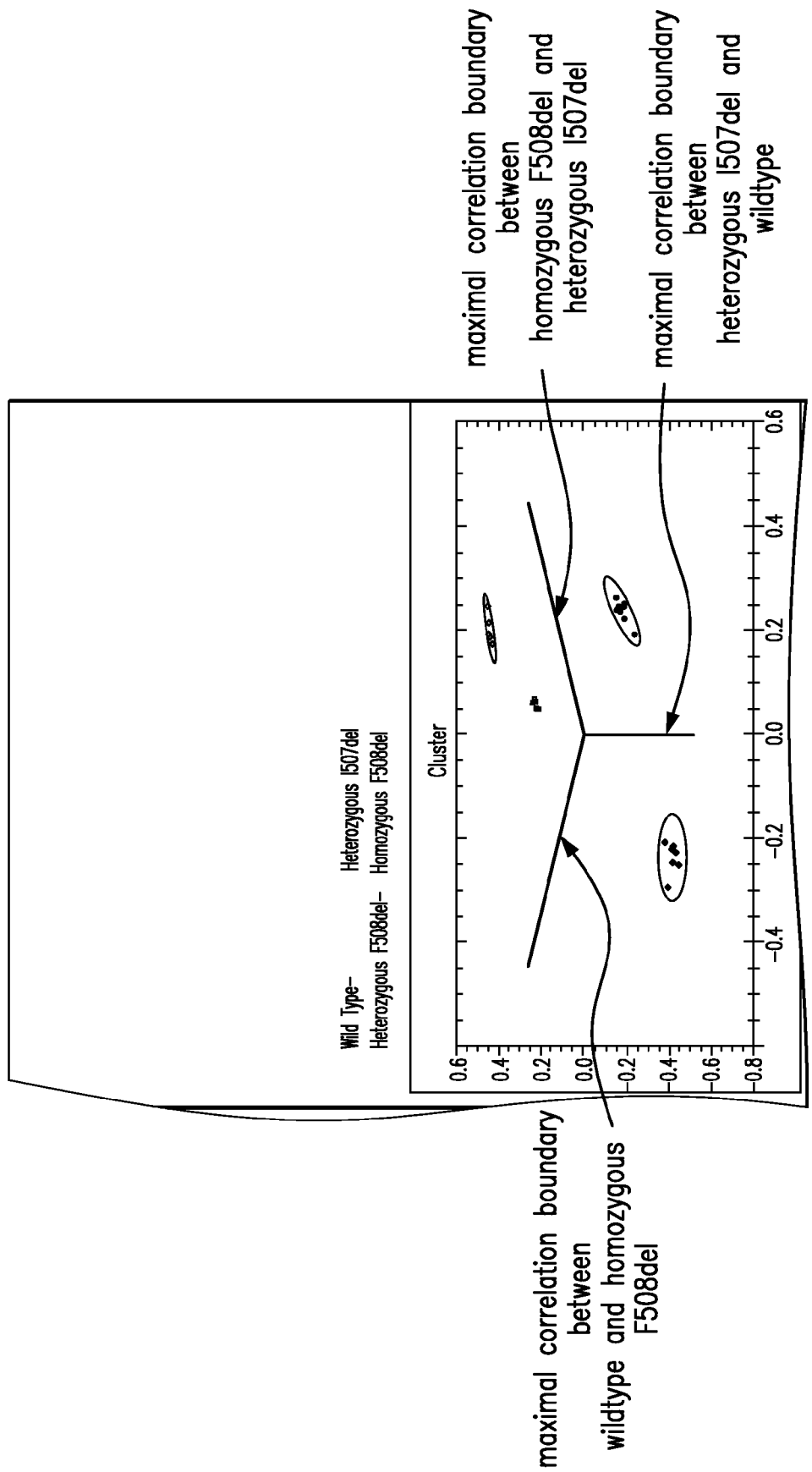
Figure 18C:
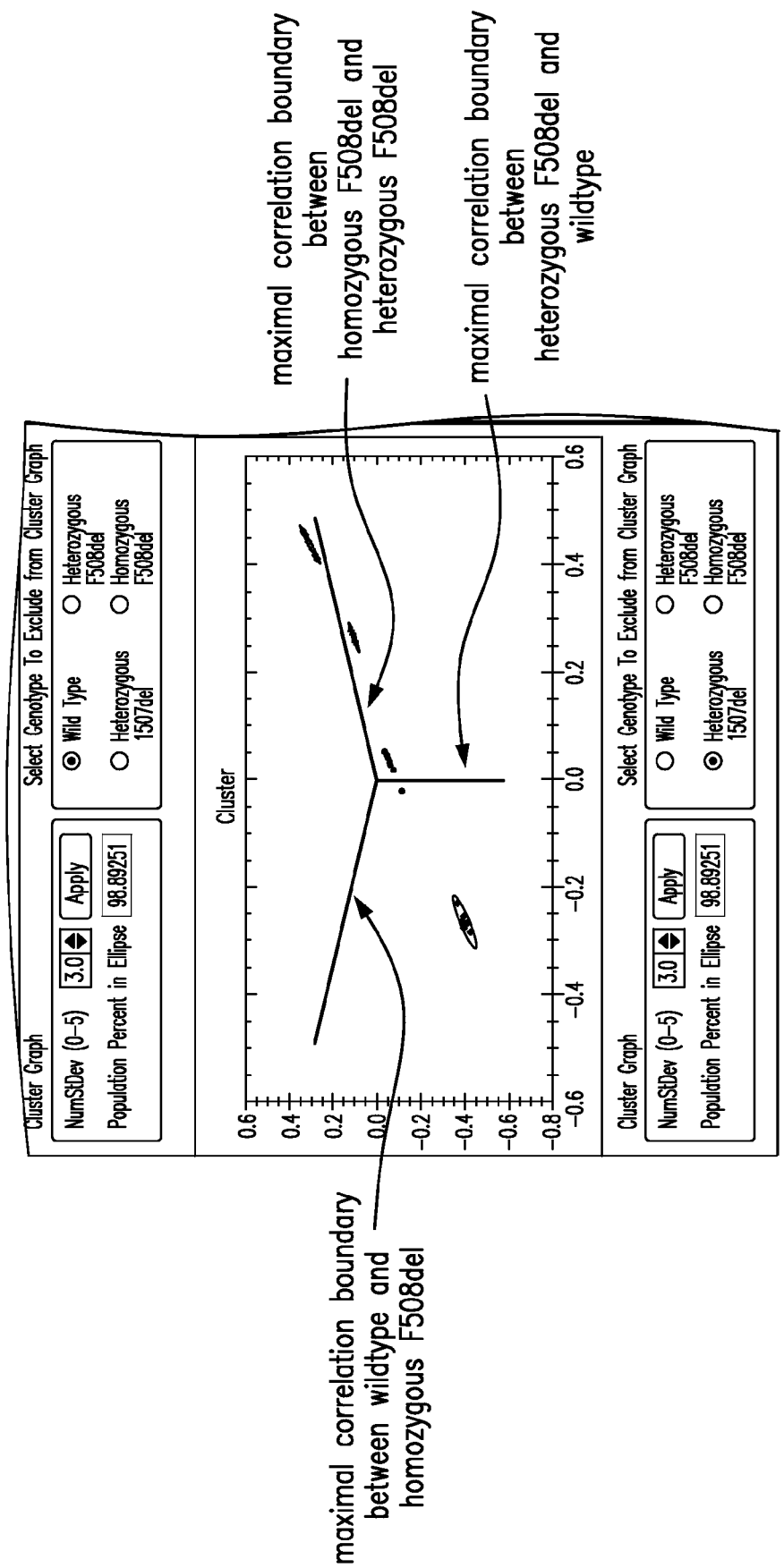
Figure 18D:
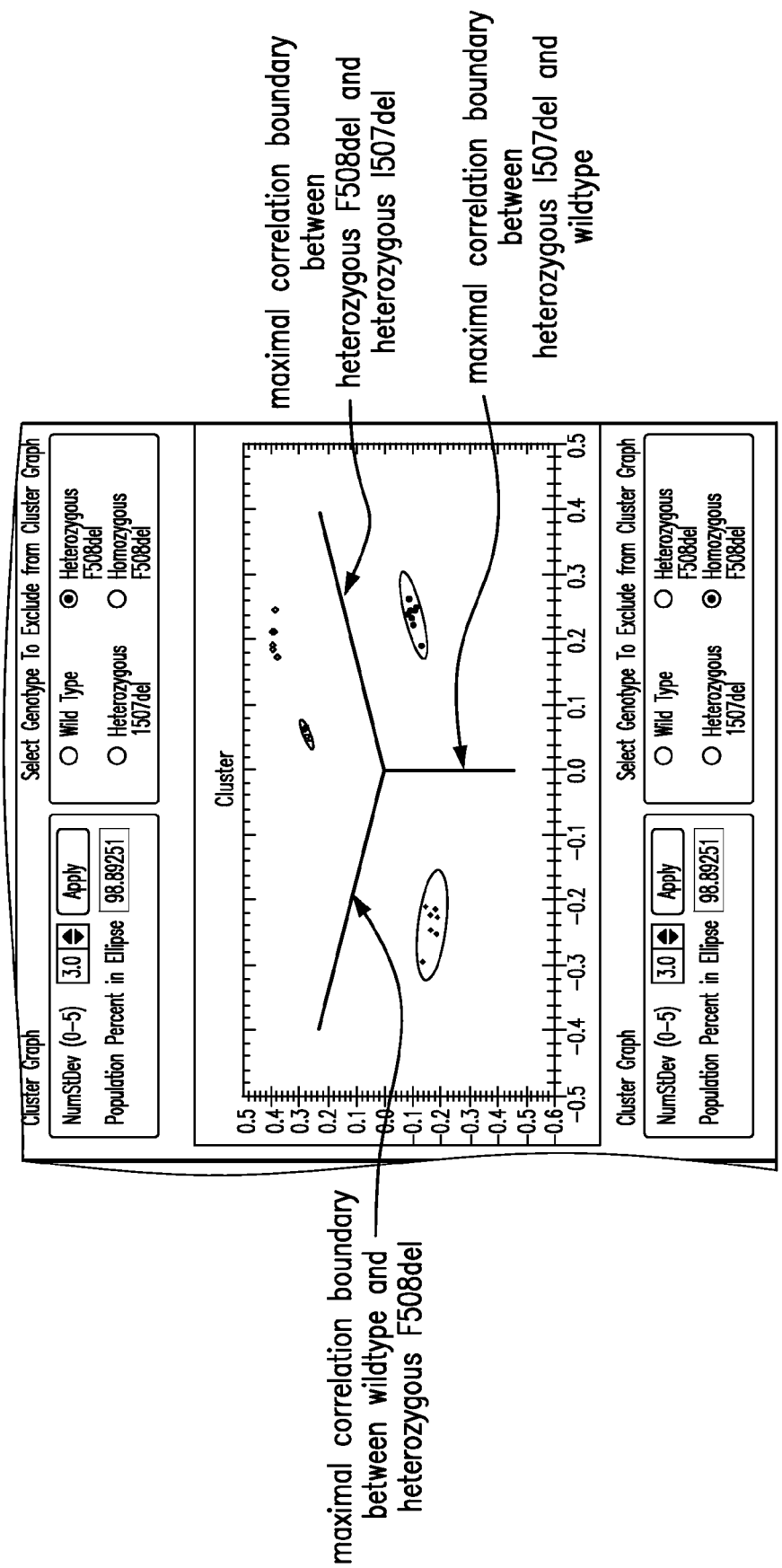

Those of ordinary skill will recognize that the methods and systems disclosed herein may be expanded to apply to genotypes with four or more possible genotypes, or contracted to apply to genotypes with two possible genotypes. For example, FIG. 17 illustrates another screen shot of an implementation of the methods and systems of the present invention for an assay obtaining fluorescence versus temperature dynamic profiles of nucleic acids of the class of possible genotypes in the Exon 10 region responsible for Cystic Fibrosis. In this class of genotypes, four separate genotypes may be possible: the wild type, heterozygous I507, heterozygous F508, and homozygous F508. FIGS. 18A-D display four separate cluster plots using four different projections of the data points for this class of genotypes from four-space; the axes in each cluster plot are labeled to indicate the maximal correlation boundary to which they correspond.

In accordance with other aspects, the present invention also provides systems implementing the various methods disclosed herein. For example, a system for implementing the genotype analysis methods described herein comprises a computer including a processor and a memory, a conversion module, a reduction module, a display device, and a plotting module. In some embodiments, the system may further include a statistical generation matrix module, an eigenvalue/eigenvector calculation module, and an ellipse-generation module.

The computer, including a processor and memory, may be any standard computing device including both a processor and a memory. The display device may be a monitor, a printer, a plotter, or any other device adapted to transmit information to a user. The conversion module may be configured to convert dynamic profiles, input into the computer, into data points, correlation vectors, etc. according to the methods disclosed herein, or in U.S. patent application Ser. No. 12/759,415, incorporated herein by reference. The reduction module may be configured to reduce the multi-dimensional data points into reduced-dimensional data points through the method for doing so outlined herein. The plotting module is configured to generate a plot of the reduced-dimensional data points for each genotype on the display device. In one embodiment, the conversion and reduction modules may both be appropriately programmed into a computer such that the computer is configured to perform the functions of both modules; this computer may further be the computer already included in the system. In another embodiment, the conversion and reduction modules may be encoded in software stored on a computer readable medium that, when executed by a computer, may configure the computer to perform the functions of the conversion and reduction modules.

The plotting module may also be configured to include multiple axes that each represent boundaries where correlation of the dynamic profiles represented is maximal against an average profile of one of the known genotypes for each genotype, as described herein. The plotting module may further be configured to display the extent to which clusters of the reduced-dimensional data points for each of the known genotypes are separated. The plotting module, in one embodiment, may be appropriately programmed into a computer; this computer, again, may be the computer including a processor and memory that is already included in the system. Further, the computer may be in communication with the display device. In another embodiment, the plotting module may be encoded in software stored on a computer readable medium that, when read and executed by a computer, may configure the computer to perform the function of the plotting module.

As stated above, some embodiments of the system may further include a statistical generation matrix module, an eigenvalue/eigenvector calculation module, and an ellipse-generation module. In these embodiments, the statistical matrix generation module may be configured to generate a mean data point and covariance matrix for each of the known genotypes from the set of reduced-dimensional data points representing dynamic profiles of each corresponding known genotype, as described above. The eigenvalue/eigenvector calculation module may be configured to calculate eigenvalues and eigenvectors of each of the covariance matrices, and the ellipse generation module may be configured to calculate a rotation angle and major/minor axis widths of an n-ellipse for each of the known genotypes, as described above. In embodiments including these modules, the plotting module may be configured to display the n-ellipses on the plot.

The eigenvalue/eigenvector calculation module may be, in an embodiment of the invention, an appropriately programmed computer. In another embodiment, the eigenvalue/eigenvector calculation module may be encoded in software stored on a computer readable medium that, when executed by a computer, may configure the computer to perform the functions of the eigenvalue/eigenvector calculation module. In another embodiment, the statistical matrix generation module may be programmed appropriately into a computer. Alternately, the statistical matrix generation module may be encoded in software stored on a computer readable medium that, when executed by a computer, may configure the computer to perform the functions of the statistical matrix generation module. The ellipse-generation module may be, in some embodiments, an appropriately programmed computer, or encoded in software stored on a computer readable medium that, when executed by a computer, may configure the computer to perform the functions of the ellipse-generation module. Again, the computer may be the computer including a processor and memory that is already included in the system.

In some embodiments, the conversion module may be configured to convert a dynamic profile of an unknown genotype of a nucleic acid to a multi-dimensional data point representing the unknown genotype; the reduction module may be configured to reduce the multi-dimensional data point representing the unknown genotype into a reduced-dimensional data point representing the unknown genotype; and the plotting module may be configured to plot the reduced-dimensional data point representing the unknown genotype on the plot. The system may further include an identification module, which may be configured to identify the genotype. The identification module may, again, be an appropriately programmed computer, or encoded in software stored on a computer readable medium that, when executed by a computer, may configure the computer to perform the functions of the statistical matrix generation module. Again, the computer may be the computer including a processor and memory that is already included in the system.

Another aspect of the invention may include a system for calculating an error statistic for identifying a genotype in a biological sample. In one embodiment, the system may include an assay, a computer, including a processor and a memory, and an output module. The assay may be any biological assay configured to generate dynamic profiles of each known genotype of a nucleic acid, wherein the dynamic profiles each comprise measurements of a signal representing a physical change of a nucleic acid containing the known genotype relative to an independent variable. As a non-limiting example, one such assay is disclosed in U.S. patent application Ser. No. 12/759,415.

In some embodiments, the computer may be configured to perform the following steps: a) converting the dynamic profiles generated by the assay of each known genotype to data points; b) transforming the data points such that each element of the data points is normally distributed, and grouping the data points by each known genotype to generate a data set for each known genotype; c) generating a mean data point and covariance matrix for each of the known genotypes from the data set for each genotype; d) generating N random data points with the same mean data point and covariance matrix for each of the known genotypes; and e) calculating an error statistic for the assay, based upon the generated N random data points for a known genotype.

In generating the N random data points for each known genotype, the computer may be configured to perform the steps of i) calculating a Cholesky factorization of the covariance matrix for each known genotype; ii) generating N random data points with a normalized distribution for each known genotype; iii) transforming the N random data points for each known genotype with the Cholesky factorization for that genotype to generate N transformed random data points for each known genotype; and iv) shifting each of the N random data points for each known genotype by the mean data point to generate a set of N random data points with the same mean data point and covariance matrix for each known genotype. The Monte Carlo method disclosed herein is one implementation of these steps. This method may effectively generate several different error statistics. For example, three preferred error statistics include an expected misclassification rate for one or all of the known genotypes, an overall expected misclassification rate for the assay as a whole, or a posterior probability that an unknown sample containing one of the known genotypes would be identified as an individual known genotype.

The computer may also be further configured to perform the steps of reducing the data points in each data set for each known genotype into reduced-dimensional data points. The output module may also be further adapted to generate a plot of the reduced-dimensional data points for each genotype. In this manner, the system may generate a plot according to genotype analysis methods disclosed herein.

In another embodiment, the system may include a first assay having a first set of assay parameters and a second assay having a second set of assay parameters. Each assay may be configured to generate a corresponding set of dynamic profiles of each known genotype of a nucleic acid, wherein the dynamic profiles each comprise measurements of a signal representing a physical change of a nucleic acid containing the known genotype relative to an independent variable. Preferably, the first and second set of assay parameters may have at least one differing assay parameter. In this embodiment, the computer may be further configured to perform the steps of f) repeating steps a-e described above for the second assay; and g) comparing the error statistic for the first assay and the error statistic for the second assay. Further, in this embodiment, the output module may be further configured to output the error statistic for the second assay. In one embodiment, the at least one differing assay parameter may be selected from the group consisting of reaction components, assay equipment, analysis software, measured independent variable, or range over which the independent variable of the dynamic profiles is measured, as disclosed above.

In one embodiment, the system may further include an input device. In this embodiment, the computer may be configured to perform step e) by receiving a no-call threshold value from the input device and calculating an error statistic for the assay, based upon the no-call threshold value and the generated N random data points for a known genotype, as disclosed above.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of analyzing dynamic profiles of genotypes of nucleic acids, the method comprising:
   using a computer, including a processor and a memory, to convert dynamic profiles of known genotypes of a nucleic acid to multi-dimensional data points, wherein the dynamic profiles each comprise measurements of a signal representing a physical change of a nucleic acid containing the known genotype relative to an independent variable;
   using the computer to reduce the multi-dimensional data points into reduced-dimensional data points;
   generating a plot of the reduced-dimensional data points for each genotype.

2. The method of claim 1, wherein said plot includes multiple axes that each represent boundaries where correlation of the dynamic profiles represented is maximal against average profiles of known genotypes for each genotype.

3. The method of claim 1, wherein the step of generating a plot includes showing the extent to which clusters of the reduced-dimensional data points for each of the known genotypes are separated.

4. The method of claim 1, wherein the multi-dimensional data points are (n+1)-dimensional data points and the reduced-dimensional data points are n-dimensional data points.

5. The method of claim 1, further comprising:
   using the computer to generate a mean data point and covariance matrix for each of the known genotypes from the set of reduced-dimensional data points representing dynamic profiles of each corresponding known genotype;
   using the computer to calculate eigenvalues and eigenvectors of each of the covariance matrixes;
   using the computer to calculate a rotation angle and major/minor axis widths of an n-ellipse for each of the known genotypes; and
   displaying the n-ellipses on the plot.

6. The method of claim 5, wherein the major/minor axis widths of each n-ellipse are proportioned such that each n-ellipse covers a multiple of the standard deviation of the reduced-dimensional data points representing the dynamic profiles of its respective genotype.

7. The method of claim 5, wherein the major/minor axis widths of each n-ellipse are proportioned such that each n-ellipse contains a predetermined percentage of the reduced-dimensional data points for its respective genotype.

8. The method of claim 5, wherein the rotation angle of the n-ellipse for a known genotype is calculated from the arctangent of the ratio of elements of an eigenvector of the covariance matrix for that genotype.

9. The method of claim 1, further comprising:
   using the computer to convert a dynamic profile of an unknown genotype of a nucleic acid to a multi-dimensional data point representing the unknown genotype;
   using the computer to transform the multi-dimensional data point representing the unknown genotype into a reduced-dimensional data point representing the unknown genotype; and
   plotting the reduced-dimensional data point representing the unknown genotype on the plot.

10. The method of claim 9, further comprising:
    using the computer to generate a mean data point and covariance matrix for each of the known genotypes from the set of reduced-dimensional data points representing dynamic profiles of each corresponding known genotype;
    using the computer to calculate eigenvalues of each of the covariance matrixes;
    using the computer to calculate rotation angle and major/minor axis widths of an n-ellipse for each of the known genotypes;
    displaying the n-ellipses on the plot; and
    determining if the reduced-dimensional data point representing the unknown genotype falls within one of the n-ellipses representing a known genotype.

11. The method of claim 10, wherein the major/minor axis widths of each n-ellipse are proportioned such that each n-ellipse covers a multiple of the standard deviation of the reduced-dimensional data points representing the dynamic profiles of its respective genotype.

12. The method of claim 10, wherein the major/minor axis widths of each n-ellipse are proportioned such that each n-ellipse contains a predetermined percentage of the reduced-dimensional data points for its respective genotype.

13. The method of claim 10, wherein the rotation angle of the n-ellipse for a known genotype is calculated from the arctangent of the ratio of elements of an eigenvector of the covariance matrix for that genotype.

14. The method of claim 10, further comprising the step of visually identifying the unknown genotype from the determination of whether the reduced-dimensional data point representing the unknown genotype falls within one of the n-ellipses representing a known genotype.

15. The method of claim 1, wherein the multi-dimensional data points are correlation vectors comprising correlation coefficients between the dynamic profile and an average dynamic profile for each known genotype in a class of genotypes, wherein the average dynamic profile of a known genotype comprises average measurements of the signal representing the physical change of a nucleic acid containing the known genotype relative to the independent variable.

16. A method of determining the identity of a genotype of a nucleic acid present in a biological sample, comprising:
   (a) generating a dynamic profile of an unknown genotype contained in the biological sample, wherein the dynamic profile comprises measurements of a signal representing a physical change of a nucleic acid containing the unknown genotype relative to an independent variable;
   (b) using a computer including a processor and a memory to compare the dynamic profile of the unknown genotype with an average dynamic profile of each known genotype in a class of known genotypes to generate a multi-dimensional data point, wherein the average dynamic profile of a known genotype comprises average measurements of a signal representing the physical change of a nucleic acid containing the known genotype relative to the independent variable and wherein the elements of the reduced-dimensional data point are correlation coefficients between the dynamic profile of the unknown genotype and the average dynamic profile for each known genotype in the class of genotypes;
   (c) transforming the multi-dimensional data point to a reduced-dimensional data point; and
   (d) generating a plot showing the reduced-dimensional data point for the unknown genotype.

17. The method of claim 16, wherein said step of comparing the dynamic profile of the unknown genotype with an average dynamic profile of each known genotype includes correlating the dynamic profile of the unknown genotype with an average dynamic profile of each known genotype.

18. The method of claim 16, further comprising the step of visually identifying the genotype based on the location of the reduced-dimensional data point for the unknown genotype on the plot.

19. A system for analyzing dynamic profiles of genotypes of nucleic acids, comprising:
   a computer, including a processor and a memory;
   a conversion module configured to convert dynamic profiles of known genotypes of a nucleic acid to multi-dimensional data points, wherein the dynamic profiles each comprise measurements of a signal representing a physical change of a nucleic acid containing the known genotype relative to an independent variable;
   a reduction module configured to reduce the multi-dimensional data points into reduced-dimensional data points;
   a display device; and
   a plotting module, configured to generate a plot of the reduced-dimensional data points for each genotype on the display device.

20. The system of claim 19, wherein said plot includes multiple axes that each represent boundaries where correlation of the dynamic profiles represented is maximal against average profiles of known genotypes for each genotype.

21. The system of claim 19, wherein the plotting module is configured to display the extent to which clusters of the reduced-dimensional data points for each of the known genotypes are separated.

22. The system of claim 19, wherein the multi-dimensional data points are (n+1)-dimensional data points and the reduced-dimensional data points are n-dimensional data points.

23. The system of claim 19, further comprising:
   a statistical matrix generation module configured to generate a mean data point and covariance matrix for each of the known genotypes from the set of reduced-dimensional data points representing dynamic profiles of each corresponding known genotype;
   an eigenvalue/eigenvector calculation module, configured to calculate eigenvalues and eigenvectors of each of the covariance matrixes; and
   an ellipse generation module, configured to calculate a rotation angle and major/minor axis widths of an n-ellipse for each of the known genotypes; and wherein the plotting module is configured to display the n-ellipses on the plot.

24. The system of claim 23, wherein the ellipse generation module proportions the major/minor axis widths of each n-ellipse such that each n-ellipse covers a multiple of the standard deviation of the reduced-dimensional data points representing the dynamic profiles of its respective genotype.

25. The system of claim 23, wherein the ellipse generation module proportions the major/minor axis widths of each n-ellipse such that each n-ellipse contains a predetermined percentage of the reduced-dimensional data points for its respective genotype.

26. The system of claim 23, wherein the rotation angle of the n-ellipse for a known genotype is calculated from the arctangent of the ratio of elements of an eigenvector of the covariance matrix for that genotype.

27. The system of claim 19, wherein the conversion module is configured to convert a dynamic profile of an unknown genotype of a nucleic acid to a multi-dimensional data point representing the unknown genotype;
   the reduction module is configured to reduce the multi-dimensional data point representing the unknown genotype into a reduced-dimensional data point representing the unknown genotype; and
   the plotting module is configured to plot the reduced-dimensional data point representing the unknown genotype on the plot; and further comprising an identification module configured to identify the genotype.

28. The system of claim 27, further comprising:
   a statistical matrix generation module configured to generate a mean data point and covariance matrix for each of the known genotypes from the set of reduced-dimensional data points representing dynamic profiles of each corresponding known genotype;
   an eigenvalue/eigenvector calculation module, configured to calculate eigenvalues and eigenvectors of each of the covariance matrixes; and
   an ellipse generation module, configured to calculate a rotation angle and major/minor axis widths of an n-ellipse for each of the known genotypes; and wherein the plotting module is configured to display the n-ellipses on the plot.

29. The system of claim 28, wherein the identification module is configured to determine if the reduced-dimensional data point representing the unknown genotype falls within one of the n-ellipses representing a known genotype.

30. The system of claim 28, wherein the ellipse generation module proportions the major/minor axis widths of each n-ellipse such that each n-ellipse covers a multiple of the standard deviation of the reduced-dimensional data points representing the dynamic profiles of its respective genotype.

31. The system of claim 28, wherein the ellipse generation module is configured to proportion the major/minor axis widths of each n-ellipse such that each n-ellipse contains a predetermined percentage of the reduced-dimensional data points for its respective genotype.

32. The system of claim 28, wherein the rotation angle of the n-ellipse for a known genotype is calculated from the arctangent of the ratio of elements of an eigenvector of the covariance matrix for that genotype.

33. The system of claim 19, wherein the multi-dimensional data points are correlation vectors comprising correlation coefficients between the dynamic profile and an average dynamic profile for each known genotype in a class of genotypes, wherein the average dynamic profile of a known genotype comprises average measurements of a signal representing the physical change of a nucleic acid containing the known genotype relative to the independent variable.

34. A method of calculating an error statistic for an assay for identifying a genotype in a biological sample, comprising:
  a) generating, using the assay, dynamic profiles of each known genotype of a nucleic acid, wherein said dynamic profiles each comprise measurements of a signal representing a physical change of a nucleic acid containing the known genotype relative to an independent variable;
  b) using a computer, including a processor and a memory, to convert the dynamic profiles of each known genotype to data points;
  c) using the computer to transform the data points such that each element of the data points is normally distributed, and grouping the data points by each known genotype to generate a data set for each known genotype;
  d) using the computer to generate a mean data point and covariance matrix for each of the known genotypes from the data set for each genotype;
  e) using the computer to, for each of the known genotypes, generate a set of N random data points with the same mean data point and covariance matrix for each of the known genotypes;
  f) using the computer to calculate an error statistic for the assay, based upon at least one of the generated sets of N random data points for a known genotype.

35. The method of claim 34, wherein the step of generating N random data points with the same mean data point and covariance matrix for each known genotype includes:
  i) using the computer to calculate a Cholesky factorization of the covariance matrix for each known genotype;
  ii) using the computer to generate a set of N random data points with a normalized distribution for each known genotype;
  iii) using the computer to transform the set of N random data points for each known genotype with the Cholesky factorization for that genotype to generate N transformed random data points for each known genotype;
  iv) using the computer to shift each of the set of N transformed random data points for each known genotype by the mean data point for that known genotype to generate N random data points with the same mean data point and covariance matrix for each known genotype.

36. The method of claim 34, wherein the error statistic is an expected misclassification rate for the known genotype.

37. The method of claim 34, wherein the error statistic is an overall expected misclassification rate for the assay.

38. The method of claim 34, wherein the error statistic is the posterior probability that an unknown sample containing one of the known genotypes would be identified as an individual known genotype.

39. The method of claim 34, wherein said independent variable in the assay is temperature, and said assay further comprises a fluorescent intercalating dye, and said measurements of a signal representing a physical change of a nucleic acid are measurements of fluorescence of the fluorescent dye.

40. The method of claim 34, further comprising the steps of using the computer to reduce the data points in each data set for each known genotype into reduced-dimensional data points and generating a plot of the reduced-dimensional data points for each genotype.

41. The method of claim 34, further comprising the step of generating a probability cross table, wherein the elements of the probability cross table are posterior probabilities that a known genotype would be identified as a possible known genotype.

42. The method of claim 34, wherein the computer further comprises an input device, and wherein step f) includes receiving a no-call threshold value from the input device and using the computer to calculate an error statistic for the assay, based upon the no-call threshold value and the at least one set of generated N random data points for a known genotype.

43. A method of optimizing an assay, comprising:
  a) generating, using a first assay having a first set of assay parameters, dynamic profiles of each known genotype of a nucleic acid, wherein said dynamic profiles each comprise measurements of a signal representing a physical change of a nucleic acid containing the known genotype relative to an independent variable;
  b) using a computer including a processor and a memory to convert the dynamic profiles of each known genotype from the first assay to data points;
  c) using the computer to transform the data points from step b) such that each element of the data points is normally distributed, and grouping the data points by each known genotype to generate a data set for each known genotype;
  d) using the computer to generate a mean data point and covariance matrix for each of the known genotypes from the data set for each genotype from step c);
  e) using the computer to, for each of the known genotypes, generate a set of N random data points with the same mean data point and covariance matrix for each of the known genotypes;
  f) using the computer to calculate an error statistic for the first assay, based upon at least one of the generated sets of N random data points for a known genotype;
  g) repeating steps a-f for at least a second assay having a second set of assay parameters, wherein the first and second set of assay parameters have at least one differing assay parameter;
  h) comparing the error statistic for the first assay and the error statistic for the second assay.

44. The method of claim 43, wherein said at least one differing assay parameter is selected from the group consisting of reaction components, assay equipment, analysis software, measured independent variable, or range over which the independent variable of the dynamic profiles is measured.

45. A system for calculating an error statistic for an assay for identifying a genotype in a biological sample, comprising:
  an assay configured to generate dynamic profiles of each known genotype of a nucleic acid, wherein said dynamic profiles each comprise measurements of a signal representing a physical change of a nucleic acid containing the known genotype relative to an independent variable;
  a computer, including a processor and a memory, configured to perform the steps of:
    a) converting the dynamic profiles generated by the assay of each known genotype to data points;
    b) transforming the data points such that each element of the data points is normally distributed, and grouping the data points by each known genotype to generate a data set for each known genotype;
c) generating a mean data point and covariance matrix for each of the known genotypes from the data set for each genotype;
d) generating N random data points with the same mean data point and covariance matrix for each of the known genotypes;
e) calculating an error statistic for the assay, based upon the generated N random data points for a known genotype; and
an output module configured to output the error statistic for the assay.

46. The system of claim 45, wherein the step of generating N random data points with the same mean data point and covariance matrix for the known genotype includes:
i) calculating a Cholesky factorization of the covariance matrix for each known genotype;
ii) generating N random data points with a normalized distribution for each known genotype;
iii) transforming the N random data points for each known genotype with the Cholesky factorization for that genotype to generate N transformed random data points for each known genotype;
iv) shifting each of the N random data points for each known genotype by the mean data point to generate a set of N random data points with the same mean data point and covariance matrix for each known genotype.

47. The system of claim 45, wherein the error statistic is an expected misclassification rate for one of the known genotypes.

48. The system of claim 45, wherein the error statistic is an overall expected misclassification rate for the assay.

49. The system of claim 45, wherein the error statistic is the posterior probability that an unknown sample containing one of the known genotypes would be identified as an individual known genotype.

50. The system of claim 45, wherein said independent variable in the assay is temperature, and said assay further comprises a fluorescent intercalating dye, and said measurements of a signal representing a physical change of a nucleic acid are measurements of fluorescence of the fluorescent dye.

51. The system of claim 45, wherein the computer is further configured to perform the steps of reducing the data points in each data set for each known genotype into reduced-dimensional data points and said output module is further adapted to generate a plot of the reduced-dimensional data points for each genotype.

52. The system of claim 45, wherein the computer is further configured to perform the step of generating a probability cross table, wherein the elements of the probability cross table are posterior probabilities that a known genotype would be identified as a possible known genotype; and wherein said output module is further configured to output the probability cross table for the assay.

53. The system of claim 45, wherein the assay is a first assay having a first set of assay parameters, and further comprising a second assay having a second set of assay parameters, wherein said second assay is configured to generate a second set of dynamic profiles of each known genotype of a nucleic acid, wherein said dynamic profiles each comprise measurements of a signal representing a physical change of a nucleic acid containing the known genotype relative to an independent variable, and said first and second set of assay parameters have at least one differing assay parameter; and
wherein said computer is further configured to perform the steps of:
f) repeating steps a-e for the second assay; and
g) comparing the error statistic for the first assay and the error statistic for the second assay; and
wherein said output module is further configured to output the error statistic for the second assay.

54. The system of claim 53, wherein said at least one differing assay parameter is selected from the group consisting of reaction components, assay equipment, analysis software, measured independent variable, or range over which the independent variable of the dynamic profiles is measured.

55. The system of claim 45, wherein the computer further comprises an input device, and wherein step e) includes receiving a no-call threshold value from the input device and calculating an error statistic for the assay, based upon the no-call threshold value and the generated N random data points for a known genotype.

56. A method of simulating N runs of an assay of a known genotype in a biological sample, comprising:
generating, using the assay, dynamic profiles of each known genotype of a nucleic acid, wherein said dynamic profiles each comprise measurements of a signal representing a physical change of a nucleic acid containing the known genotype relative to an independent variable
using a computer including a processor and a memory to convert dynamic profiles of the known genotypes of a nucleic acid to data points, wherein the dynamic profiles each comprise measurements of a signal representing a physical change of a nucleic acid containing the known genotype relative to an independent variable;
using the computer to transform the data points such that each element of the data points is normally distributed, and grouping the data points by each known genotype to generate a data set for each known genotype;
using the computer to generate a mean data point and covariance matrix for each of the known genotypes from the data set for each genotype;
using the computer to, for each of the known genotypes, generate a set of N random data points with the same mean data point and covariance matrix for the known genotype.

* * * * *